US008148114B2

(12) United States Patent  (10) Patent No.: US 8,148,114 B2
Mohapatra  (45) Date of Patent: Apr. 3, 2012

(54) MATERIALS AND METHODS FOR TREATMENT OF INFLAMMATORY AND CELL PROLIFERATION DISORDERS

(75) Inventor: Shyam S Mohapatra, Tampa, FL (US)

(73) Assignee: University of South Florida, Tampa, FL (US)

( * ) Notice: Subject to any disclaimer, the term of this patent is extended or adjusted under 35 U.S.C. 154(b) by 266 days.

(21) Appl. No.: 12/259,110

(22) Filed: Oct. 27, 2008

(65) Prior Publication Data

US 2009/0176706 A1  Jul. 9, 2009

Related U.S. Application Data

(63) Continuation of application No. 11/059,814, filed on Feb. 17, 2005, now abandoned.

(60) Provisional application No. 60/521,072, filed on Feb. 17, 2004.

(51) Int. Cl.
A61P 35/00 (2006.01)
A61K 31/7088 (2006.01)
C07H 21/04 (2006.01)
C12N 15/09 (2006.01)
C12N 15/74 (2006.01)

(52) U.S. Cl. .................. 435/91.1; 435/69.1; 435/320.1; 435/375; 435/455; 536/23.1

(58) Field of Classification Search .................. None
See application file for complete search history.

(56) References Cited

U.S. PATENT DOCUMENTS

| | | | |
|---|---|---|---|
| 4,753,945 A | 6/1988 | Gilbard et al. | |
| 4,957,735 A | 9/1990 | Huang | |
| 5,013,556 A | 5/1991 | Woodle et al. | |
| 5,043,164 A | 8/1991 | Huang et al. | |
| 5,087,617 A | 2/1992 | Smith | |
| 5,093,246 A | 3/1992 | Cech et al. | |
| 5,116,742 A | 5/1992 | Cech et al. | |
| 5,135,917 A | 8/1992 | Burch | |
| 5,144,019 A | 9/1992 | Rossi et al. | |
| 5,168,053 A | 12/1992 | Altman et al. | |
| 5,176,996 A | 1/1993 | Hogan et al. | |
| 5,180,818 A | 1/1993 | Cech et al. | |
| 5,190,931 A | 3/1993 | Inouye | |
| 5,272,262 A | 12/1993 | Rossi et al. | |
| 5,545,614 A | 8/1996 | Stamler et al. | |
| 5,595,756 A * | 1/1997 | Bally et al. ................. 424/450 |
| 5,602,143 A | 2/1997 | Krauss | |
| 5,625,056 A | 4/1997 | Genieser et al. | |
| 5,646,032 A | 7/1997 | Volker ter Meulen et al. | |
| 5,665,861 A | 9/1997 | Forssmann et al. | |
| 5,686,101 A | 11/1997 | Tagawa et al. | |
| 5,691,310 A | 11/1997 | Vesely | |
| 5,705,187 A | 1/1998 | Unger | |
| 5,817,856 A | 10/1998 | Tirosh et al. | |
| 5,820,873 A | 10/1998 | Choi et al. | |
| 5,840,341 A | 11/1998 | Watts et al. | |
| 5,858,694 A | 1/1999 | Piazza et al. | |
| 6,013,630 A | 1/2000 | Shimkets | |
| 6,028,055 A | 2/2000 | Lowe et al. | |
| 6,184,037 B1 | 2/2001 | Rolland et al. | |
| 6,506,559 B1 | 1/2003 | Fire et al. | |
| 6,528,245 B2 | 3/2003 | Sanchez-Ramos et al. | |
| 6,943,147 B2 | 9/2005 | Vesely | |
| 7,022,828 B2 | 4/2006 | McSwiggen | |
| 7,354,908 B2 | 4/2008 | Mohapatra et al. | |
| 7,488,713 B2 | 2/2009 | Vesely | |
| 7,595,303 B1 | 9/2009 | Mohapatra et al. | |
| 7,655,772 B2 * | 2/2010 | Mohapatra ................. 536/23.1 |
| 7,825,092 B2 | 11/2010 | Vesely | |
| 7,846,900 B2 | 12/2010 | Vesely | |
| 2001/0027181 A1 | 10/2001 | Kitakaze et al. | |
| 2002/0094326 A1 | 7/2002 | Donahue et al. | |
| 2002/0146821 A1 | 10/2002 | Sanchez-Ramos et al. | |
| 2002/0193579 A1 | 12/2002 | Usman et al. | |
| 2003/0069186 A1 | 4/2003 | Burnett et al. | |
| 2003/0073628 A1 | 4/2003 | Shailubhai et al. | |
| 2003/0105000 A1 | 6/2003 | Pero et al. | |
| 2003/0138793 A1 | 7/2003 | Su et al. | |
| 2003/0147943 A1 | 8/2003 | Luo et al. | |
| 2003/0204063 A1 | 10/2003 | Gravel et al. | |
| 2003/0215528 A1 | 11/2003 | Graham et al. | |
| 2004/0002458 A1 | 1/2004 | Seilhamer et al. | |
| 2004/0067889 A1 | 4/2004 | Belenky et al. | |
| 2004/0138134 A1 | 7/2004 | Golembo et al. | |
| 2004/0146549 A1 | 7/2004 | Ben-Sasson et al. | |
| 2004/0171550 A1 | 9/2004 | Backstrom et al. | |
| 2004/0203081 A1 | 10/2004 | James et al. | |
| 2004/0213782 A1 | 10/2004 | Wax et al. | |

(Continued)

FOREIGN PATENT DOCUMENTS

| | | |
|---|---|---|
| WO | WO 99/32619 A1 | 7/1999 |
| WO | WO 00/07156 A2 | 11/2000 |
| WO | WO 01/68836 A3 | 9/2001 |
| WO | WO 01/75164 A3 | 10/2001 |
| WO | WO 01/92513 A1 | 12/2001 |
| WO | WO 2004/011498 A3 | 2/2004 |
| WO | WO 2004/022003 A2 | 3/2004 |
| WO | WO 2004/022579 A3 | 3/2004 |
| WO | WO 2004/083236 A3 | 9/2004 |
| WO | WO 2005/094420 A3 | 10/2005 |
| WO | WO 2006/026536 A3 | 3/2006 |
| WO | WO 2007/127487 A2 | 11/2007 |
| WO | WO 2007/130672 A3 | 11/2007 |
| WO | WO 2009/073527 A2 | 6/2009 |

OTHER PUBLICATIONS

Sporn MB, Suh, N, "Chemoprevention of cancer," Carcinogenesis, 2000, 21(3): 525-530.*

(Continued)

*Primary Examiner* — Julie Ha
(74) *Attorney, Agent, or Firm* — Saliwanchik, Lloyd & Eisenschenk

(57) ABSTRACT

Compositions and methods for treatment of inflammatory and cell proliferation disorders using natriuretic hormone peptide (NP), polynucleotides encoding NP, or agents that reduce the activity of atrial natriuretic peptide receptor A (NPR-A).

20 Claims, 11 Drawing Sheets

U.S. PATENT DOCUMENTS

| | | | |
|---|---|---|---|
| 2004/0224903 A1 | 11/2004 | Berry et al. |
| 2004/0229784 A1 | 11/2004 | Vesely |
| 2004/0258687 A1 | 12/2004 | Waldman et al. |
| 2004/0266673 A1 | 12/2004 | Bakis et al. |
| 2005/0008617 A1 | 1/2005 | Chen et al. |
| 2005/0014287 A1 | 1/2005 | Friese et al. |
| 2005/0014289 A1 | 1/2005 | Parsons et al. |
| 2005/0176641 A1 | 8/2005 | Bakis et al. |
| 2005/0209139 A1 | 9/2005 | Vesely |
| 2005/0266093 A1 | 12/2005 | Mohapatra |
| 2005/0272650 A1 | 12/2005 | Mohapatra |
| 2006/0014689 A1 | 1/2006 | Vesely |
| 2006/0019256 A1 | 1/2006 | Clarke et al. |
| 2006/0110359 A1 | 5/2006 | Sanchez-Ramos et al. |
| 2006/0205642 A1 | 9/2006 | Vesely |
| 2006/0276382 A1 | 12/2006 | Mohapatra |
| 2007/0036867 A1 | 2/2007 | Mohapatra et al. |
| 2007/0116767 A1 | 5/2007 | Mohapatra |
| 2007/0265204 A1 | 11/2007 | Mohapatra et al. |
| 2008/0039394 A1 | 2/2008 | Vesely |
| 2008/0070858 A1 | 3/2008 | Mohapatra |
| 2008/0214437 A1 | 9/2008 | Mohapatra et al. |
| 2009/0062206 A1 | 3/2009 | Vesely |
| 2009/0170196 A1 | 7/2009 | Vesely |
| 2009/0176706 A1 | 7/2009 | Mohapatra |
| 2011/0034386 A1 | 2/2011 | Vesely |
| 2011/0039777 A1 | 2/2011 | Vesely |

OTHER PUBLICATIONS

Cancer Drug Design and Discovery Neidle, Stephen, ed. (Elsevier/Academic Press, 2008) pp. 427-431.*

Rudinger J, "Characteristics of the amino acids as components of a peptide hormone sequence," Peptide Hormones, JA Parsons Edition, University Park Press, Jun. 1976, pp. 1-7.*

"Designing Custom Peptides," from SIGMA Genosys, pp. 1-2. Accessed Dec. 16, 2004.*

Schinzel R, Drueckes P, "The phosphate recognition site of Escherichia coli maltodextrin phosphorylase," FEBS, Jul. 1991, 286(1,2): 125-128.*

Berendsen HJC, "A Glimpse of the Holy Grail?" Science, 1998, 282: 642-643.*

Voet D, Voet JG, Biochemistry, Second Edition, John Wiley & Sons, Inc., 1995, pp. 235-241.*

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

U.S. Appl. No. 11/799,225, filed Apr. 30, 2007, Mohapatra.

U.S. Appl. No. 10/526,584, filed Mar. 3, 2005, Mohapatra.

Abbey, S. et al. "Lysophosphatidic acid inhibits C-type natriuretic peptide activation of guanylyl cyclase-B" Endocrinology, 2003, 144:240-246.

Angus, R.M. et al. "Effect of inhaled atrial natriuretic peptide on methacholine induced bronchoconstriction in asthma" Clin Exp Allergy 1994, 24:784-788.

Auerbach, R. et al. "Angiogenesis assays, Problems and Pitfalls" Cancer and Metastasis Reviews 2000, 19: 167-172.

Bliss, D. et al. "Expression of the atrial natriuretic factor gene in small cell lung cancer tumors and tumor cell lines" J Natl Can Inst, 1990, 82:305-310.

Bryan, P.M. et al. "The Atrial Natriuretic Peptide Receptor (NPR-A/GC-1) is Dephosphorylated by Distinct Microcystin-sensitive and Magnesium-dependent Protein Phosphatase" J. Biol. Chem. 2002, 277(18): 16041-16047.

Chen, S. et al. "1, 25 dihydroxyvitamin D amplifies type A natriuretic peptide receptor expression and activity in target cells" J. Am. Soc. Nephrol., 2005, 16:329-339.

Chen, X. et al. "Human bone marrow stromal cell cultures" J Neurosci Res, 2002, 69:687-691.

Chen, X. et al. "Ischemic rat brain extracts induce human marrow stromal cell growth factor production" Neuropathology, 2002, 22:275-279.

Chen, J. et al. "Therapeutic benefit of intravenous administration of bone marrow stromal cells after cerebral ischemia in rats" Stroke, 2001, 32:1005-1011.

Chen, J. et al. "Therapeutic benefit of intracerebral transplantation of bone marrow stromal cells after cerebral ischemia in rats" J. Neurological Sci., 2001, 189:49-57.

Chopp, M. et al. "Spinal cord injury in rat: treatment with bone marrow stromal cell transplantation" Neuroreport, 2000, 11:3001-3005.

Delporte, C. et al. "Discovery of a potent atrial natriuretic peptide antagonist for $ANP_A$ receptors in the human neuroblastoma NB-OK-1 cell line" Eur. J. Pharmacol., 1992, 224(2-3):183-188.

Doczi, T.P. et al, "Atrial natriuretic peptide (ANP) attenuates brain oedema accompanying experimental subarachnoid haemorrhage" Acta Neurochir (Wien), 1995, 132:87-91.

Drewett, J.G. and Garbers, D.L. "The family of guanylyl cyclase receptors and their ligands" Endocrine Reviews, 1994, 15(2):135-162.

El-Ayoubi, R. et al. "Urinary responses to acute moxonidine are inhibited by natriuretic peptide receptor antagonist" Br. J. Pharmacol., 2005, 145:50-56.

Ernst, P. "Review article: the role of inflammation in the pathogenesis of gastric cancer" Aliment Pharmacol Ther., 1999, 13(1):13-18.

Fonarow, G.C. et al. "Combining natriuretic peptides and necrosis markers in determining prognosis in heart failure" Rev. Cardiovasc. Med., 2003, 4(suppl 4):S20-S28.

Fujiseki, Y. et al. "Natriuretic peptide receptors, NPR-A and NPR-B, in cultured rabbit retinal pigment epithelium cells" Jpn. J. Pharmacol., 1999, 79(3):359-368.

Fürst, R. et al. "Atrial natriuretic peptide induces mitogen-activated protein kinase phosphatase-1 in human endothelial cells via Rac1 and NAD(P)H oxidase/Nox2-activation" Circ. Res., 2005, 96:43-53.

Gower, W.R. et al. "Regulation of atrial natriuretic peptide secretion by cholinergic and PACAP neurons of the gastric antrum" Am. J. Physiol. Gastrointest. Liver Physiol., 2003, 284:G68-G74.

Greten, F.R. et al. "IKKβ links inflammation and tumorigenesis in a mouse model of colitis-associated cancer" Cell, 2004, 118:285-296.

Gura T. "Cancer Models: Systems for Identifying New Drugs are Often Faulty" Science 1997, 278(5340): 1041-1042, 1-5.

Izumi, T. et al. "Blockade of the natriuretic peptide receptor guanylyl cyclase-A inhibits NF-κB activation and alleviates myocardial ischemia/reperfusion injury" J Clin Invest 2001, 108:203-213.

Jain, R.K. "Barriers to Drug Delivery in Solid Tumors" Scientific American Jul. 1994, 58-65.

Jensen, K.T. et al. "A new, fast and reliable radioimmunoassay of brain natriuretic peptide in human plasma. Reference values in healthy subjects and in patients with different diseases" Scand J Clin Lab Invest, 1997, 57:529-540.

Jin, H. et al. "Novel analog of atrial natriuretic peptide selective for receptor-A produces increased diuresis and natriuresis in rats" J. Clin. Invest., 1996, 98:969-976.

Kanwal, S. et al. "Intracellular fragments of the natriuretic peptide receptor-C (NPR-C) attenuate dopamine efflux" Endocrinology, 1999, 140(3):1118-1124.

Kaneko, T. et al. "C-type natriuretic peptide (CNP) is the major natriuretic peptide in human cerebrospinal fluid" Brain Res, 1993, 612:104-109.

Kanwal, S. et al. "Intracellular fragments of the natriuretic peptide receptor-C (NPR-C) attenuate dopamine efflux" Endocrinology, 1999, 140(3):1118-1124.

Kojima, M. et al. "Cloning and sequence analysis of cDNA encoding a precursor for rat brain natriuretic peptide" Biochem. Biophys. Res. Commun., 1989, 159(3):1420-1426.

Kelly, R. and Struthers, A. "Are natriuretic peptides clinically useful as markers of heart failure?" Ann. Clin. Biochem., 2001, 38:94-102.

Khurana, M.L. and Pandey, K.N. "Receptor-mediated stimulatory effect of atrial natriuretic factor, brain natriuretic peptide, and C-type natriuretic peptide on testosterone production in purified mouse Leydig cells: Activation of cholesterol side-chain cleavage enzyme" Endocrinology, 1993, 133:2141-2149.

Kiemer, A. and Vollmar, A. "Autocrine regulation of inducible nitric-oxide synthase in macrophages by atrial natriuretic peptide" *J Biol Chem*, 1998, 273:13444-13451.

Kiemer, A. et al. "cGMP-mediated inhibition of TNF-α production by the atrial natriuretic peptide in murine macrophages" *J Immunol*, 2000, 165:175-181.

Kumar, R. et al. "Expression of guanylyl cyclase-A/atrial natriuretic peptide receptor blocks the activation of protein kinse C in vascular smooth muscle cells" *Hypertension*, 1997, 29(part 2):414-421.

Kurihara, M. et al. "Lower number of atrial natriuretic peptide receptors in thymocytes and spleen cells of spontaneously hypertensive rats" *Biochem Biophys Res Commun* 1987, 149:1132-1140.

Liang, F. et al. "Sp1 dependence of natriuretic peptide receptor A gene transcription in rat aortic smooth muscle cells" *Endocrinology*, 1999, 140(4):1695-1701.

Li, Y. et al. "Intrastriatal transplantation of bone marrow nonhematopoietic cells improves functional recovery after stroke in adult mice" *Journal of Cerebral Blood Flow & Metabolism*, 2000, 20:1311-1319.

Li, Y. et al. "Human marrow stromal cell therapy for stroke in rat: Neurotrophins and functional recovery" *Neurology*, 2002, 59:514-523.

Lin, K-F. et al. "Human atrial natriuretic peptide gene delivery reduces blood pressure in hypertensive rats" *Hypertension*, 1995, 26:847-853.

Lin, K-F. et al. "Atrial natriuretic peptide gene delivery attenuates hypertension, cardiac hypertrophy, and renal injury in salt-sensitive rats" *Human Gene Therapy*, 1998, 9:1429-1438.

Lu, D. et al. "Adult bone marrow stromal cells administered intravenously to rats after traumatic brain injury migrate into brain and improve neurological outcome" *Neuroreport*, 2001, 12:559-563.

Mahmood, A. et al. "Treatment of traumatic brain injury in female rats with intravenous administration of bone marrow stromal cells" *Neurosurgery*, 2001, 49:1196-1204.

Mahmood, A. et al. "Intracranial bone marrow transplantation after traumatic brain injury improving functional outcome in adult rats" *Journal of Neurosurgery*, 2001, 94:589-595.

Mahmood, A. et al. "Intracerebral transplantation of marrow stromal cells cultured with neurotrophic factors promotes functional recovery in adult rats subjected to traumatic brain injury" *J Neurotrauma*, 2002, 19:1609-1617.

Maisel, A.S. et al. "Cardiac natriuretic peptides: A proteomic window to cardiac function and clinical management" *Rev. Cardiovasc. Med.*, 2003, 4(suppl 4):S3-S12.

Martin, J. et al. "Modulation by biologic response modifiers of hepatitis C virus antigen-independent cytokine secretion in blood mononuclear cells" *Cytokine*, 1999, 11:267-273.

Matanić, D. et al. "Cytokines in patients with lung cancer" *Scand J Immunol*, 2003, 57:173-178.

Matsukawa, N. et al. "The natriuretic peptide clearance receptor locally modulates the physiological effects of the natriuretic peptide system" *Proc. Natl. Acad. Sci. USA*, 1999, 96:7403-7408.

Mohapatra, S. et al. "Natriuretic peptides and genesis of asthma: An emerging paradigm?" *J Allergy Clin Immunol*, 2004, 114:520-526.

Motohashi, S. et al. "Preserved IFN-α production of circulating Vα24 NKT cells in primary lung cancer patients" *Int J Cancer*, 2002, 102:159-165.

Mueller, C. and Buser, P. "B-type natriuretic peptide (BNP): can it improve our management of patients with congestive heart failure?" *Swiss Med Wkly*, 2002, 132:618-622.

Nakagawa, K. et al. "Plasma concentrations of atrial and brain natriuretic peptides in a case with hypertensive encephalopathy" *Neurol. Res.*, 2002, 24:627-630.

Nakao, N. et al. "Effect of atrial natriuretic peptide on ischemic brain edema: Changes in brain water and electrolytes" *Neurosurgery*, 1990, 27:39-44.

Naruse, S. et al. "Effects of atrial natriuretic peptide on brain oedema: The change of water, sodium, and potassium contents in the brain" *Acta Neurochir Suppl* (Wien), 1990, 51:118-121.

Nazario, B. et al. "Atrial and brain natriuretic peptides stimulate the production and secretion of C-type natriuretic peptide from bovine aortic endothelial cells" *J. Clin. Invest.*, 1995, 95:1151-1157.

Nocera, R. et al. "Novel strategies of neuroprotection against pathologic consequences of stroke in the aged brain" *Society for Neurosci. Abstracts*, 2001, 27(2):2302, Meeting date Nov. 10-15, 2001.

Ogawa, Y. et al. "Molecular cloning of the complementary DNA and gene that encode mouse brain natriuretic peptide and generation of transgenic mice that overexpress the brain natriuretic peptide gene" *J. Clin. Invest.*, 1994, 93(5):1911-1921.

Ohsaki, Y. et al. "Human small cell lung cancer cell lines express functional atrial natriuretic peptide receptors" *Cancer Res*, 1993, 53:3165-3171.

Ohsaki, Y. et al. "Human small cell lung cancer cells produce brain natriuretic peptide" *Oncology*, 1999, 56:155-159.

Ohyama, Y. et al. "Stable expression of natriuretic peptide receptors: Effects of HS-142-1, a non-peptide ANP antagonist" *Biochem. Biophys. Res. Commun.*, 1992, 189(1):336-342.

Pandey, K.N. et al. "Natriuretic peptide receptor-A negatively regulates mitogen-activated protein kinase and proliferation of mesangial cells: Role of cGMP-dependent protein kinase" *Biochem. Biophys. Res. Commun.*, 2000, 271(2):374-379.

Pandey, K.N. et al. "Internalization and trafficking of guanylyl (guanylate) cyclase/natriuretic peptide receptor A is regulated by an acidic tyrosine-based cytoplasmic motif GDAY" *Biochem. J.*, 2005, 388:103-113.

Pandey, K.N. et al. "Ligand-regulated internalization, trafficking, and down-regulation of guanylyl cyclase/atrial natriuretic peptide receptor-A in human embryonic kidney 293 cells" *J. Biol. Chem.*, 2002, 277(7):4618-4627.

Pandey, K.N. et al. "Functional domains and expression of truncated atrial natriuretic peptide receptor-A: The carboxyl-terminal regions direct the receptor internalization and sequestration in COS-7 cells" *Molecular Pharmacology*, 2000, 57:259-267.

Pandey, K.N. "Dynamics of internalization and sequestration of guanylyl cyclase/atrial natriuretic peptide receptor-A" *Can. J. Physiol. Pharmacol.*, 2001, 79(8):631-639.

Pandey, K.N. "Intracellular trafficking and metabolic turnover of ligand-bound guanylyl cyclase/atrial natriuretic peptide receptor-A into subcellular compartments" *Mol. Cell. Biochem.*, 2002, 230(1-2):61-72.

Pikarsky, E. et al. "NF-κB functions as a tumour promoter in inflammation-associated cancer" *Nature*, 2004, 431: 461-466.

Porter, J.G. et al. "Cloning of a cDNA encoding porcine brain natriuretic peptide" *J. Biol. Chem.*, 1989, 264(12):6689-6692.

Prins, B.A. et al. "Atrial natriuretic peptide inhibits mitogen-activated protein kinase through the clearance receptor" *J. Biol. Chem.*, 1996, 271(24):14156-14162.

Quan, H. et al. "Inducible regulation of human brain natriuretic peptide promoter in transgenic mice" *Am. J. Physiol. Heart Circ. Physiol.*, 2001, 280:H368-H376.

Roy, K. et al. "Oral gene delivery with chitosan-DNA nanoparticles generates immunologic protection in a murine model of peanut allergy" *Nat Med*, 1999, 5:387-391.

Roy, R.N. and Flynn, T.G. "Organization of the gene for iso-rANP, a rat B-type natriuretic peptide" *Biochem. Biophys. Res. Commun.*, 1990, 171(1):416-423.

Rouleau, N. et al. "Development of a Non-radioactive Homogenous HTS Platform to Measure the Activity of Guanylate Cyclase", Poster #P10144, Presented at 10th Annual SBS Conference and Exhibition, Orlando, FL, Sep. 11-15, 1004, Perkinelmer Biosignal Inc., Canada.

Rutherford, R. et al. "Identification of renal natriuretic peptide receptor subpopulations by use of the non-peptide antagonist, HS-142-1" *Br. J. Pharmacol.*, 1994, 113:931-939.

Sanchez-Ramos, J.R. "Neural cells derived from adult bone marrow and umbilical cord blood" *J. Neurosci. Res.*, 2002, 69:880-893.

Seidman, C. et al. "Nucleotide sequences of the human and mouse atrial natriuretic factor genes" *Science*, 1984, 226:1206-1209.

Seilhamer, J.J. et al. "Human and canine gene homologs of porcine brain natriuretic peptide" *Biochem. Biophys. Res. Commun.*, 1989, 165(2):650-658.

Sekiguchi, T. et al. "Molecular cloning of natriuretic peptide receptor A from bullfrog (*Rana catesbeiana*) brain and its functional expression" *Gene*, 2001, 273:251-257.

Sharma, G.D. et al. "Expression of atrial natriuretic peptide receptor-A antagonizes the mitogen-activated protein kinases (Erk2 and P38$^{MAPK}$) in cultured human vascular smooth muscle cells" *Mol. Cell. Biochem.*, 2002, 233(1-2):pp. 165-173.

Shi, S-J. et al. "Natriuretic peptide receptor A mediates renal sodium excretory responses to blood volume expansion" *Am. J. Physiol. Renal Physiol.*, 2003, 285:F694-F702.

Shimizu, K. et al. "Ectopic atrial natriuretic peptide production in small cell lung cancer with the syndrome of inappropriate antidiuretic hormone secretion" *Cancer* 1991, 68:2284-2288.

Silberbach, M. and Roberts Jr., C. "Natriuretic peptide signaling molecular and cellular pathways to growth regulation" *Cell Signal*, 2001, 13:221-231.

Simkins, J. "Nesiritide (Natrecor®) for Decompensated CHF" in The University of Montana's School of Pharmacy and Allied Health Sciences Drug Information Service, Apr. 2002, vol. 6 No. 4.

Song, S. et al. "Nerve growth factor and retinoic acid induce development of neuronal cells from bone marrow stromal cells of both young and old mice" *Society for Neurosci. Abstracts*, 2001, 27(1):940, Meeting date Nov. 10-15, 2001.

Song, S. et al. "Expression of brain natriuretic peptide by human bone marrow stromal cells" *Society for Neurosci. Abstracts*, 2002, Abstract No. 824.3, Meeting date Nov. 2-7, 2002.

Song, S. and Sanchez-Ramos, J. "Preparation of Neural Progenitors from Bone Marrow and Umbilical Cord Blood" in Protocols for Neural Stem Cell Methods, Zigova, T. et al., Eds., 2002, pp. 79-88.

Song, S. et al. "Expression of brain natriuretic peptide by human bone marrow stromal cells" *Experimental Neurology*, 2004, 185:191-197.

Steinhelper, M.E. "Structure, expression, and genomic mapping of the mouse natriuretic peptide type-B gene" *Circ. Res.*, 1993, 72(5):984-992.

Sudoh, T. et al. "Brain natriuretic peptide-32: N-terminal six amino acid extended form of brain natriuretic peptide identified in porcine brain" *Biochem Biophys Res Commun*, 1988, 155:726-732.

Suenobu, N. et al. "Natriuretic peptides and nitric oxide induce endothelial apoptosis via a cGMP-dependent mechanism" *Arterioscler Thromb Vasc Biol.*, 1999, 19:140-146.

Surić-Lambić, L. et al. "Vasoactive natriuretic peptides and kidney" *Facta Universitatis: Medicine and Biology*, 1998, 5(1):6-11.

True, D. et al. "Comparison of Kinase Assay Technologies for High Throughput Screening" poster presented at Society for Biomolecular Screening (SBS), 8$^{th}$ Annual Conference, Sep. 22-26, 2002.

Vesely, B.A. et al. "Four peptides decrease the number of human pancreatic adenocarcinoma cells" *Eur. J. Clin. Invest.*, 2003, 33:998-1005.

Vesely, D.L. "Atrial natriuretic peptides in pathophysiological diseases" *Cardiovascular Res*, 2001, 51:647-658.

Vlasuk, G.P. et al. "Structure and analysis of the bovine atrial natriuretic peptide precursor gene" *Biochem. Biophys. Res. Commun.*, 1986, 136(1):396-403.

Wang, W. et al. "AlbuBNP, a recombinant B-type natriuretic peptide and human serum albumin fusion hormone, as a long-term therapy of congestive heart failure" *Pharm. Res.*, 2004, 21(11):2105-2111.

Zivin, R.A. et al. "Molecular cloning and characterization of DNA sequences encoding rat and human atrial natriuretic factors" *Proc. Natl. Acad. Sci. USA*, 1984, 81(20):6325-6329.

Boiteau, R. et al. "Increase in atrial natriuretic factor (ANF) in acute severe asthma (ASA)" *Am Rev Res Dis.*, 1988, 137:A484.

Chanez, P. et al. "Atrial natriuretic factor (ANF) is a potent bronchodilator in asthma" *J. Allergy Clin. Immunol.*, 1990, 86:321-324.

Greenberg, B.D. et al. "Nucleotide sequence of the gene encoding human atrial natriuretic factor precursor" *Nature*, 1984, 312(5995):656-658.

Hamet, P. et al. "Aspects physiologiques et physiopathologiques du facteur natriuretique auriculaire" *Nephrologie*, 1987, 8:7-12, abstract.

Hulks, G. et al. "Effect of atrial natriuretic factor on bronchomotor tone in the normal human airway" *Clin Sci*, 1990, 79:51-55.

Hulks, G. et al. "Inhaled atrial natriuretic peptide and asthmatic airways" *Br. Med J*, 1992, 304:1156.

Hulks, G. et al. High dose inhaled atrial natriuretic peptide is a bronchodilator in asthmatic subjects *Eur Respir J.*, 1994, 7:1593-1597.

Ishii, Y. et al. "Effects of atrial natriuretic peptide on Type II alveolar epithelial cells of the rat lung. Autoradiographic and morphometric studies" *J Anat.*, 1989, 166:85-95.

Kumar, M. et al. "Intranasal IFN-γ gene transfer protects BALB/c mice against respiratory syncytial virus infection" *Vaccine*, 2000; 18:558-567.

Kumar, M et al. "Atrial natriuretic peptide gene transfer by means of intranasal administration attenuates airway reactivity in a mouse model of allergic sensitization" *J Allergy Clin Immunol.*, 2002, 110:879-882.

Louzier, V. et al. "Adenovirus-mediated atrial natriuretic protein expression in the lung protects rats from hypoxia-induced pulmonary hypertension" *Hum Gene Ther*, 2001, 12:503-513.

Matsuse, H. et al. "Recurrent Respiratory Syncytial Virus Infections in Allergen-Sensitized Mice Lead to Persistent Airway Inflammation and Hyperresponsiveness" *The Journal of Immunology*, 2000, 164:6583-6592.

Needleman, P. et al. "Atriopeptin: a cardiac hormone intimately involved in fluid, electrolyte, and blood-pressure homeostasis" *N Engl J Med*, 1986, 314:828-834.

Ohbayashi, H. et al. "Compared effects of natriuretic peptides on ovalbumin-induced asthmatic model" *Eur. J. Pharmac.*, 1998, 346:55-64.

Seidman, C.E. et al. "The structure of rat preproatrial natriuretic factor as defined by a complementary DNA clone" *Science*, 1984, 225:324-326.

Winquist, R. et al. "Atrial natriuretic factor elicits an endothelium-independent relaxation and activates particulate guanylate cyclase in vascular smooth muscle" *Proc. Natl. Acad. Sci. USA*, 1984, 81:7661-7664.

"Atrial natriuretic factor receptor A", MeSH results, accessed http://www.ncbi.nlm.nih.gov/mesh on Dec. 3, 2009, pp. 1-2.

Ahn, K.S. et al. "Simvastatin Potentiates TNF-a-Induced Apoptosis through the Down-Regulation of NF-κB-Dependent Antiapoptotic Gene Products: Role of IκBα Kinase and TGF-β-Activated Kinase-1" *Journal of Immunology*, 2007, 178:2507-2516.

Allen, T.M. et al. "Large unilamellar liposomes with low uptake into the reticuloendothelial system" *FEBS Letters*, 1987, 223:42-46.

Arenberg, D. "Chemokines in the Biology of Lung Cancer" *Journal of Thoracic Oncology*, 2006, 1(4):287-288.

Ashworth, T. et al. "Cutting Edge: TFII-I Controls B Cell Proliferation via Regulating NF-κB" *Journal of Immunology*, 2007, 178:2631-2635.

Baldini, P.M. et al. "Decrease of polyamine levels and enhancement of transglutaminase activity in selective reduction of B16-F10 melanoma cell proliferation induced by atrial natriuretic peptide" *Melanoma Research*, 2006, 16:501-507.

Bass, B.L. "RNA interference: The short answer" *Nature*, 2001, 411:428-429.

Bernstein, E. et al. "The rest is silence" *RNA*, 2001, 7:1509-1521.

Bernstein, E. et al. "Role for a bidentate ribonuclease in the initiation step of RNA interference" *Nature*, Jan. 2001, 409:363-366.

Cane, A. et al. "The Endogenous Oxindoles 5-Hydroxyoxindole and Isatin Are Antiproliferative and Proapoptotic" *Biochemical and Biophysical Research Communications*, 2000, 276:379-384.

Carthew, R.W. "Gene silencing by double-stranded RNA" *Current Opinion in Cell Biology*, 2001, 13:244-248.

Chin, L. et al. "Malignant melanoma: modern black plague and genetic black box" *Genes & Development*, 1998, 12(22):3467-3481.

Chiu, Y.L. et al. "RNAi in Human Cells: Basic Structural and Functional Features of Small Interfering RNA" *Molecular Cell*, Sep. 2002, 10(3):549-561.

Clark, A.R. "Mechanisms of steroid action and resistance in inflammation: MAP kinase phosphatase 1: a novel mediator of biological effects of glucocorticoids" *Journal of Indocrinology*, 2003, 178:5-12.

Clemens, J.C. et al. "Use of double-stranded RNA interference in Drosophila cell lines to dissect signal transduction pathways" *PNAS*, 2000, 97:6499-6503.

Clusel, C. et al. "Ex vivo regulation of specific gene expression by nanomolar concentration of double-stranded dumbbell oligonucleotides" *Nucleic Acids Research* 1993, 21(15):3405-3411.

Collins, F.S. et al. "Generation and initial analysis of more than 15,000 full-length human and mouse cDNA sequences" *Proc Natl Acad Sci*, 2002:99:16899-16903.

Dorn, G. et al. "siRNA relieves chronic neuropathic pain" *Nucleic Acids Research*, 2004, 32:e49.

Eichelbaum, E.J. et al. "Cardiac and kidney hormones cure up to 86% of human small-cell lung cancers in mice" *Eur J Clin Invest*, 2008, 38(8):562-570.

Elbashir, S.M. et al. "Duplexes of 21-nucleotide RNAs mediate RNA interference in cultured mammalian cells" *Nature*, May 24, 2001, 411:494-498.

Elbashir, S.M. et al. "RNA interference is mediated by 21- and 22-nucleotide RNAs" *Genes and Development*, 2001, 15:188-200.

Fattal, E. et al. "Biodegradable polyalkylcyanoacrylate nanoparticles for the delivery of oligonucleotides" *Journal of Controlled Release*, 1998, 53:137-143.

Filomeni, G. et al. "Pro-apoptotic Activity of Novel Isatin-Schiff Base Copper(II) Complexes Depends on Oxidative Stress Induction and Organelle-selective Damage" *Journal of Biological Chemistry*, 2007, 282(16):12010-12021.

Fiscus, R.R. "Involvement of Cyclic GMP and Protein Kinase G in the Regulation of Apoptosis and Survival in Neural Cells" *NeuroSignals*, 2002, 11:175-190.

Forssmann, W.G. et al. "The renal urodilatin system: clinical implications" *Cardiovascular Research*, 2001, 51:450-462.

Gabellini, C. et al. "Involvement of RB gene family in tumor angiogenesis" *Oncogene*, 2006, 25:5326-5332.

Glover, V. et al. "Isatin: Identity with the Purified Endogenous Monamine Oxidase Inhibitor Tribulin" *Journal of Neurochemistry*, 1988, 51(2):656-659.

Gopalakrishnan, M. et al. "Stable expression and pharmacological properties of the human $a_7$ nicotinic acetylcholine receptor" *European Journal of Pharmacology: Molecular Pharmacology Section*, 1995, 290(3):237-246.

Halder, J. et al. "Focal Adhesion Kinase Targeting Using In vivo Short Interfering RNA Delivery in Neutral Liposomes for Ovarian Carcinoma Therapy" *Clinical Cancer Research*, 2006, 12:4916-4924.

Hammond, S.M. et al. "Argonaute2, a Link Between Genetic and Biochemical Analyses of RNAi" *Science*, Aug. 10, 2001, 293:1146-1150.

Harborth, J. et al. "Identification of essential genes in cultured mammalian cells using small interfering RNAs" *Journal of Cell Science*, 2001, 114:4457-4565.

Haseloff, J. et al. "Simple RNA enzymes with new and highly specific endoribonuclease activities" *Nature*, 1988, 334(6183):585-591.

Helene, C. et al. "Control of Gene Expression by Triple Helix-Forming Oligonucleotides: The Antigene Strategy" *Annals of the New York Academy of Sciences*, 1992, 660(1):27-36.

Hellerman, G. et al. "Mechanism of bronchoprotective effects of a novel natriuretic hormone peptide" *Journal of Allergy and Clinical Immunology*, 2004, 113:79-85.

Hirata, Y. "Heterologus Down-Regulation of Vascular Atrial Natriuretic Peptide Receptors by Phorbol Esters" *Biochemical and Biophysical Research Communications*, May 16, 1988, 152(3):1097-1103.

Ho, R.J.Y. et al. "Target-sensitive immunoliposomes: preparation and characterization" *Biochemistry*, 1986, 25:5500-5506.

Ho, R.J.Y. et al. "Interactions of Target-sensitive Immunoliposomes with Herpes Simplex Virus" *The Journal of Biological Chemistry*, 1987, 262(29):13979-13984.

Ho, R.J.Y. et al. "Target-sensitive immunoliposomes as an efficient drug carrier for antiviral activity" *The Journal of Biological Chemistry*, 1987, 262(29):13973-13978.

Howard, K.A. et al. "RNA Interference in Vivo and in Vitro Using a Chitosan/siRNA Nanoparticle System" *Molecular Therapy*, 2006, 14(4):476-484.

Hutvagner, G. et al. "RNAi: nature abhors a double-strand" *Current Opinion in Genetics & Development*, 2002, 12:225-232.

Igosheva, N. et al. "Isatin, an endogenous monamine oxidase inhibitor, triggers a dose- and time-dependent switch from apoptosis to necrosis in human neuroblastoma cells" *Neurochemistry International*, 2005, 47(3):216-224.

Inoue, J.I. et al. "NFκB activation in development and progression of cancer" *Cancer Science*, 2007, 98:268-274.

Ivanova, K. et al. "Differential Expression of Functional Guanylyl Cyclases in Melanocytes: Absence of Nitric-Oxide-Sensitive Isoform in Metastatic Cells" *Journal of Investigative Dermatology*, Mar. 2001, 116(3):409-416.

Jacque, J.M. et al. "Modulation of HIV-1 replication by RNA interference" *Nature*, Jul. 25, 2002, 418(6896):435-438.

Karin, M. "Mitogen activated protein kinases as targets for development of novel anti-inflammatory drugs" *Annals of the Rheumatic Diseases*, 2004, 63(Suppl. 2):ii62-ii64.

Katas, H. et al. "Development and characterisation of chitosan nanoparticles for siRNA delivery" *Journal of Controlled Release*, 2006, 115(2):216-225.

Kim, J.W. et al. "Effect of phosphorylation and S—S bond-induced dimerization on DNA binding and transcriptional activation by C/EBPβ" *Proc Natl Acad Sci USA*, 2007, 104:1913-1918.

Kisielow, M. et al. "Isoform-specific knockdown and expression of adaptor protein ShcA using small interfering RNA" *Biochem J.*, 2002, 363(1):1-5.

Klibanov, A.L. et al. "Amphipathic polyethyleneglycols effectively prolong the circulation time of liposomes" *FEBS Letters*, 1990, 268:235-237.

Knaapen, A.M. et al. "Inhaled particles and lung cancer. Part A: Mechanisms" *International Journal of Cancer*, 2004, 109:799-809.

Kong, X. et al. "Mice Deficient in Atrial Natriuretic Peptide Receptor A (NPRA) Exhibit Decreased Lung Inflammation: Implication of NPRA Signaling in Asthma Pathogenesis" *Journal of Allergy and Clinical Immunology*, Jan. 2007, 119(1):5127, abstract 501.

Kong, X. et al. "Natriuretic Peptide Receptor A as a Novel Anticancer Agent" *Cancer Research*, Jan. 2008, 68(1):249-256.

Lambert, G. et al. Nanoparticulate systems for the delivery of antisense oligonucleotides *Advanced Drug Delivery Reviews*, Mar. 2001, 47:99-112.

Landen, C.N. et al. "Intraperitoneal Delivery of Liposomal siRNA for Therapy of Advanced Ovarian Cancer" *Cancer Biology & Therapy*, 2006, 5(12):1708-1713.

Lee, N.S. et al. "Expression of small interfering RNAs targeted against HIV-1 *rev* transcripts in human cells" *Nature Biotechnology*, May 2002, 20:500-505.

Lenz, A. et al. "Cardiac Hormones Eliminate some Human Squamous Lung Carcinomas in Athymic Mice" *European Journal of Clinical Investigation*, 2010 in press, p. 1-13.

Levin, E.R. et al. "Mechanisms of Disease: Natriuretic Peptides" *New England Journal of Medicine*, 1998, 339:321-328.

Lieberman, J. et al. "Interfering with disease: opportunities and roadblocks to harnessing RNA interference" *Trends in Molecular Medicine*, Sep. 2003, 9(9):397-403.

Liu, Y. et al. "Discovery of Inhibitors that Elucidate the Role of UCH-L1 Activity in the H1299 Lung Cancer Cell Line" *Chemistry & Biology*, 2003, 10(9):837-846.

Liu, X. et al. "The influence of polymeric properties on chitosan/siRNA nanoparticle formulation and gene silencing" *Biomaterials*, 2007, 28:1280-1288.

Mailand, N. et al. "Deregulated human Cdc14a phosphatase disrupts centrosome separation and chromosome segregation" *Nature Cell Biology*, 2002, 4(4):317-322.

Martey, C.A. et al. "Cigarette smoke induces cyclooxygenase-2 and microsomal prostaglandin $E_2$ synthase in human lung fibroblasts: implications for lung inflammation and cancer" *Am J Physiol Lung Cell Mol Physiol*, 2004, 287:L981-991.

Massion, P.P. et al. "The molecular basis of lung cancer: molecular abnormalities and therapeutic implications" *Respiratory Research*, 2003, 4(1):12.1-12.15.

Matzke, M. et al. "RNA: Guiding Gene Silencing" *Science*, 2001, 293:1080-1083.

McCaffrey, A.P. et al. "Gene expression: RNA interference in adult mice" *Nature*, Jul. 2002, 418(6893):38-39.

Misono, K.S. "Natriuretic peptide receptor: Structure and signaling" *Molecular and Cellular Biochemistry*, 2002, 230:49-60.

Mizuguchi, M. et al. "Bronchoprotective effects of atrial natriuretic peptide against propanolol-induced bronchoconstriction after allergic reaction in guinea pigs" *Clinical and Experimental Allergy*, 2000, 30:439-444.

Mohapatra, S.S. et al. "Role of natriuretic peptide signaling in modulating asthma and inflammation" *Can J Physiol Pharmacol*, 2007, 85:754-759.

Morita, R. et al. "Atrial Natriuretic Peptide Polarizes Human Dendritic Cells Toward a Th2-Promoting Phenotype Through Its Receptor Guanylyl Cyclase-Coupled Receptor A1" *The Journal of Immunology*, 2003, 170:5869-5875.

Nafee, N. et al. "Chitosan-coated PLGA nanoparticles for DNA/RNA delivery: effect of the formulation parameters on complexation and transfection of antisense oligonucleotides" *Nanomedicine: Nanotechnology, Biology, and Medicine*, 2007, 3(3):173-183.

Novina, C.D. et al. "The RNAi revolution" *Nature*, 2004, 430:161-164.

Nuglozeh, E. et al. "Gene expression of natriuretic peptide receptors in rats with DOCA-salt hypertension" *Am J Physiol Cell Physiol*, 1997, 273:1427-1434.

Nykanen, A. et al. "ATP Requirements and small Interfering RNA Structure" *Cell*, Nov. 2001, 107:300-321.

Nyormoi, O. et al. "Transcriptional regulation of metastasis-related genes in human melanoma" *Clinical and Experimental Metastasis*, 2003, 20:251-263.

Ogata, A. et al. "Isatin, an endogenous MAO inhibitor, improves bradykinesia and dopamine levels in a rat model of Parkinson's disease induced by Japanese encephalitis virus" *Journal of the Neurological Sciences*, 2003, 206(1):79-83.

Oka, D. et al. "Sesquiterpene lactone parthenolide suppresses tumor growth in a xenograft model of renal cell carcinoma by inhibiting the activation of NF-κB" *International Journal of Cancer*, 2007, 120:2576-2581.

Oliveira, A.M. et al. "Tumor Suppressor Genes in Breast Cancer: The Gatekeepers and the Caretakers" *American Society for Clinical Pathology*, 2005, 124:S16-S28.

Paddison, P.J. et al. "Short hairpin RNAs (shRNAs) induce sequence-specific silencing in mammalian cells" *Genes & Development*, 2002, 15:948-958.

Palaparti, A. et al. "Inhibition of atrial natriuretic peptide (ANP) C receptor expression by antisense oligodeoxynucleotides in A10 vascular smoth-muscle cells is associated with attenuation of ANP-C-receptor-mediated inhibition of adenylyl cyclase" *Biochem J*, 2000, 346:313-320.

Pandey, K.N. et al. "Molecular Cloning and Expression of Murine Guanylate Cyclase/Atrial Natriuretic Factor Receptor cDNA" *The Journal of Biological Chemistry*, Jul. 25, 1990, 265(21):12342-12348.

Paul, C.P. et al. "Effective expression of small interfering RNA in human cells" *Nature Biotechnology*, May 2002, 20:505-508.

Pedram, A. et al. "Natriuretic Peptides Inhibit G Protein Activation. Mediation Through Cross-Talk Between Cyclic GMP-Dependent Protein Kinase and Regulators of G Protein-Signaling Proteins" *J. Biol. Chem.*, 2000, 275:7365-7372.

Plasterk, R.H.A., "RNA Silencing: The Genome's Immune System" *Science*, 2002, 296:1263-1265.

Popp, F.D. "Synthesis of Potential Antineoplastic Agents. XX. Compounds Related to the 3-o-Nitrophenylhydrazone of Isatin" *Journal of Medicinal Chemistry*, 1969, 12(1):182-184.

Reich, S.J. et al. "Small interfering RNA (siRNA) targeting VEGF effectively inhibits ocular neovascularization in a mouse model" *Molecular Vision*, 2003, 9:210-216.

Saccani, A. et al. "p50 Nuclear Factor-κB Overexpression in Tumor-Associated Macrophages Inhibits M1 Inflammatory Responses and Antitumor Resistance" *Cancer Research*, Dec. 2006, 66(23)11432-11440.

Scadden, A.D.J. "RNAi is antagonized by A→I hyper-editing" *EMBO Reports*, 2001, 11(2):1107-1111.

Scherr, M. et al. "Inhibition of GM-CSF Receptor Function by Stable RNA Interference in a NOD/SCID Mouse Hematopoietic Stem Cell Transplantation Model" *Oligonucleotides*, Oct. 2003, 13(5): 353-363.

Schipper, N.G.M. et al. "Chitosans as Absorption Enhancers for Poorly Absorbable Drugs. 1: Influence of Molecular Weight and Degree of Acetylation on Drug Transport Across Human Intestinal Epithelial (Caco-2) Cells" *Pharmaceutical Research*, 1996, 13(11):1686-1692.

Schmidt, D. et al. "Critical role for NFκB-induced JunB in VEGF regulation and tumor angiogenesis" *The EMBO Journal*, 2007, 26:710-729.

Schwartz, A.G. et al. "The molecular epidemiology of lung cancer" *Carcinogenesis*, 2007, 28:507-518.

Sharp, P.A. "RNAi and double-strand RNA" *Genes & Dev.*, 1999, 13:139-141.

Sharp, P.A. "RNA interference—2001" *Genes & Development*, 2001, 15:485-490.

Song, E. et al. "RNA interference targeting Fas protects mice from fulminant hepatitis" *Nature Medicine*, 2003, 9(3):347-351.

Soutschek, J. et al. "Therapeutic silencing of an endogenous gene by systemic administration of modified siRNAs" *Nature*, Nov. 2004, 432:173-178.

Sumpter, W.C. "The Chemistry of Isatin" *Chemical Reviews*, 1944, 34(3):393-434.

Svoboda, P. et al. "Selective reduction of dormant maternal mRNAs in mouse oocytes by RNA interference" *Development*, Oct. 2000, 127:4147-4156.

Tolentino, M.J. et al. "Intravitreal Injection of Vascular Endothelial Growth Factor Small Interfering RNA Inhibits Growth and Leakage in a Nonhuman Primate, Laser-Induced Model of Choroidal Neovascularization" *Retina*, 2004, 24:132-138.

Tremblay, J. et al. "Biochemistry and physiology of the natriuretic peptide receptor guanylyl cyclases" *Molecular and Cellular Biochemistry*, 2002, 230:31-47.

Tunny, T.J. et al. "Association of Restriction Fragment Length Polymorphism at the Atrial Natriuretic Peptide Gene Locus with Aldosterone Responsiveness to Angiotensin in Aldosterone-Producing Adenoma" *Biochemical and Biophysical Research Communications*, 1994, 204:1312-1317.

Tuschl, T. et al. "Targeted mRNA degradation by double-stranded RNA in vitro" *Genes & Development*, Dec. 1999, 13:3191-3197.

Tuschl, T. "RNA Interference and Small Interfering RNAs" *Chembiochem*, 2001, 2:239-245.

Tuschl, T. "Expanding small RNA interference" *Nature Biotechnology*, 2002, 20:446-448.

Vellaichamy, E. et al. "Reduced cGMP signaling activates NF-κB in hypertrophied hearts of mice lacking natriuretic peptide receptor-A" *Biochemical and Biophysical Research Communications*, 2005, 327:106-111.

Verma, I.M. et al. "Gene Therapy—promises, problems and prospects" *Nature*, 1997, 389:239-242.

Vesely, D.L. et al. "Atrial natriuretic peptides negatively and positively modulate circulating endothelin in humans" *Metabolism*, 1996, 45:315-319.

Vesely, D.L. et al. "Vessel dilator, long acting natriuretic peptide, and kaliuretic peptide increase circulating prostaglandin $E_2$" *Life Sciences*, 2000, 66:095-913.

Vesely, D.L. et al. "Atrial Natriuretic Hormone, Vessel Dilator, Long-Acting Natriuretic Hormone, and Kaliuretic Hormone Decrease the Circulating Concentrations of CRH, Corticotropin, and Cortisol" *J Clin Endocrinol Metab*, 2001, 86:4244-4249.

Vesely, D.L. et al. "Atrial Natriuretic Hormone, Vessel Dilator, Long Acting Natriuretic Hormone, and Kaliuretic Hormone Decrease Circulating Prolactin Concentrations" *Norm Metab Res*, 2002, 34:245-249.

Vesely, D.L. "Atrial Natriuretic Peptide Prohormone Gene Expression: Hormones and Diseases That Upregulate its Expression" *IUBMB Life*, 2002, 53(3):153-159.

Vesely, D.L. et al. "Four Cardiac Hormones Eliminate up to Two-Thirds of Human Breast Cancers in Athymic Mice" *In Vivo*, 2007, 21:973-978.

Vesely, D.L. et al. "Elimination of Up to 80% of Human Pancreatic Adenocarcinomas in Athymic Mice by Cardiac Hormones" *In Vivo*, 2007, 21:445-452.

Vesely, B.A. et al. "Four peptide hormones decrease the number of human breast adenocarcinoma cells" *European Journal of Clinical Investigation*, 2005, 35:60-69.

Vesely, B.A. et al. "Four Cardiac Hormones Cause Cell Death of Melanoma Cells and Inhibit Their DNA Synthesis" *Am J Med Sci*, 2007, 334(5):342-349.

Vesely, D.L. "Atrial natriuretic peptides: anticancer agents" *J Investig Med.*, 2005, 53(7):360-365.

Vilimas, T. et al. "Targeting the NF-κB signaling pathway in Notch1-induced T-cell leukemia" *Nature Medicine*, 2007, 13:70-77.

Vine, K.L. et al. "In vitro cytotoxicity evaluation of some substituted isatin derivatives" *Bioorganic & Medicinal Chemistry*, 2007, 15(2):931-938.

Wang, X. et al. "siRNA Targeting the Natriuretic Peptide Receptor-A Prevents Airway Inflammation in a Mouse Model of Allergic Asthma" *Journal of Allergy and Clinical Immunology*, Jan. 2007, 119(1):S131, abstract 515.

Wang, X. et al. "Modulation of lung inflammation by vessel dilator in a mouse model of allergic asthma" *Respiratory Research*, Jul. 2009, 10(66):1-8.

Wang, X. et al. "Prevention of airway inflammation with topical cream containing imiquimod and small interfering RNA for natriuretic peptide receptor" *Genetic Vaccines and Therapy*, Feb. 2008, 6(7):1-9.

Woodle, M.C. et al. "Sterically stabilized liposomes" *Biochimica et Biophysica Acta: Reviews on Biomembranes*, 1992, 1113:171-199.

Xia, H. et al. "siRNa-mediated gene silencing in vitro and in vivo" *Nature Biotechnology*, Oct. 2002, 20(10)1006-1010.

Yu, J.Y. et al. "RNA interference by expression of short-interfering RNAs and hairpin RNAs in mammalian cells" *PNAS USA*, Apr. 2002, 99(9):6047-6052.

Yuhas, J.M. et al. "Specific and Nonspecific Stimulation of Resistance to the Growth and Metastasis of the Line 1 Lung Carcinoma" *Cancer Research*, 1975, 35:242-244.

Zamore, P.D. "Ancient Pathways Programmed by Small RNAs" *Science*, 2002, 296(5571):1265-1269.

Zamore, P.D. "RNA interference: listening to the sound of silence" *Nature Structural Biology*, Sep. 2001, 8(9):746-750.

Zamore, P.D. et al. "RNAi: Double-Stranded RNA Directs the ATP-Dependent Cleavage of mRNA at 21-23 Nucleotide Intervals" *Cell*, Mar. 31, 2000, 101(1):25-33.

Zhang, X. et al. "Small Interfering RNA Targeting Heme Oxygenase-1 Enhances Ischemia-Reperfusion-induced Lung Apoptosis" *The Journal of Biological Chemistry*, Mar. 2004, 279(11):10677-10684.

Zeng, Y. et al. "Both Natural and Designed Micro RNAs Can Inhibit the Expression of Cognate mRNAs When Expressed in Human Cells" *Molecular Cell*, Jun. 2002, 9:1327-1333.

Zimmerman, T.S. et al. "RNAi-mediated gene silencing in non-human primates" *Nature*, May 2006, 441:111-114.

Abadi, A.H. et al. "Synthesis of 3-substituted-2-oxoindole analogues and their evaluation ans kinase inhibitors, anticancer and antiangiogenic agents" *European Journal of Medicinal Chemistry*, 2006, 41(3):296-305.

Office Action dated Aug. 9, 2007 in U.S. Appl. No. 11/059,814, filed Feb. 17, 2005.

Office Action dated Apr. 25, 2008 in U.S. Appl. No. 11/059,814, filed Feb. 17, 2005.

Advisory Action dated Oct. 15, 2008 in U.S. Appl. No. 11/059,814, filed Feb. 17, 2005.

Office Action dated Sep. 2, 2009 in U.S. Appl. No. 11/799,225, filed Apr. 30, 2007.

Office Action dated Apr. 1, 2010 in U.S. Appl. No. 11/799,225, filed Apr. 30, 2007.

Office Action dated Aug. 20, 2010 in U.S. Appl. No. 11/799,225, filed Apr. 30, 2007.

Office Action dated Jun. 1, 2009 in U.S. Appl. No. 11/998,792, filed Nov. 30, 2007.

Office Action dated Dec. 11, 2009 in U.S. Appl. No. 11/998,792, filed Nov. 30, 2007.

Office Action dated May 18, 2010 in U.S. Appl. No. 11/998,792, filed Nov. 30, 2007.

Office Action dated Oct. 13, 2010 in U.S. Appl. No. 11/998,792, filed Nov. 30, 2007.

Benson, J.D. et al. "Validating cancer drug targets" *Nature*, May 2006, 441:451-456.

Brafford, P. et al, "Gene expression profiling of melanoma cells—searching the haystack" *Journal of Translational Medicine*, 2005, 3:2, pp. 1-2.

Carr, K.M. et al. "Gene-expression profiling in human cutaneous melanoma" *Oncogene*, 2003, 22:3076-3080.

Chen, J.H. "Application of cationic polymer vector for gene delivery systems" Yao Xue Xue Bao, Apr. 2003, 38(4):316-20, abstract.

Chengalvala, M.V. et al. "Gene Expression Profiling and its Practice in Drug Development" *Current Genomics*, 2007, 8(4):262-270.

Chin, L. et al. "Malignant melanoma: genetics and therapeutics in the genomic era" *Genes & Development*, 2006, 20:2149-2182.

De Wit, N.J.W. et al. "Analysis of differential gene expression in human melanocytic tumour lesions by custom made oligonucleotide arrays" *British Journal of Cancer*, 2005, 92:2249-2261.

Fluge, T. et al. "Bronchodilation using combined urodilatin—albuterol administration in asthma: a randomized, double-blind, placebo-controlled trial" *European Journal of Medical Research*, 1999, 4(10):411-415.

Gogas, H. et al. "Biomarkers in melanoma" *Annals of Oncology*, Aug. 2009, 20(Supplement 6):vi8-vi13.

Haberman, A.B, "Strategies to Move Beyond Target Validation" *Genetic Engineering News*, Dec. 2005, 25(21):36.

Hulks, G. et al. "Bronchodilator effect of atrial natriuretic peptide in asthma" *Br Med J*, Oct. 28, 1989, 299:1081-1082.

Levy, J.A. et al. "Inactivation of Murine RNA Tumor Viruses by Isatin Beta-Thiosemicarbazone" *Virology*, Oct. 15, 1976, 74(2):426-431.

Lobbezoo, M.W. et al. "Signal Transduction Modulators for Cancer Therapy: From Promise to Practice?" *The Oncologist*, 2003, 8:210-213.

Martinez, S.R. et al. "Molecular Markers in Malignant Cutaneous Melanoma: Gift Horse or One-Trick Pony?" *Journal of Cellular Biochemistry*, 2005, 96:473-483.

Rahmanto, Y.S. et al. "Identification of distinct changes in gene expression after modulation of melanoma tumor antigen p97 (melanotransferrin) in multiple models in vitro and in vivo" *Carcinogenesis*, 2007, 28(10):2172-2183.

Schwab, G. et al. "An approach for new anticancer drugs: Oncogene-targeted antisense DNA" *Ann Oncol*, 1994, 5(Supplement 4):S55-S58.

Schwarze, J. et al. "Respiratory Syncytial Virus Infection Results in Airway Hyperresponsiveness and Enhanced Airway Sensitization to Allergen" *J Clin Invest*, 1997, 99:226-233.

Seftor, E.A. et al. "Expression of multiple molecular phenotypes by aggressive melanoma tumor cells: role in vasculogenic mimicry" *Critical Reviews in Oncology/Hematology*, 2002, 44:17-27.

Skubitz, A.P.N. et al. "Differential gene expression identifies subgroups of ovarian carcinoma" *Translational Research*, Nov. 2006, 148(5):223-248.

Sprenger, H. et al. "The lack of receptors for atrial natriuretic peptides on human monocytes prevents a rise of cGMP and induction of tumor necrosis factor-alpha synthesis" *Immunobiology*, Sep. 1991, 183(1-2):94-101.

Sun, Y. et al. "Atrial Natriuretic Peptide and Long Acting Natriuretic Peptide Inhibit ERK 1/2 in Prostate Cancer Cells" *Anticancer Research*, 2006, 26:4143-4148.

Sun, Y. et al. "Vessel Dilator and Kaliuretic Peptide Inhibit ERK 1/2 Activation in Human Prostate Cancer Cells" *Anticancer Research*, 2006, 26:3217-3222.

Vesely, D.L. et al. "The N-Terminus of the Atrial Natriuretic Factor Prohormone in the Pleural Fluid of Congestive Heart Failure Patients" *Chest*, 1990, 97(6)1295-1298.

Vesely, D.L. "Aprotinin blocks the binding of pro atrial natriuretic peptides 1 to 30, 31 to 67, and 99-126 to human placental membranes" *Am J Obstet Gynecol*, 1991, 165(3)567-573.

Vesely, D.L. "Atrial Natriuretic Hormones Originating from the N-Terminus of the Atrial Natriuretic Factor Prohormone" *Clin Exp Pharmacol Physiol*, 1995, 22(2):108-114.

Vesely, D.L. et al. "Long-Acting Natriuretic Peptide, Vessel Dilator, and Kaliuretic Peptide Enhance the Urinary Excretion Rate of $\beta_2$-Microglobulin" *Metabolism*, Dec. 2000, 49(12):1592-1597.

Vita, M. et al. "The Myc oncoprotein as a therapeutic target for human cancer" *Seminars in Cancer Biology*, 2006, 16:318-330.

Winnepennickx, V. et al. "Gene Expression Profiling of Primary Cutaneous Melanoma and Clinical Outcome" *Journal of the National Cancer Institute*, Apr. 5, 2006, 98(7):472-482.

Wong, H.H. et al. "Pancreatic cancer: molecular pathogenesis and new therapeutic targets" *Nat Rev Gastroenterol Hepatol*, 2009, 6:412-422.

Yang, J. et al. "Conditional ablation of *Ikkb* inhibits melanoma tumor development in mice" *The Journal of Clinical Investigation*, Jul. 2010, 120(7):2563-2574.

ATCC No. CCL-248 (T84, 1984), 2 pages.

Bellone, M. et al. "Cancer immunotherapy: synthetic and natural peptides in the balance" *Immunology Today*, Oct. 1999, 20(10):457-462.

Benjamin, B.A. et al. "Effect of proANF-(31—67) on sodium excretion in conscious monkeys" *Am J Physiol Regul Integr Comp Physiol*, 1995, 269:R1351-R1355, Abstract.

Buskins, C. et al. "Adenocarcinomas of the Gastro-Esophageal Junction: A Comparative Study of the Gastric Cardia and the Esophagus with Respect to Cyclooxygenase-2 Expression" *Digestive Disease Week Abstracts and Itinerary Planner*, 2003, Abstract No. 850.

Capizzi, R.L. "Molecular and Cellular Biology of Cancer" In: Internal Medicine, 4th Edition, Ed. Jay Stein, Elsevier Science, 1994, pp. 707-729.

Carter, S.K. et al. "Chemotherapy of Cancer" Second Edition, John Wiley & Sons: New York, 1981, Appendix C, 5 pages.

Chow, W.H. et al. "Rising Incidence of Renal Cell Cancer in the United States" *JAMA*, May 5, 1999, 281(17):1628-1631.

Clark, J.I. et al. "Adjuvant High-Dose Bolus Interleukin-2 for Patients With High-Risk Renal Cell Carcinoma: A Cytokine Working Group Randomized Trial" *J Clin Oncol*, Aug. 15, 2003, 21(16):3133-3140.

Cohen, H.T. et al. "Medical Progress: Renal-Cell Carcinoma" *N. Engl J Med*, Dec. 8, 2005, 353(23):2477-2490.

Daggubati, S. et al. "Adrenomedullin, endothelin, neuropeptide Y, atrial, brain, and C-natriuretic prohormone peptides compared as early heart failure indicators" *Cardiovascular Research*, 1997, 36:246-255.

De Palo, E.F. et al. "Circulating Immunoreactive proANP(1-30) and proANP(31-67) in Sedentary Subjects and Athletes" *Clinical Chemistry*, 2000, 46(6):843-847.

Dermer, G.B. "The Last Word: Another Anniversary for the War on Cancer" *Bio/Technology*, Mar. 1994, 12:320.

Dietz, J.R. et al. "Evidence supporting a physiological role for proANP-(1-30) in the regulation of renal excretion" *Am J Physiol Regul Integr Comp Physiol*, 2001, 280:R1510-R1517.

Fisher, E. et al. "Comparative Histopathologic, Histochemical, Electron Microscopic and Tissue Culture Studies of Bronchial Carcinoids and Oat Cell Carcinomas of Lung" *Am J Clin Pathol*, Feb. 1978, 69(2):165-172.

Franz, M. et al. "N-terminal fragments of the proatrial natriuretic peptide in patients before and after hemodialysis treatment" *Kidney International*, 2000, 58:374-383.

Franz, M. et al. "Plasma concentration and urinary excretion of N-terminal proatrial natriuretic peptides in patients with kidney diseases" *Kidney International*, 2001, 59:1928-1934.

Freshney, R.I. "Culture of Animal Cells: A Manual of Basic Technique" Alan R. Liss, Inc.: New York, 1983, pp. 3-4.

Friedman, H.S. et al. "Glioblastoma Multiforme and the Epidermal Growth Factor Receptor" *N. Engl J Med*, Nov. 10, 2005, 353(19):1997-1999.

Gaiger, A. et al. "Immunity to WT1 in the animal model and in patients with acute myeloid leukemia" *Blood*, Aug. 15, 2000, 96(4):1480-1489.

Garrett, M.D. et al. "Discovering Novel Chemotherapeutic Drugs for the Third Millennium" *European Journal of Cancer*, 1999, 35(14):2010-2030.

Gower, W.R. et al. "Four Peptides Decrease Human Colon Adenocarcinoma Cell Number and DNA Synthesis via Cyclic GMP" *International Journal of Gastrointestinal Cancer*, 2005, 36(2):77-88.

Gratzner, H.G., "Monoclonal Antibody to 5-Bromo- and 5-lododeoxyuridine: A New Reagent for Detection of DNA Replication" *Science*, Oct. 29, 1982, 218:474-475.

Gunning, M.E. et al. "Atrial Natriuretic Peptide$_{(31-67)}$ Inhibits Na$^+$ Transport in Rabbit Inner Medullary Collecting Duct Cells: Role of Prostaglandin E$_2$" *Journal of Clinical Investigation*, May 1992, 89:1411-1417.

Heim, J.M. et al. "Urodilatin and β-ANF: Binding Properties and Activation of Particulate Guanylate Cyclase" *Biochemical and Biophysical Research Communictions*, Aug. 30, 1989, 163(1):37-41.

Hunter, E.F.M. et al. "Analysis of peptides derived from Pro Atrial Natriuretic Peptide that circulate in man and increase in heart disease" *Scand J Clin Lab Invest*, 1998, 58:205-216.

Jemal, A. et al. "Cancer Statistics, 2005" *CA: A Cancer Journal for Clinicians*, 2005, 55:10-30.

Kaiser, J. et al. "CANCER: First Pass at Cancer Genome Reveals Complex Landscape" *Science*, Sep. 8, 2006, 313:1370.

Krontiris, T.G. "Molecular and Cellular Biology of Cancer" In: Internal Medicine, 4th Edition, Ed. Jay Stein, Elsevier Science, 1994, pp. 699-707.

Kumar, R. et al. "Stimulation of atrial natriuretic peptide receptor/guanylyl cyclase- A signaling pathway antagonizes the activation of protein kinase C-α in murine Leydig cells" *Biochimica et Biophysica Acta*, 1997, 1356:221-228.

La Vecchia, C. et al. "Smoking and Renal Cell Carcinoma" *Cancer Research*, Sep. 1, 1990, 50:5231-5233.

Lelièvre, V. et al. "Proliferative Actions of Natriuretic Peptides on Neuroblastoma Cells" *The Journal of Biological Chemistry*, Nov. 23, 2001, 276(47):43668-43676.

Linder, M.W. et al. "Pharmacogenetics: a laboratory tool for optimizing therapeutic efficiency" *Clinical Chemistry*, 1997, 43(2):254-266.

Martin, D.R. et al. "Three peptides from the ANF prohormone NH(2)-terminus are natriuretic and/or kaliuretic" *Am J Physiol Renal Physiol*, Dec. 1990, 258(5):F1401-F1408, Abstract.

McLaughlin, J.K. et al. "A Population-Based Case-Control Study of Renal Cell Carcinoma" *J Natl Cancer Inst*, Feb. 1984, 72:275-284.

Mellinghoff, I.K. et al. "Molecular Determinants of the Response of Glioblastomas to EGFR Kinase Inhibitors" *N Engl J Med*, Nov. 10, 2005, 353(19):2012-2024.

Morstyn, G. et al. "Immunohistochemical Identification of Proliferating Cells in Organ Culture Using Bromodeoxyuridine and a Monoclonal Antibody" *The Journal of Histochemistry and Cytochemistry*, 1986, 34(6):697-701.

Nguyen, T.D. et al. "Citrus Flavonoids Stimulate Secretion by Human Colonic $T_{84}$ Cells$^{1,2}$" *The Journal of Nutrition*, 1993, 123:259-268.

Pan, E. et al. "Central Nervous System: Primary Neoplasms of the Central Nervous System" In: Kufe, D.W., Pollock, R.F., Weichselbaum, R.R., Bast, R.C., Jr., Gansler, I.S., Holland, J.F., and Frei, E., III (Eds.), *Cancer Medicine*, 6th Edition, 2003, pp. 1193-1226, London: BC Decker.

Pitari, G.M. et al. "Guanylyl cyclase C agonists regulate progression through the cell cycle of human colon carcinoma cells" *PNAS*, Jul. 3, 2001, 98(14):7846-7851.

Rashed, H.M. et al. "Atrial Natriuretic Peptide Inhibits Growth of Hepatoblastoma (HEP G2) Cells by Means of Activation of Clearance Receptors" *Hepatology*, Apr. 1993, 17(4):677-684.

Ropper, A.H. and Brown, R.H. (Eds.) "Intracranial Neoplasms and Paraneoplastic Disorders" In: Adams and Victor's Principles of Neurology, 8th Edition, 2005, New York: McGraw-Hill, pp. 546-591.

Rosenzweig, A. et al. "Atrial Natriuretic Factor and Related Peptide Hormones" *Annu. Rev. Biochem.*, 1991, 60:229-255.

Saba, S.R. et al. "Immunocytochemical Localization of Atrial Natriuretic Peptide, Vessel Dilator, Long-acting Natriuretic Peptide, and Kaliuretic Peptide in Human Pancreatic Adenocarcinomas" *Journal of Histochemistry & Cytochemistry*, 2005, 53(8):989-995.

Salani, D. et al. "Endothelin-1 Induces an Angiogenic Phenotype in Cultured Endothelial Cells and Stimulates Neovascularization *In Vivo*" *American Journal of Pathology*, Nov. 2000, 157(5)1 703-1711.

Saxenhofer, H. et al. "Urodilatin: binding properties and stimulation of cGMP generation in rat kidney cells" *Am J Physiol Renal Physiol*, 1993, 264:F267-F273, Abstract.

Schulz-Knappe, P. et al. "Isolation and Structural Analysis of "Urodilatin", a New Peptide of the Cardiodilatin-(ANP)-Family, Extracted from Human Urine" *Kiln Wochenschr*, 1988, 66:752-759.

Schwede, F. et al. "Cyclic nucleotide analogs as biochemical tools and prospective drugs" *Pharmacology & Therapeutics*, 2000, 87:199-226.

Schweitz, H. et al. "A New Member of the Natriuretic Peptide Family Is Present in the Venom of the Green Mamba (*Dendroaspis angusticeps*)" *The Journal of Biological Chemistry*, Jul. 15, 1992, 267(20):13928-13932.

Scott, D.A. et al. "The Pendred syndrome gene encodes a chloride-iodide transport protein" *Nature Genetics*, Apr. 1999, 21:440-443.

Shapiro, J.A. et al. "Body Mass Index and Risk of Renal Cell Carcinoma" *Epidemiology*, Mar. 1999, 10(2):188-191.

Senger, D. et al. "Long-Term Survivors of Glioblastoma: Statistical Aberration or Important Unrecognized Molecular Subtype?" *The Cancer Journal*, May/Jun. 2003, 9(3):214-221.

Sudoh, T. et al. "C-Type Natriuretic Peptide (CNP): A New Member of Natriuretic Peptide Family Identified in Porcine Brain" *Biochemical and Biophysical Research Communications*, Apr. 30, 1990, 168(2):863-870.

Turner, G.A. et al. "Urine cyclic nucleotide concentrations in cancer and other conditions; cyclic GMP: a potential marker for cancer treatment" *J Clin Pathol*, 1982, 35:800-806.

Valentin, J.P. et al. "Urodilatin Binds to and Activates Renal Receptors for Atrial Natriuretic Peptide" *Hypertension*, Apr. 1993, 21(4):432-438.

Van Meir, E.G. et al. "Release of an inhibitor of angiogenesis upon induction of wild type p35 expression in glioblastoma cells" *Nature Genetics*, Oct. 1994, 8:171-176.

Vesely, B.A. et al. "Five cardiac hormones decrease the number of human small-cell lung cancer cells" *Eur J Clin Invest*, 2005, 35:388-398.

Vesely, B.A. et al. "Four cardiac hormones cause cell death in 81% of human ovarian adenocarcinoma cells" *Cancer Therapy*, 2007, 5:97-104.

Vesely, B.A. et al. "Four cardiac hormones eliminate 4-fold more human glioblastoma cells than the green mamba snake peptide" *Cancer Letters*, 2007, 254:94-101.

Vesely, B.A. et al. "Four peptide hormones' specific decrease (up to 97%) of human prostate carcinoma cells" *Eur J Clin Invest*, 2005, 35(11):700-710.

Vesely, B.A. et al. "Primary Malignant Tumors of the Heart: Four Cardiovascular Hormones Decrease the Number and DNA Synthesis of Human Angiosarcoma Cells" *Cardiology*, 2006, 105:226-233.

Vesely, B.A. et al. "Vessel dilator: Most potent of the atrial natriuretic peptides in decreasing the number of DNA synthesis of human squamous lung cancer cells" *Cancer Letters*, 2006, 233:226-231.

Vesely, B.A. et al. "Four peptide hormones decrease the number of human breast adenocarcinoma cells" *Eur J Clin Invest*, 2005, 35(1):60-69.

Vesely, B.A. et al. "Urodilatin and four cardiac hormones decrease human renal carcinoma cell numbers" *Eur J Clin Invest*, 2006, 36(11):810-819.

Vesely, D.L. et al. "Atrial Natriuretic Peptide Increases Urodilatin in the Circulation" *American Journal of Nephrology*, 1998, 18(3):204-213, Abstract.

Vesely, D.L. et al. "Atrial Natriuretic Prohormone Peptides 1-30, 31-67, and 79-98 Vasodilate the Aorta" *Biochemical and Biophysical Research Communications*, Nov. 13, 1987, 148(3):1540-1548.

Vesely, D.L. et al. "Increased Release of the N-Terminal and C-Terminal Portions of the Prohormone of Atrial Natriuretic Factor During Immersion-Induced Central Hypervolemia in Normal Humans[1]$_{(42990)}$" *Proc Soc Exp Biot Med*, 1989, 192:230-235.

Vesely, D.L. et al. "Negative Feedback of Atrial Natriuretic Peptides" *Journal of Clinical Endocrinology and Metabolism*, 1994, 78(5):1128-1134.

Vesely, D.L. et al. "Novel therapeutic approach for cancer using four cardiovascular hormones" *Eur J Clin Invest*, 2004, 34(10):674-682.

Vesely, D.L. et al. "Three Peptides From the Atrial Natriuretic Factor Prohormone Amino Terminus Lower Blood Pressure and Produce Diuresis, Natriuresis, and/or Kaliuresis in Humans" *Circulation*, Sep. 1994, 90(3):1129-1140.

Vesely, D.L. et al. "Vessel Dilator Enhances Sodium and Water Excretion and Has Beneficial Hemodynamic Effects in Persons With Congestive Heart Failure" *Circulation*, Jul. 28, 1998, 98:323-329.

Vesely, D.L. "Natriuretic peptides and acute renal failure" *Am J Physiol Renal Physiol*, 2003, 285:F167-F177.

Villarreal, D. et al. "Hemodynamic and Renal Effects of ProANF$_{31-67}$ in Hypertensive Rats$_{(44399)}$" *Proceedings of the Society for Experimental Biology and Medicine*, 1999, 221(3):166-170.

Weller, M. et al. "Predicting Chemoresistance in Human Malignant Glioma Cells: The Role of Molecular Genetic Analysis" *Int. J. Cancer (Pred. Oncol.)*, 1998, 79:640-644.

White, R.E. et al. "Potassium channel stimulation by natriuretic peptides through cGMP-dependent dephosphorylation" *Nature*, Jan. 21, 1993, 361:263-266.

Wigle, D.A. et al. "ANP secretion from small cell lung cancer lines: a potential model of ANP release" *Am J Physiol Heart Circ Physiol*, 1995, 268(5):H1869-H1874, Abstract.

Winters, C.J. et al, "The N-Terminus and a 4,000-MW Peptide From the Midportion of the N-Terminus of the Atrial Natriuretic Factor Prohormone Each Circulate in Humans and Increase in Congestive Heart Failure" *Circulation*, Sep. 1989, 80(3):438-449.

Yagoda, A. et al. "Chemotherapy for Advanced Renal-Cell Carcinoma: 1983-1993" *Seminars in Oncology*, Feb. 1995, 22(1):42-60.

Yang, J.C. et al. "Randomized Study of High-Dose and Low-Dose Interleukin-2 in Patients With Metastatic Renal Cancer" *J Clin Oncol*, Aug. 15, 2003, 21(16):3127-3132.

Yu, C.C.W. et al. "The assessment of cellular proliferation by immunohistochemistry: A review of currently available methods and their applications" *The Histochemical Journal*, Mar. 1992, 24(3):121-131.

Yu, M.C. et al. "Cigarette Smoking, Obesity, Diuretic Use, and Coffee Consumption as Risk Factors for Renal Cell Carcinoma" *J Natl Cancer Inst*, Aug. 1986, 77:351-356.

Zeidel, M.L. "Regulation of Collecting Duct Na$^+$Reabsorption by ANP 31-67" *Clinical and Experimental Pharmacology and Physiology*, 1995, 22(2):121-124, Abstract.

Zellner, A. et al. "Disparity in Expression of Protein Kinase C α in Human Glioma versus Glioma-derived Primary Cell Lines: Therapeutic Implications" *Clinical Cancer Research*, Jul. 1998, 4:1797-1802.

Zips, D. et al. "New Anticancer Agents: *In Vitro* and *In Vivo* Evaluation" *In Vivo*, Jan./Feb. 2005, 19(1):1-7.

Office Action dated Jan. 26, 2011 in Canadian Application Serial No. 2,518,550, filed Mar. 19, 2004.

Office Action dated Apr. 2, 2009 in U.S. Appl. No. 11/833,757, filed Aug. 3, 2007.

Office Action dated Oct. 19, 2009 in U.S. Appl. No. 11/833,757, filed Aug. 3, 2007.

Response to Office Action dated Apr. 2, 2009 in U.S. Appl. No. 11/833,757, filed Aug. 3, 2007.

Response to Office Action dated Oct. 19, 2009 in U.S. Appl. No. 11/833,757, filed Aug. 3, 2007.

Office Action dated Apr. 27, 2011 in U.S. Appl. No. 11/799,225, filed Apr. 30, 2007.

Response to Office Action dated Sep. 2, 2009 in U.S. Appl. No. 11/799,225, filed Apr. 30, 2007.

Response to Office Action dated Apr. 1, 2010 in U.S. Appl. No. 11/799,225, filed Apr. 30, 2007.

Response to Office Action dated Aug. 20, 2010 in U.S. Appl. No. 11/799,225, filed Apr. 30, 2007.

Response to Office Action dated Apr. 27, 2011 in U.S. Appl. No. 11/799,225, filed Apr. 30, 2007.

Response to Office Action dated Jun. 1, 2009 in U.S. Appl. No. 11/998,792, filed Nov. 30, 2007.

Response to Office Action dated Dec. 11, 2009 in U.S. Appl. No. 11/998,792, filed Nov. 30, 2007.

Response to Office Action dated May 18, 2010 in U.S. Appl. No. 11/998,792, filed Nov. 30, 2007.
Response to Office Action dated Oct. 13, 2010 in U.S. Appl. No. 11/998,792, filed Nov. 30, 2007.
Notice of Allowance dated Jul. 27, 2011 in U.S. Appl. No. 11/799,225, filed Apr. 30, 2007.
Office Action dated Jun. 27, 2011 in U.S. Appl. No. 12/908,806, filed Oct. 20, 2010.

Gower, W.R. et al. "Four Peptides Decrease Human Colon Adenocarcinoma Cell Number and DNA Synthesis via Cyclic GMP" *International Journal of Gastrointestinal Cancer*, 2005, 36(2):77-88.
Keimer, A.K. et al. "Effects of Different Natriuretic Peptides on Nitric Oxide Synthesis in Macrophages" *Endocrinology*, 1997, 138(10):4282-4290.

* cited by examiner

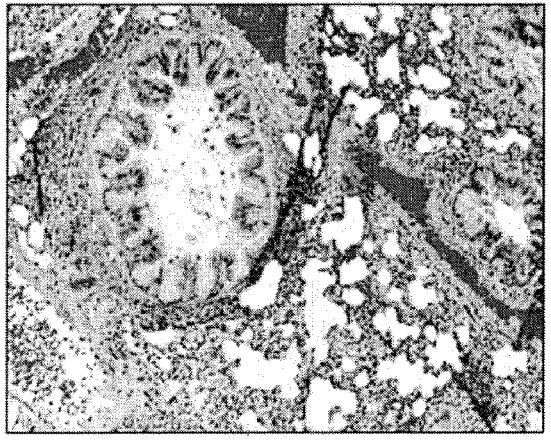 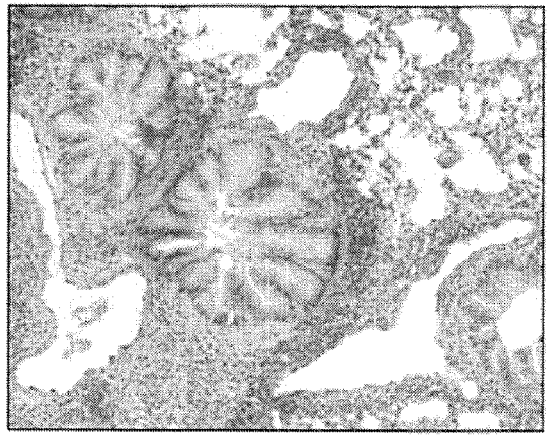
FIG. 2A          FIG. 2B
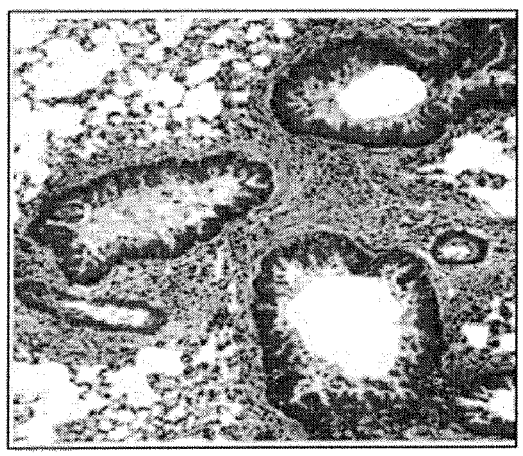 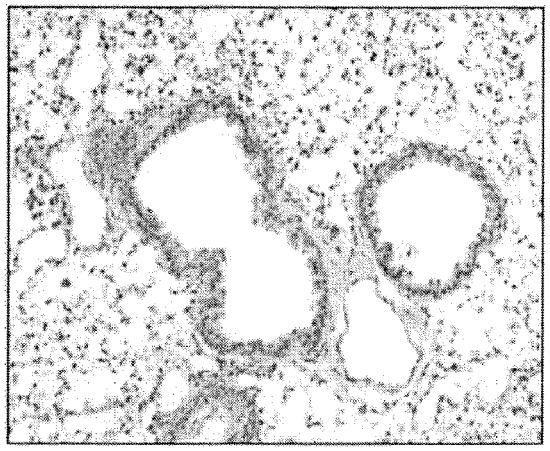
FIG. 2C          FIG. 2D Control  Vehicle  NP$_{73\text{-}102}$

MATERIALS AND METHODS FOR TREATMENT OF INFLAMMATORY AND CELL PROLIFERATION DISORDERS

CROSS-REFERENCE TO RELATED APPLICATION

The present application is a continuation of U.S. application Ser. No. 11/059,814, filed Feb. 17, 2005, now abandoned which claims the benefit of U.S. Provisional Application Ser. No. 60/521,072, filed Feb. 17, 2004, each of which is hereby incorporated by reference herein in its entirety, including any figures, tables, nucleic acid sequences, amino acid sequences, or drawings.

BACKGROUND OF THE INVENTION

The vast majority of cancers of the lung, breast and colon are adenocarcinomas, which arise from pre-existing adenomatous polyps that develop in the normal colonic mucosa. This adenoma-carcinoma sequence is a well-characterized clinical and histopathologic series of events with which discrete molecular genetic alterations have been associated. Lung tumor development and metastasis are complex processes that include transformation, proliferation, resistance to apoptosis, neovascularization, and metastatic spread. A number of gene products have been identified that play critical roles in these processes. It has been suggested that the development of epithelial-derived tumors, the most common class of cancers, involves mutations of tumor suppressors and proto-oncogenes or epigenetic alterations of signaling pathways affecting cell proliferation and/or survival, which in turn may be caused by inflammation induced by infections and reactive oxygen species (ROS) (Ernst, P. *Aliment Pharmacol Ther.*, 1999, 13(1):13-18).

A group of four peptide hormones, originating from the 126-amino acid atrial natriuretic factor (ANF) prohormone, have become known for their vasodilator activity. These four peptide hormones, consisting of amino acids 1-30, 31-67, 79-98, and 99-126 of this prohormone, have been named long acting natriuretic peptide (LANP), vessel dilator (VD), kaliuretic peptide (KP), and atrial natriuretic peptide (ANP), respectively, for their most prominent effects (Angus R. M. et al., *Clin Exp Allergy* 1994, 24:784-788). The ANP sequence, particularly the C-terminal portion, is highly conserved among species (Seidman et al., *Science*, 1984, 226:1206-1209). ANP has been proposed to be useful for treatment of various cardiovascular, respiratory, and renal diseases (Vesely, D. L. *Cardiovascular*, 2001, 51:647-658), but also causes inflammation. The family of natriuretic hormone peptides has been shown to have broad physiologic effects, including vasodilation and inhibition of aldosterone secretion and cardiovascular homeostasis.

As indicated above, ANF, the 126 amino acid prohormone, gives rise to four peptides: LANP (amino acids 1-30), VD (amino acids 31-67), KP (amino acids 79-98) and ANP (amino acids 99-126, also referred to herein as $NP_{99-126}$) (Angus R. M. et al, *Clin Exp Allergy*, 1994, 24:784-788). The ANP sequence particularly the C-terminal portion is highly conserved among species (Seidman et al., *Science*, 1984, 226: 1206-1209). The natriuretic peptide receptors (NPRs), NPR-A and NPR-B, are expressed in many different tissues of various organs systems, and are coupled to guanylyl cyclase. ANP and BNP are thought to signal primarily through NPR-A by increasing cGMP and activating cGMP-dependent protein kinase (PKG). NPR-A is the primary receptor for ANP while NPR-B seems to bind CNP most effectively. PKG activation in turn activates ion transporters and transcription factors, which together affect cell growth and proliferation, apoptosis and inflammation. NPR-C is a clearance receptor for ANP removal, but also appears to signal phospholipase C activation and a decrease in adenylyl cyclase activity through a cGMP-independent pathway (Abbey and Potter, *Endocrinology*, 2003, 144: 240-246; Silberbach and Roberts, *Cell Signal*, 2001, 13:221-231). The signaling mechanisms underlying ANP's growth regulatory effects are poorly understood, although a number of reports suggest that ANP acts through mitogen-activated protein kinases (Silberbach and Roberts, *Cell Signal*, 2001, 13:221-231).

Most cells of the mucosal immune system have ANP receptors (NPRs) and there is evidence that natriuretic peptides regulate the immune response and inflammation (Kurihara et al., *Biochem Biophys Res Commun* 1987, 149:1132-1140). ANP stimulates migration of human neutrophils (Izumi et al., *J Clin Invest* 2001, 108:203-213), and inhibit nitric oxide and TNF-α production by murine macrophages (Kiemer and Vollmar, *J Biol Chem* 1998, 273:13444-13451; Kiemer et al., *J Immunol* 2000, 165:175-81). It has been suggested that the ANP system may be a critical component of the immune response through its actions on both immune and non-immune cells. In patients with lung tumors, the immune response plays a large part in the progression of the disease and, consequently, the NPR system may potentially be involved. The alveolar macrophages in lung cancer patients secrete more pro-inflammatory cytokines, such as IL-6 and IL-1β, after LPS stimulation than in persons with non-malignant disease (Matanic et al., *Scand J Immunol* 2003, 57:173-178). Increased IL-6 in lung cancer patients enhances the acute phase response, and is correlated with h poor nutritional status and lowered survival (Martin et al., *Cytokine* 1999, 11; 267-273). The cells of the immune system, such as natural killer (NK) cells, Vα24 NKT, which are necessary for cancer surveillance may also be reduced in lung tumor patients (Motohashi et al., *Int J Cancer* 2002, 102:159-165). The most common clinical paraneoplastic syndrome in patients with small-cell lung cancer (SCLC) is hyponatremia, which is believed to be caused by tumor secretion of vasopressin. Tumor biopsies from patients with SCLC and hyponatremia expressed the gene for ANP (Shimizu et al., *Cancer* 1991, 68: 2284-2288; Bliss et al., *J Natl Can Inst,* 1990, 82: 305-310). Thus, the reduced sodium levels seen in SCLC patients may be attributed to the secretion of ANP (Bliss et al., *J Natl Can Inst,* 1990, 82: 305-310). Human SCLC cell lines express functional ANP receptors (Ohsaki et al., Cancer Res 1993, 53: 3165-3171). A majority of SCLC cell lines produce ANP and some produce BNP as well (Ohsaki et al., *Oncology* 1999, 56:155-159). In contrast, in NSCLC cell lines, which are derived mostly from adenocarcinomas that comprise about two-thirds of all lung cancers, little is known about their growth regulation in response to ANP cascade.

The present inventor has found that the N-terminal natriuretic peptides, such as pNP73-1102, are capable of inhibiting NFκB activation (Mohapatra, international application WO 2004/022003, published Mar. 18, 2004, which is incorporated herein by reference in its entirety), and that the ANP cascade plays a critical role in cell proliferation and inflammation. NFκB, a transcription factor and a key player in inflammatory processes, has been implicated in the development of cancer in liver and mammary tissues (Greten F. R. et al. *Cell*, 2004, 118: 285-296; Pikarsky F. et al. *Nature*, 2004, 431: 461-466). Activation of the NF-κB pathway enhances tumor development and may act primarily in the late stages of tumorigenesis. Inhibition of NF-κB signaling uniformly suppressed tumor development; however, depending upon the model studied, this salutary effect was attributed to an increase in tumor cell apoptosis, reduced expression of tumor cell growth factors supplied by surrounding stromal cells, or abrogation of a tumor cell dedifferentiation program that is critical for tumor invasion/metastasis.

BRIEF SUMMARY OF THE INVENTION

The present invention pertains to methods for reducing natriuretic peptide receptor-A (also known in the art as NPRA, NPR-A, and guanylate cyclase A) activity in vitro or in vivo. The method of the invention may be used for treating inflammatory and cell proliferation disorders, such as cancer.

In another aspect, the present invention concerns methods for identifying agents useful for treating inflammatory and cell proliferation disorders by determining whether the candidate agent reduces activity of the natriuretic peptide receptor-A (also known in the art as NPRA, NPR-A, and guanylate cyclase A) in vitro and/or in vivo (also referred to herein as the diagnostic method or assay of the invention).

In another aspect, the method of the present invention may be used for reducing the growth of cancer cells in vitro or in vivo. In one aspect, the method is useful for treating cancers, such as adenocarcinomas of lung, breast, ovary and melanomas, which may be caused by cell proliferation and inflammation induced by the atrial natriuretic peptide (ANP) cascade.

In one embodiment, the method of the present invention comprises administering a therapeutically effective amount of an agent that reduces NPR-A activity. In another embodiment, the method of the present invention comprises administering a therapeutically effective amount of an N-terminal natriuretic peptide (referred to herein as NP or NP peptide), or a polynucleotide encoding NP and an operably-linked promoter sequence, to a patient in need of such treatment. As used herein, NP refers to peptides derived from atrial natriuretic factor (ANF) hormone, or a biologically active fragment, homolog, or variant thereof. In another embodiment, the method of the present invention comprises administering an effective amount of NP, or a polynucleotide encoding NP and an operably-linked promoter, to one or more cancer cells, wherein the NP is capable of reducing cell proliferation and/or tumor growth. The effect of the NP or a biologically active fragment, homolog, or variant thereof, is capable of reducing cancer cell growth in vitro or in vivo.

Specifically exemplified NPs comprise an amino acid sequence selected from the group consisting of amino acids 1-30 of ANF (also known as "long acting natriuretic peptide" and referred to herein as $NP_{1-30}$ or SEQ ID NO:1), amino acids 31-67 of ANF (also known as "vessel dilator" and referred to herein as $NP_{31-67}$ or SEQ ID NO:2), and amino acids 79-98 of ANF (also known as "kaliuretic peptide" and referred to herein as $NP_{79-98}$ or SEQ ID NO:3), or biologically active fragments or homologs of any of the foregoing. Other exemplified NPs comprise amino acids 73-102 of proANF (referred to herein as $NP_{73-102}$ or SEQ ID NO:5), or SEQ ID NO:6, or biologically active fragment(s) or homolog(s) of the foregoing. In one embodiment, the NP administered to the patient does not consist of $NP_{99-126}$ (SEQ ID NO:4).

In another embodiment, the method of the present invention comprises administering an effective amount of at least one nucleic acid molecule encoding an NP to a patient in need of such treatment. The present inventor has determined that introduction of a nucleic acid molecule encoding NP is capable of inhibiting tumor growth and tumor metastasis. The gene delivery method of the present invention permits long-term expression of NP-encoding nucleic acid sequences in vivo, thereby conferring anti-cancer effects. In one embodiment, a therapeutically effective amount of at least one nucleic acid molecule encoding a peptide comprising an amino acid sequence selected from the group consisting of SEQ ID NO:1, SEQ ID NO:2, SEQ ID NO:3, SEQ ID NO:4, and SEQ ID NO:5 or biologically active fragments or homologs of any of the foregoing, are administered to the patient.

In another aspect, the present invention concerns an isolated peptide comprising the amino acid sequence $NP_{73-102}$ (SEQ ID NO:5) or SEQ ID NO:6, or a biologically active fragment or homolog of the foregoing. In another aspect, the present invention concerns an isolated nucleic acid molecule encoding the amino acid sequence of $NP_{73-102}$ (SEQ ID NO:5) or encoding the amino acid sequence of SEQ ID NO:6, or a biologically active fragment or homolog thereof.

In another aspect, the present invention concerns an expression vector comprising a nucleic acid sequence encoding an NP, and a promoter sequence that is operably linked to the NP-encoding nucleic acid sequence. In one embodiment, the expression vector is a DNA plasmid or virus. In another aspect, the present invention concerns a pharmaceutical composition comprising a nucleic acid sequence encoding an NP, and a pharmaceutically acceptable carrier.

BRIEF DESCRIPTION OF THE DRAWINGS

For a fuller understanding of the nature and objects of the invention, reference should be made to the following detailed description, taken in connection with the accompanying drawings, in which:

FIGS. 2A-2D show NPRA deficiency decreases pulmonary inflammation. Groups (n=3) of wild type DBA/2 (wt) (FIG. 2A) and NPR-C deficient ($NPRC^{-/-}$) (FIG. 2B) mice and wild type C57/BL6 (wt) (FIG. 2C) and NPR-A ($NPRA^{-/-}$) (FIG. 2D) were sensitized with OVA (20 mg/mouse) and after 2 weeks challenged i.n. with OVA (20 mg/mouse). One day later mice were sacrificed and lung sections were stained with H & E to examine inflammation.

FIG. 5D shows lungs removed from mice treated with chitosan nanoparticles carrying $pNP_{73-102}$ (CPNP73-102) (Rx) or empty plasmid pVAX (control). The lungs of control mice showed several lung nodules in contrast to mice treated with CPNP73-102, which showed very few tumors. Intranasal CPNP73-102 administration abrogated tumor formation in A549 injected nude mice. Nude mice were given $5 \times 10^6$ cells intravenously (tail vein) and weekly injections of nanoparticle carrying either empty plasmid (control) or pNP73-102 (Rx). Three weeks later, mice were sacrificed and lung sections were stained with H & E to examine the lung nodules (FIG. 5D). Control shows nodules and tumor cell mass, whereas the treated group had no tumors. Sections were also stained with antibodies to cyclinB and to phospho-Bad (FIG. 5E). The results show that mice treated with CPNP73-102 had no tumors in the lung and did not show any staining for pro-mitotic Cyclin-B and anti-apoptotic marker phospho-Bad.

BRIEF DESCRIPTION OF THE SEQUENCES

Figure 1:
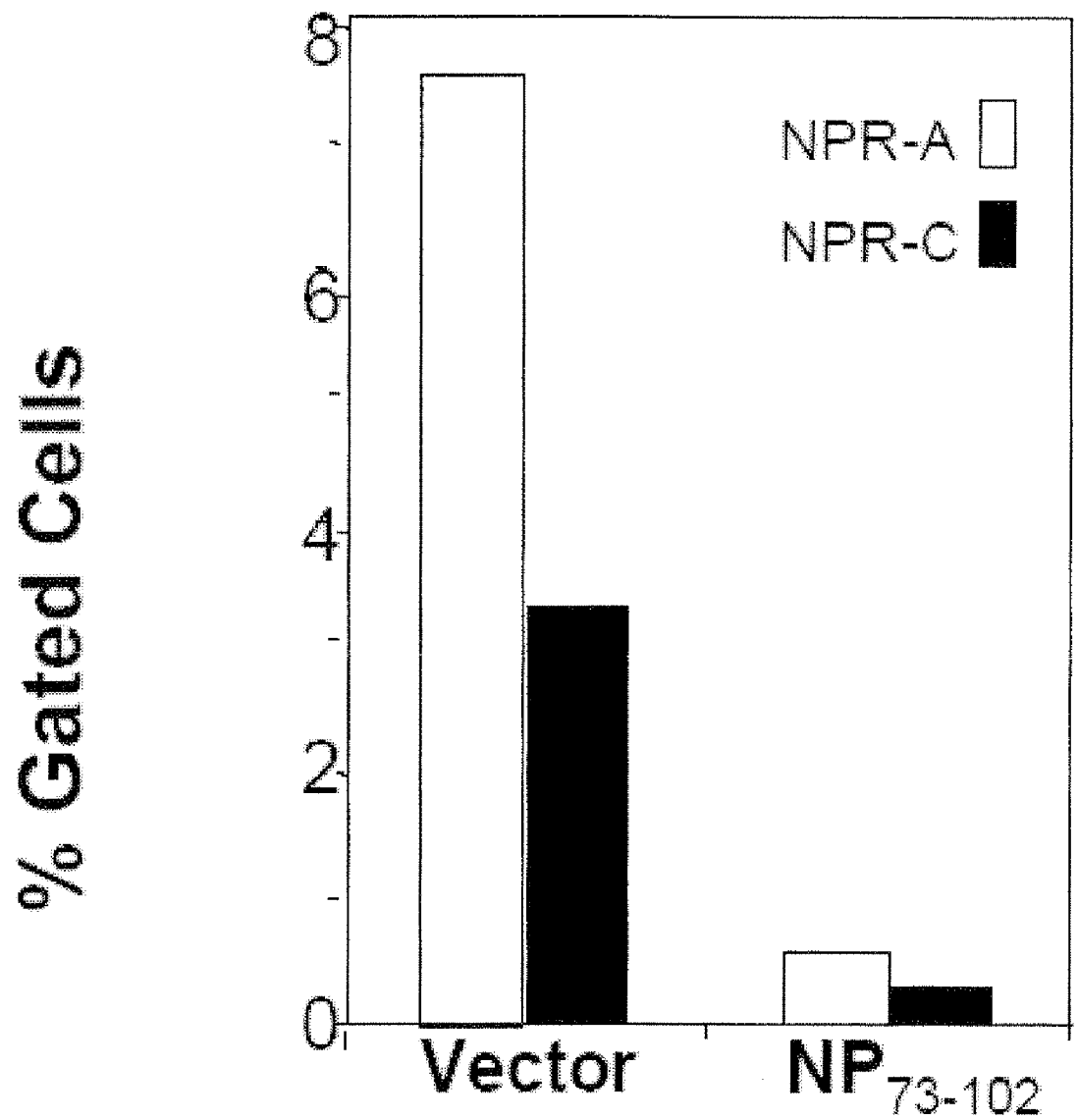
FIG. 1 shows pNP 73-102 inhibits NPRA expression. Pregnant (12 days) mice were injected i.p. with pVAX (vector), or pNP73-102. After 1 day, mice were sacrificed, thymi removed from the embryo, and homogenized. Cells were centrifuged and erythrocytes were lysed and incubated with anti-NPR-Ab or anti-NPR-C for 1 hour, washed, and incubated with PE-conjugated secondary antibodies. Levels of NPRA and NPRC were determined by flow cytometry.

SEQ ID NO: 1 is the amino acid sequence of human "long acting natriuretic peptide" or $NP_{1-30}$:

$^1$NPMYN AVSNADLMDF KNLLDHLEEK MPLED$^{30}$. (SEQ ID NO: 1)

SEQ ID NO:2 is the amino acid sequence of human "vessel dilator" or $NP_{31-67}$:

(SEQ ID NO: 2)
$^{31}$EVVPP QVLSEPNEEA GAALSPLPEV PPWTGEVSPA QR$^{67}$.

SEQ ID NO:3 is the amino acid sequence of human "kaliuretic peptide" or $NP_{79-98}$:

$^{79}$SSDRSAL LKSKLRALLT APR$^{98}$. (SEQ ID NO: 3)

SEQ ID NO:4 is the amino acid sequence of human "atrial natriuretic peptide" (ANP) or $NP_{99-126}$:

$^{99}$SLRRSSC FGGRMDRIGA QSGLGCNSFR Y$^{126}$. (SEQ ID NO: 4)

SEQ ID NO:5 is the amino acid sequence of cloned mouse $pNP_{73-102}$:

$^{73}$GSPWDPSDRS ALLKSKLRAL LAGPRSLRRS$^{102}$. (SEQ ID NO: 5)

SEQ ID NO:6 is the amino acid sequence of cloned mouse NP fragment:

(SEQ ID NO: 6)
VSNTDLMDFK NLLDHLEEKM PVEDEVMPPQ ALSEQTE.

SEQ ID NO:7 is the amino acid sequence for the human preproANP (NCBI ACCESSION # NM_006172) wherein the underlined amino acids represent the signal sequence which is cleaved off to form the mature peptide:

(SEQ ID NO: 7)
$^1$MSSFSTTTVS FLLLLAFQLL GQTRANPMYN AVSNADLMDF

KNLLDHLEEK MPLEDEVVPP QVLSEPNEEA GAALSPLPEV

PPWTGEVSPA QRDGGALGRG PWDSSDRSAL LKSKLRALLT

APRSLRRSSC FGGRMDRIGA QSGLGCNSFR Y$^{151}$.

SEQ ID NO:8 is a forward primer for the cDNA sequence encoding mouse prepro ANF protein:

(SEQ ID NO: 8)
5'-gac ggc aag ctt act atg ggc agc ccc tgg
gac cc-3'.

SEQ ID NO:9 is a reverse primer for the cDNA sequence encoding mouse pre-proANF protein:

(SEQ ID NO: 9)
5'-acc ccc ctc gag tta tta tct tcg tag gct ccg-3'.

SEQ ID NO:10 is a forward primer for the cDNA sequence encoding mouse NP fragment:

(SEQ ID NO: 10)
5'-aat cct aag ctt agt atg gtg tcc aac aca gat-3'.

SEQ ID NO:11 is a reverse primer for the cDNA sequence encoding mouse NP fragment:

(SEQ ID NO: 11)
5'-tgc gaa ctc gag tta ctc agt ctg ctc act cag ggc ctg cg-3'.

SEQ ID NO:12 is the nucleotide sequence encoding cloned mouse pNP$_{73-102}$:

(SEQ ID NO: 12)
ggc agc ccc tgg gac ccc tcc gat aga tct gcc ctc ttg aaa agc aaa ctg agg gct ctg ctc gct ggc cct cgg agc cta cga aga tcc.

SEQ ID NO:13 is the nucleotide sequence encoding cloned mouse pNP fragment:

(SEQ ID NO: 13)
atg gtg tcc aac aca gat ctg atg gat ttc aag aac ctg cta gac cac ctg gag gag aag atg ccg gta gaa gat gag gtc atg ccc ccg cag gcc ctg agt gag cag act gag taa.

SEQ ID NO:14 is the mRNA nucleotide sequence encoding human ANP (NCBI Accession # NM_006172:

(SEQ ID NO: 14)
```
  1 tggcgaggga cagacgtagg ccaagagagg ggaaccagag aggaaccaga ggggagagac
 61 agagcagcaa gcagtggatt gctccttgac gacgccagca tgagctcctt ctccaccacc
121 accgtgagct tcctcctttt actggcattc cagctcctag gtcagaccag agctaatccc
181 atgtacaatg ccgtgtccaa cgcagacctg atggatttca gaatttgct ggaccatttg
241 gaagaaaaga tgcctttaga agatgaggtc gtgccccac aagtgctcag tgagccgaat
301 gaagaagcgg gggctgctct cagccccctc cctgaggtgc ctccctggac cggggaagtc
361 agcccagccc agagagatgg aggtgccctc ggcggggcc cctgggactc tctgatcga
421 tctgccctcc taaaaagcaa gctgagggcg ctgctcactg cccctcggag cctgcggaga
481 tccagctgct tcggggggcag gatggacagg attggagccc agagcggact gggctgtaac
541 agcttccggt actgaagata acagccaggg aggacaagca gggctgggcc tagggacaga
601 ctgcaagagg ctcctgtccc ctgggtctc tgctgcattt gtgtcatctt gttgccatgg
661 agttgtgatc atcccatcta agctgcagct tcctgtcaac acttctcaca tcttatgcta
721 actgtagata aagtggtttg atggtgactt cctcgcctct cccacccat gcattaaatt
781 ttaaggtaga acctcacctg ttactgaaag tggtttgaaa gtgaataaac ttcagcacca
841 tggac.
```

SEQ ID NO:15 is the human gene for atrial natritiretic factor propeptide (coding sequence includes-join (570 . . . 692, 815 . . . 1141, 2235 . . . 2240); sig. peptide=570 . . . 644; mat. peptide=join (645 . . . 692, 815 . . . 1141, 2235 . . . 2237), (NCBI ACCESSION NO: X01471; Greenberg, B. D. et al., *Nature*, 1984, 312(5995):656-658):

(SEQ ID NO: 15)
```
  1 ggatccattt gtctcgggct gctggctgcc tgccatttcc tcctctccac ccttatttgg
 61 aggccctgac agctgagcca caaacaaacc aggggagctg gcaccagca agcgtcaccc
121 tctgtttccc cgcacggtac cagcgtcgag gagaaagaat cctgaggcac ggcggtgaga
181 taaccaagga ctcttttta ctcttctcac acctttgaag tgggagcctc ttgagtcaaa
241 tcagtaagaa tgcggctctt gcagctgagg gtctgggggg ctgttgggc tgcccaaggc
301 agagagggc tgtgacaagc cctgcggatg ataactttaa aagggcatct cctgctggct
361 tctcacttgg cagctttatc actgcaagtg acagaatggg gagggttctg tctctcctgc
421 gtgcttggag agctgggggg ctataaaaag aggcggcact gggcagctgg agacaggga
481 cagacgtagg ccaagagagg ggaaccagag aggaaccaga ggggagagac agagcagcaa
```

-continued

```
 541 gcagtggatt gctccttgac gacgccagca tgagctcctt ctccaccacc accgtgagct
 601 tcctccttt  actggcattc cagctcctag gtcagaccag agctaatccc atgtacaatg
 661 ccgtgtccaa cgcagacctg atggatttca aggtagggcc aggaaagcgg gtgcagtctg
 721 gggccagggg gctttctgat gctgtgctca ctcctcttga tttcctccaa gtcagtgagg
 781 tttatcccct tccctgtatt ttccttttct aaagaatttg ctggaccatt tggaagaaaa
 841 gatgccttta aagatgagg  tcgtgccccc acaagtgctc agtgagccga atgaagaagc
 901 gggggctgct ctcagccccc tccctgaggt gcctccctgg accggggaag tcagcccagc
 961 ccagagagat ggaggtgccc tcgggcgggg ccctgggac  tcctctgatc gatctgccct
1021 cctaaaaagc aagctgaggg cgctgctcac tgcccctcgg agcctgcgga gatccagctg
1081 cttcggggc  aggatggaca ggattggagc ccagagcgga ctgggctgta acagcttccg
1141 ggtaagagga actggggatg gaaatgggat gggatggaca ctactgggag acaccttcag
1201 caggaaaggg accaatgcag aagctcattc cctctcaagt ttctgcccca cacccagag
1261 tgccccatgg gtgtcaggac atgccatcta ttgtccttag ctagtctgct gagaaaatgc
1321 ttaaaaaaaa aagggggggg gctgggcacg gtcgtcacgc tgtaatccc  agcactttgg
1381 gaggccaggc agcggatcat gaggtcaaga gatcaagact atcctggcca acatggtgaa
1441 accccagctc tactaaaaat acaaaaatta gctgggtgtg tggcgggcac ctgtactctc
1501 agctacttgg gaggctgagg caggagaatc acttgaaccc aggaggcaga ggttgcagtg
1561 agcagagatc acgccactgc agtccagcct aggtgataga gcgagactgt ctcaaaaaaa
1621 aaaaaaaaag gccaggcgcg gtggctcacg cctgtaatcc cagcgctttg ggaggccaag
1681 gcgggtggat cacgaggtca ggagatggag accatcctgg ctaacacggt gaaacccccgt
1741 ctctactaaa aatacaaaaa attagccagg cgtggtggca ggcgcctgta agtcctagct
1801 actccggagg ctgaggcagg agaatggcgt gaacccggga ggcggagctt gcagtgagca
1861 gagatggcac cactgcactc cagcctgggc gacagagcaa gactccgtct caaaaaaaa
1921 aaaaaaaaaa gcaactgcca ctagcactgg gaaattaaaa tattcataga gccaagttat
1981 ctttgcatgg ctgattagca gttcatattc ctccccagaa ttgcaagatc ctgaagggct
2041 taagtgaaat ttactctgat gagtaacttg cttatcaatt catgaagctc agagggtcat
2101 caggctgggg tgggggccgg tgggaagcag gtggtcagta atcaagttca gaggatgggc
2161 acactcatac atgaagctga cttttccagg acagccaggt caccaagcca gatatgtctg
2221 tgttctcttt gcagtactga agataacagc cagggaggac aagcagggct gggcctaggg
2281 acagactgca agaggctcct gtcccctggg gtctctgctg catttgtgtc atcttgttgc
2341 catggagttg tgatcatccc atctaagctg cagcttcctg tcaacacttc tcacatctta
2401 tgctaactgt agataaagtg gtttgatggt gacttcctcg cctctcccac cccatgcatt
2461 aaattttaag gtagaacctc acctgttact gaaagtggtt tgaaagtgaa taaacttcag
2521 caccatggac agaagacaaa tgcctgcgtt ggtgtgcttt ctttcttctt gggaagagaa
2581 ttc.
```

SEQ ID NO:16 is the amino acid sequence for the mouse preproANP peptide:

(SEQ ID NO: 16)
MGSFSITLGF FLVLAFWLPG HIGANPVYSA VSNTDLMDFK

NLLDHLEEKM PVEDEVMPPQ ALSEQTEEAG AALSSLPEVP

PWTGEVNPPL RDGSALGRSP WDPSDRSALL KSKLRALLAG

PRSLRRSSCF GGRIDRIGAQ SGLGCNSFRY RR.

SEQ ID NO: 17 is the genetic sequence for the mouse pre-proANP peptide wherein the coding sequence starts at nucleic acid molecule position 81 and ends at nucleic acid molecule position 539:

```
                                                         (SEQ ID NO: 17)
  1 caaaagctga gagagagaga gaaagaaacc agagtgggca gagacagcaa acatcagatc
 61 gtgccccgac ccacgccagc atgggctcct tctccatcac cctgggcttc ttcctcgtct
121 tggccttttg gcttccaggc catattggag caaatcctgt gtacagtgcg gtgtccaaca
181 cagatctgat ggatttcaag aacctgctag accacctgga ggagaagatg ccggtagaag
241 atgaggtcat gccccgcag gccctgagtg agcagactga ggaagcaggg gccgcactta
301 gctccctccc cgaggtgcct ccctggactg gggaggtcaa cccacctctg agagacggca
361 gtgctctagg gcgcagcccc tgggacccct ccgatagatc tgccctcttg aaaagcaaac
421 tgagggctct gctcgctggc cctcggagcc tacgaagatc cagctgcttc ggggggtagga
481 ttgacaggat tggagcccag agtggactag gctgcaacag cttccggtac cgaagataac
541 agccaaggag gaaaaggcag tcgattctgc ttgagcagat cgcaaaagat cctaagccct
601 tgtggtgtgt cacgcagctt ggtcacattg ccactgtggc gtggtgaaca ccctcctgga
661 gctgcggctt cctgccttca tctatcacga tcgatgttaa atgtagatga gtggtctagt
721 ggggtcttgc ctctcccact ctgcatatta aggtagatcc tcacccttt cagaaagcag
781 ttggaaaaaa aaaaaagaa taaacttcag caccaaggac agacgccgag gccctgatgt
841 gcttctttgg cttctgccct cagttctttg ctctccc.
```

SEQ ID NO:18 is amino acid sequence of human natriuretic peptide receptor-A (NPR-A):

```
                                                         (SEQ ID NO: 18)
MPGPRRPAGSRLRLLLLLLLPPLLLLLRGSHAGNLTVAVVLPLANTSYPW

SWARVGPAVELALAQVKARPDLLPGWTVRTVLGSSENALGVCSDTAAPLA

AVDLKWEHNPAVFLGPGCVYAAAPVGRFTAHWRVPLLTAGAPALGFGVKD

EYALTTRAGPSYAKLGDFVAALHRRLGWERQALMLYAYRPGDEEHCFFLV

EGLFMRVRDRLNITVDHLEFAEDDLSHYTRLLRTMPRKGRVIYICSSPDA

FRTLMLLALEAGLCGEDYVFFHLDIFGQSLQGGQGPAPRRPWERGDGQDV

SARQAFQAAKIITYKDPDNPEYLEFLKQLKHLAYEQFNFTMEDVLVNTIP

ASFHDGLLLYIQAVTETLAHGGTVTDGENITQRMWNRSFQGVTGYLKIDS

SGDRETDFSLWDMDPENGAFRVVLNYNGTSQELVAVSGRKLNWPLGYPPP

DIPKCGFDNEDPACNQDHLSTLEVLALVGSLSLLGILIVSFFIYRKMQLE

KELASELWRVRWEDVEPSSLERHLRSAGSRLTLSGRGSNYGSLLTTEGQF

QVFAKTAYYKGNLVAVKRVNRKRIELTRKVLFELKHMRDVQNEHLTRFVG

ACTDPPNICILTEYCPRGSLQDILENESITLDWMFRYSLTNDIVKGMLFL
```

```
                           -continued
HNGAICSHGNLKSSNCVVDGRFVLKITDYGLESFRDLDPEQGHTVYAKKL

WTAPELLRMASPPVRGSQAGDVYSFGIILQEIALRSGVFHVEGLDLSPKE

IIERVTRGEQPPFRPSLALQSHLEELGLLMQRCWAEDPQERPPFQQIRLT

LRKFNRENSSNILDNLLSRMEQYANNLEELVEERTQAYLEEKRKAEALLY

QILPHSVAEQLKRGETVQAEAFDSVTIYFSDIVGFTALSAESTPMQVVTL

LNDLYTCFDAVIDNFDVYKVETIGDAYMVVSGLPVRNGRLHACEVARMAL

ALLDAVRSFRIRHRPQEQLRLRIGIHTGPVCAGVVGLKMPRYCLFGDTVN

TASRMESNGEALKIHLSSETKAVLEEFGGFELELRGDVEMKGKGKVRTYW

LLGERGSSTRG.
```

(NCBI ACCESSION NO. NM_000906; Airhart N. et al. *J. Biol. Chem.*, 2003, 278(40):38693-38698; Pitzalis M. V. et al., *J. Hypertens.*, 2003, 21(8):1491-1496; Mokentin J. D. *J. Clin. Invest.*, 2003, 111(9):1275-1277; De L. et al., *J. Biol. Chem.*, 2003, 278(13):11159-11166; Knowles J. W. et al., *Hum. Genet.* 2003, 12(1):62-70; Pandy K. N. et al., *J. Biol. Chem.* 2002, 277(7):4618-4627).

SEQ ID NO:19 is the nucleotide coding sequence for human natriuretic peptide receptor-A (NPR-A):

```
                                                         (SEQ ID NO: 19)
    ggttccctcc ggatagccgg agacttgggc cggccggacg cccttctgg cacactccct
 61 ggggcaggcg ctcacgcacg ctacaaacac acactcctct ttcctccctc gcgcgccctc
121 tctcatcctt cttcacgaag cgctcactcg cacccttct ctctctctct ctctctctaa
181 cacgcacgca cactcccagt tgttcacact cgggtcctct ccagcccgac gttctcctgg
241 cacccacctg ctccgcgcg ccctgcgcgc cccctcggt cgcgccctt gcgctctcgg
301 cccagaccgt cgcagctaca gggggcctcg agccccgggg tgagcgtccc cgtcccgctc
361 ctgctccttc ccatagggac gcgcctgatg cctgggaccg gccgctgagc ccaagggac
```

-continued

```
 421 cgaggaggcc atggtaggag cgctcgcctg ctgcggtgcc cgctgaggcc atgccggggc
 481 cccggcgccc cgctggctcc cgcctgcgcc tgctcctgct cctgctgctg ccgccgctgc
 541 tgctgctgct ccggggcagc cacgcgggca acctgacggt agccgtggta ctgccgctgg
 601 ccaataccct gtacccctgg tcgtgggcgc gcgtgggacc cgccgtggag ctggccctgg
 661 cccaggtgaa ggcgcgcccc gacttgctgc cgggctggac ggtccgcacg gtgctgggca
 721 gcagcgaaaa cgcgctgggc gtctgctccg caccgcagc gccctggcc gcgtggacc
 781 tcaagtggga gcacaacccc gctgtgttcc tgggccccgg ctgcgtgtac gccgccgccc
 841 cagtgggcg cttcaccgcg cactggcggg tcccgctgct gaccgccggc gccccggcgc
 901 tgggcttcgg tgtcaaggac gagtatgcgc tgaccacccg cgcggggccc agctacgcca
 961 agctggggga cttcgtggcg cgcgctgcacc gacggctggg ctgggagcgc caagcgctca
1021 tgctctacgc ctaccggccg ggtgacgaag agcactgctt cttcctcgtg gaggggctgt
1081 tcatgcgggt ccgcgaccgc ctcaatatta cggtggacca cctggagttc gccgaggacg
1141 acctcagcca ctacaccagg ctgctgcgga ccatgccgcg caaaggccga gttatctaca
1201 tctgcagctc ccctgatgcc ttcagaaccc tcatgctcct ggccctggaa gctggcttgt
1261 gtggggagga ctacgttttc ttccacctgg atatctttgg caaagcctg caaggtggac
1321 agggccctgc tccccgcagg ccctgggaga gggggatgg gcaggatgtc agtgcccgcc
1381 aggcctttca ggctgccaaa atcattacat ataaagaccc agataatccc gagtacttgg
1441 aattcctgaa gcagttaaaa cacctggcct atgagcagtt caacttcacc atggaggatg
1501 tcctggtgaa caccatccca gcatccttcc acgacgggct cctgctctat atccaggcag
1561 tgacggagac tctggcacat gggggaactg ttactgatgg ggagaacatc actcagcgga
1621 tgtggaaccg aagctttcaa ggtgtgacag gatacctgaa aattgatagc agtggcgatc
1681 gggaaacaga cttctcccctc tgggatatgg atcccgagaa tggtgccttc agggttgtac
1741 tgaactacaa tgggacttcc caagagctgg tggctgtgtc ggggcgcaaa ctgaactggc
1801 ccctggggta ccctcctcct gacatcccca atgtggcttt gacaacgaa gacccagcat
1861 gcaaccaaga tcaccttttcc accctggagg tgctggcttt ggtgggcagc ctctccttgc
1921 tcggcattct gattgtctcc ttcttcatat acaggaagat gcagctggag aaggaactgg
1981 cctcggagct gtggcgggtg cgctgggagg acgttgagcc cagtagcctt gagaggcacc
2041 tgcggagtgc aggcagccgg ctgacccctga gcgggagagg ctccaattac ggctccctgc
2101 taaccacaga gggccagttc caagtctttg ccaagacagc atattataag ggcaacctcg
2161 tggctgtgaa acgtgtgaac cgtaaacgca ttgagctgac acgaaaagtc ctgtttgaac
2221 tgaagcatat gcgggatgtg cagaatgaac acctgaccag gtttgtggga gcctgcaccg
2281 accccccaa tatctgcatc ctcacagagt actgtccccg tgggagcctg caggacattc
2341 tggagaatga gagcatcacc ctggactgga tgttccggta ctcactcacc aatgacatcg
2401 tcaagggcat gctgtttcta cacaatgggg ctatctgttc ccatgggaac ctcaagtcat
2461 ccaactgcgt ggtagatggg cgctttgtgc tcaagatcac cgactatggg ctggagagct
2521 tcagggacct ggacccagag caaggacaca ccgtttatgc caaaaagctg tggacggccc
2581 ctgagctcct gcgaatggct tcaccccctg tgcgggctc ccaggctggt gacgtataca
2641 gctttgggat catccttcag gagattgccc tgaggagtgg gtcttccac gtggaaggtt
2701 tggacctgag ccccaaagag atcatcgagc gggtgactcg ggtgagcag ccccccttcc
2761 ggccctccct ggccctgcag agtcacctgg aggagttggg gctgctcatg cagcggtgct
2821 gggctgagga cccacaggag aggccaccat tccagcagat ccgcctgacg ttgcgcaaat
```

```
-continued
2881 ttaacaggga gaacagcagc aacatcctgg acaacctgct gtcccgcatg gagcagtacg 2941 cgaacaatct ggaggaactg gtggaggagc ggacccaggc atacctggag gagaagcgca 3001 aggctgaggc cctgctctac cagatcctgc ctcactcagt ggctgagcag ctgaagcgtg 3061 gggagacggt gcaggccgaa gcctttgaca gtgttaccat ctacttcagt gacattgtgg 3121 gtttcacagc gctgtcggcg gagagcacgc ccatgcaggt ggtgaccctg ctcaatgacc 3181 tgtacacttg ctttgatgct gtcatagaca actttgatgt gtacaaggtg gagacaattg 3241 gcgatgccta catggtggtg tcagggctcc ctgtgcggaa cgggcggcta cacgcctgcg 3301 aggtagcccg catggccctg gcactgctgg atgctgtgcg ctccttccga atccgccacc 3361 ggccccagga gcagctgcgc ttgcgcattg gcatccacac aggacctgtg tgtgctggag 3421 tggtgggact gaagatgccc cgttactgtc tctttgggga tacagtcaac acagcctcaa 3481 gaatggagtc taatggggaa gccctgaaga tccacttgtc ttctgagacc aaggctgtcc 3541 tggaggagtt tggtggtttc gagctggagc ttcgagggga tgtagaaatg aagggcaaag 3601 gcaaggttcg gacctactgg ctccttgggg agaggggggag tagcacccga ggctgacctg 3661 cctcctctcc tatccctcca cacctcccct accctgtgcc agaagcaaca gaggtgccag 3721 gcctcagcct cacccacagc agcccatcg ccaaaggatg gaagtaattt gaatagctca 3781 ggtgtgctta ccccagtgaa gacaccagat aggacctctg agaggggact ggcatggggg 3841 gatctcagag cttacaggct gagccaagcc cacggccatg cacaggagaca ctcacacagg 3901 cacacgcacc tgctctccac ctggactcag gccgggctgg gctgtggatt cctgatcccc 3961 tccctcccc atgctctcct ccctcagcct tgctaccctg tgacttactg ggaggagaaa 4021 gagtcacctg aaggggaaca tgaaaagaga ctaggtgaag agagggcagg ggagcccaca 4081 tctggggctg gcccacaata cctgctcccc cgacccctc cacccagcag tagacacagt 4141 gcacagggga gaagaggggt ggcgcagaag ggttgggggc ctgtatgcct tgcttctacc 4201 atgagcagag acaattaaaa tctttattcc aaaaaaaaaa aaaaaa
```

(NCBI ACCESSION NO. NM_000906; Airhart N. et al., *J. Biol. Chem.*, 2003, 278(40):38693-38698; Pitzalis M. V. et al., *J. Hypertens.*, 2003, 21(8):1491-1496; Mokentin J. D. *J. Clin. Invest.*, 2003, 111(9):1275-1277; De L. et al., *J. Biol. Chem.*, 2003, 278(13):11159-11166; Knowles J. W. et al., *Hum. Genet.*, 2003, 12(1):62-70; Pandy K. N. et al. *J. Biol. Chem.*, 2002, 277(7):4618-4627).

SEQ ID NO:20 is amino acid sequence of the human atrial natriuretic peptide clearance receptor precursor (ANP-C; also referred to as NPR-C, NPRC, and atrial natriuretic peptide C-type receptor):

```
                                         (SEQ ID NO: 20)
MPSLLVLTFS PCVLLGWALL AGGTGGGVG GGGGGAGIGG

GRQEREALPP QKIEVLVLLP QDDSYLFSLT RVRPAIEYAL

RSVEGNGTGR RLLPPGTRFQ VAYEDSDCGN RALFSLVDRV

AAARGAKPDL ILGPVCEYAA APVARLASHW DLPMLSAGAL

AAGFQHKDSE YSHLTRVAPA YAKMGEMMLA LFRHHHWSRA

ALVYSDDKLE RNCYFTLEGV HEVFQEEGLH TSIYSFDETK

DLDLEDIVRN IQASERVVIM CASSDTIRSI MLVAHRHGMT

SGDYAFFNIE LFNSSSYGDG SWKRGDKHDF EAKQAYSSLQ

TVTLLRTVKP EFEKFSMEVK SSVEKQGLNM EDYVNMFVEG

-continued
FHDAILLYVL ALHEVLRAGY SKKDGGKIIQ QTWNRTFEGI

AGQVSIDANG DRYGDFSVIA MTDVEAGTQE VIGDYFGKEG

RFEMRPNVKY PWGPLKLRID ENRIVEHTNS SPCKSSGGLE

ESAVTGIVVG ALLGAGLLMA FYFFRKKYRI TIERRTQQEE

SNLGKHRELR EDSIRSHFSV A
```

(NCBI ACCESSION NO. P17342; Lowe D. G. e al., *Nucleic Acids Res.*, 1990, 18(11):3412; Porter J. G. et al., *Biochem. Biophys. Res. Commun.*, 1990, 171(2):796-803; Stults J. T. et al., *Biochemistry*, 1994, 33(37):11372-11381).

SEQ ID NO: 21 is an siRNA specific for NPR-A (human).

```
tat tac ggt gga cca cct gtt caa gag aca ggt ggt cca ccg taa tat ttttt
```

SEQ ID NO: 22 is an siRNA specific for NPR-A (human).

```
aga att cca gaa acg cag ctt caa gag agc tgc gtt tct gga att ctt ttttt
```

DETAILED DISCLOSURE

The present invention pertains to methods for reducing natriuretic peptide receptor-A (also known in the art as NPRA, NPR-A, and guanylate cyclase A) activity in vitro or in viva. In one aspect, the method of the invention may be used for treating inflammatory and cell proliferation disorders, such as cancer. In another aspect, the present invention concerns methods for identifying agents useful for treating inflammatory and cell proliferation disorders by determining whether the candidate agent reduces activity of the natriuretic peptide receptor-A (also known in the art as NPRA, NPR-A, and guanylate cyclase A) in vitro and/or in vivo (also referred to herein as the diagnostic method or assay of the invention).

As used herein, an "inflammatory disorder" includes those conditions characterized by an aberrant increase in one or more of the following: IL-6, IL-1 beta, TNF-alpha, IL-8, eosinophil production, neutrophil production, release of histamines, proliferants, hyperplasia, and cell adhesion molecule expression. As used herein, a "cell proliferation disorder" is characterized by one or more of the following: uncontrolled proliferation, a high mitogenic index, over-expression of cyclin D1, cyclin B1, expression of an oncogene such as c-jun and/or c-fos, aberrant activation of NFκB and/or ERK (extracellular receptor kinase), and matrix metalloproteinase expression (such as MMP-2 and/or MMP-9).

In one embodiment, the inflammatory disorder and cell proliferation disorder is not one that is amenable to effective treatment by administration of a vasodilator. In one embodiment, the inflammatory disorder and cell proliferation disorder is not a cardiovascular disorder (such as hypertension or stroke). In another embodiment, the inflammatory disorder and cell proliferation disorder is not a disorder of the central nervous system (such as Alzheimer's disease or other dementia). In another embodiment, the inflammatory disorder and cell proliferation disorder is not kidney failure or other kidney disorder.

The agent used to reduce NPR-A activity in vitro or in vivo can be virtually any substance and can encompass numerous chemical classes, including organic compounds or inorganic compounds. Preferably, an effective amount of the agent is administered to the cells with a pharmaceutically acceptable carrier. The agent may be a substance such as genetic material, protein, lipid, carbohydrate, small molecules, a combination of any of two or more of foregoing, or other compositions. The agent may be naturally occurring or synthetic, and may be a single substance or a mixture. The agent can be obtained from a wide variety of sources including libraries of compounds. The agent can be or include, for example, a polypeptide, peptidomimetic, amino acid(s), amino acid analog(s), function-blocking antibody, polynucleotide(s), polynucleotide analog(s), nucleotide(s), nucleotide analog(s), or other small molecule(s). A polynucleotide may encode a polypeptide that potentially reduces NPR-A activity within the cell, or the polynucleotide may be a short interfering RNA (siRNA), a hairpin RNA (shRNA), antisense oligonucleotide, ribozyme, or other polynucleotide that targets an endogenous or exogenous gene for silencing of gene expression and potentially NPR-A activity within the cell.

In one embodiment, the agent used to reduce NPR-A activity is an interfering RNA specific for NPR-A mRNA, preferably human NPR-A mRNA. Interfering RNA is capable of hybridizing with the mRNA of a target gene and reduce and/or eliminate translation through the mechanism of RNA interference. Examples of such interfering RNA include SEQ ID NO:21 and SEQ ID NO:22, which were determined to have a relatively high probably of reducing NPR-A activity using an siRNA Target Finder program (AMBION) and in accordance with published guidelines (Tuschl T., *Nature Biotechnol.*, 2002, 20:446448). As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) that is capable of directing or mediating RNA interference. In one embodiment, the siRNA is between about 10-50 nucleotides (or nucleotide analogs). Optionally, a polynucleotide (e.g., DNA) encoding the siRNA may be administered to cells in vitro or in vivo, such as in a vector, wherein the DNA is transcribed.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The scientific literature is replete with reports of endogenous and exogenous gene expression silencing using siRNA, highlighting their therapeutic potential (Gupta, S. et al. PNAS, 2004, 101:1927-1932; Takaku, H. *Antivir Chem. Chemother*, 2004, 15:57-65; Pardridge, W. M. *Expert Opin. Biol. Ther.*, 2004, 4:1103-1113; Zheng, B. J. *Antivir. Ther.*, 2004, 9:365-374; Shen, W. G. *Chin., Med. J. (Engl)*, 2004, 117:1084-1091; Fuchs, U. et al. *Curr. Mol. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., *Methods Enzymol.*, 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, 2004, July, 4(7):1103-1113), each of which is incorporated herein by reference in its entirety.

In another embodiment, the decrease in NPR-A activity (e.g., a reduction in NPR-A expression) may be achieved by administering an analogue of ANP (e.g., ANP4-23) or non-peptide antagonists (e.g., HS-142-1; Rutherford et al., *Br. J. Pharmacol.*, 1994, 113:931-939; El-Ayoubi et al., *Br. J. Pharmacol.*, 2005, Feb. 7, Epub ahead of print; Delport C. et al., *Eur. J. Pharmacol.*, 1992, 224(2-3):183-188; Ohyama Y. et al., *Biochem. Biophys. Res. Commun.*, 1992, 189(1):336-342). In another embodiment, the agent is an anti-human NPR-A function-blocking antibody (preferably, humanized), or soluble NPR-A or NPR-C (as a receptor decoy). Other examples of agents include NPR-A antagonists that specifically inhibit cGMP-dependent protein kinase (PKG) such as A71915 and KT5823 (Pandey K. N. et al., *Biochemical and Biophysical Research Communications*, 2000, 271:374-379).

The methods of the invention may include further steps. In some embodiments, a subject with the relevant inflammatory disorder and/or cell proliferation disorder is identified or a patient at risk for the disorder is identified. A patient may be someone who has not been diagnosed with the disease or condition (diagnosis, prognosis, and/or staging) or someone diagnosed with disease or condition (diagnosis, prognosis, monitoring, and/or staging), including someone treated for the disease or condition (prognosis, staging, and/or monitoring). Alternatively, the person may not have been diagnosed with the disease or condition but suspected of having the disease or condition based either on patient history or family history, or the exhibition or observation of characteristic symptoms.

In one aspect, the therapeutic method of the invention involves administering a natriuretic hormone peptide (NP), or a fragment, homolog or variant thereof, or a nucleic acid sequence encoding an NP, or a fragment, homolog, or variant thereof, to a patient. The present inventor has demonstrated that a prolonged, substantial reduction of tumor burden in lungs can be achieved by intranasal delivery of pDNA-encoding a peptide comprising amino acid residues 73 to 102 (NP73-102). Without being bound by theory, the NP decreased viability due to the induction of apoptosis in a lung adenocarcinoma cell line A549 cell, and can reduce tumorigenesis and metastasis in a number of cancers.

In specific embodiments, the peptides used in the subject invention comprise at least one amino acid sequence selected from the group consisting of $NP_{1-30}$, $NP_{31-67}$, $NP_{79-98}$, and $NP_{73-102}$, (SEQ ID NO:1, SEQ ID NO:2, SEQ ID NO:3, and SEQ ID NO:5, respectively), SEQ ID NO:6, or a biologically active fragment or homolog thereof. In some embodiments, a combination of NP or NP-encoding nucleic acid sequences is utilized. In one embodiment, the peptide utilized does not consist of the amino acid sequence of $NP_{99-126}$ (SEQ ID NO: 4).

In another aspect, the therapeutic method of the invention involves administering an agent that reduces activity of the natriuretic peptide receptor-A (also known in the art as NPRA, NPR-A, and guanylate cyclase A) to a patient, wherein the agent is administered in an amount effective to reduce receptor (NPR-A) activity. NPR-A activity can be determined, for example, by one or more of the following biological parameters: production/accumulation of cGMP, expression of the NPR-A (transcription or translation), and/or cellular internalization of the NPR-A.

According to the gene therapy method of the present invention, the NP-encoding nucleic acid sequence is administered locally at the target site (e.g., at the site of cancer or precancer), or systemically to the patient. In order to treat cancer of the lung, for example, the NP-encoding nucleic acid sequence is preferably administered to the airways of the patient, e.g., nose, sinus, throat and lung, for example, as nose drops, by nebulization, vaporization, or other methods known in the art. More preferably, the nucleic acid sequence encoding NP is administered to the patient orally or intranasally, or otherwise intratracheally. For example, the nucleic acid sequence can be inhaled by the patient through the oral or intranasal routes, or injected directly into tracheal or bronchial tissue.

In specific embodiments, the nucleic acid sequences used in the subject invention encode at least one amino acid sequence selected from the group consisting of $NP_{1-30}$, $NP_{31-67}$, $NP_{79-98}$, $NP_{99-126}$, and $NP_{73-102}$, (SEQ ID NO:1, SEQ ID NO:2, SEQ ID NO:3, SEQ ID NO:4, and SEQ ID NO:5, respectively), SEQ ID NO:6, or a biologically active fragment or homolog of any of the foregoing.

Preferably, the nucleic acid sequence encoding the NP is administered with a nucleic acid sequence that is operatively linked with the NP-encoding nucleic acid sequence and operates as a regulatory sequence. For example, the regulatory sequence can be a promoter sequence that controls transcription and drives expression of the NP-encoding nucleic acid sequence at the desired site, such as at, or adjacent to, the patient's respiratory epithelial cells. The promoter can be a constitutive or inducible promoter to allow selective transcription. The promoter can be a vertebrate or viral promoter. Optionally, enhancers may be used to obtain desired transcription levels. An enhancer is generally any non-translated nucleic acid sequence that works contiguously with the coding sequence (in cis) to change the basal transcription level dictated by the promoter.

The NP-encoding nucleic acid sequences used in the methods, expression vectors, and pharmaceutical compositions of the present invention are preferably isolated. According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule or sequence useful in the present composition can include DNA, RNA, or any derivatives of either DNA or RNA. An isolated nucleic acid molecule or sequence can be double stranded (i.e., containing both a coding strand and a complementary strand) or single stranded.

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules, and combinations thereof.

Although the phrase "nucleic acid molecule" primarily refers to the physical nucleic acid molecule and the phrase "nucleic acid sequence" primarily refers to the sequence of nucleotides on the nucleic acid molecule, the two phrases are used interchangeably herein. As used herein, a "coding" nucleic acid sequence refers to a nucleic acid sequence that encodes at least a portion of a peptide or protein (e.g., a portion of an open reading frame), and can more particularly refer to a nucleic acid sequence encoding a peptide or protein which, when operatively linked to a transcription control sequence (e.g., a promoter sequence), can express the peptide or protein.

The nucleotide sequences encoding NP used in the subject invention include "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acids to the polynucleotides of the invention provide for "homologous" or "modified" nucleotide sequences. In various embodiments, "homologous" or "modified" nucleic acid sequences have substantially the same biological or serological activity as the native (naturally occurring) natriuretic peptide. A "homologous" or "modified" nucleotide sequence will also be understood to mean a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive).

The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous nucleotide and amino acid sequences include mammalian homologs of the human NP sequences.

The NP homologs include peptides containing, as a primary amino acid sequence, all or part of an exemplified NP polypeptide sequence. The NP homologs thus include NP polypeptides having conservative substitutions, i.e., altered sequences in which functionally equivalent amino acid residues are substituted for residues within the sequence resulting in a peptide which is biologically active. For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 1). Conservative substitutions also include substitutions by amino acids having chemically modified side chains which do not eliminate the biological activity of the resulting NP homolog.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Both protein and nucleic acid sequence homologies may be evaluated using any of the variety of sequence comparison algorithms and programs known in the art. Such algorithms and programs include, but are by no means limited to, TBLASTN, BLASTP. FASTA, TFASTA, and CLUSTALW (Pearson and Lipman *Proc. Natl. Acad. Sci. USA,* 1988, 85(8):2444-2448; Altschul et al. *J. Mol. Biol.,* 1990, 215(3): 403-410; Thompson et al. *Nucleic Acids Res.,* 1994, 22(2): 4673-4680; Higgins et al. *Methods Enzymol.,* 1996, 266:383-402; Altschul et al. *J. Mol. Biol.,* 1990, 215(3):403-410; Altschul et al. *Nature Genetics,* 1993, 3:266-272).

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; York (1988); Biocomputing: Informatics and Genome Projects, Smith, D. W., ed., Academic Press, New York, 1993; York (1993); Computer Analysis of Sequence Data, Part 1, Griffin, A. M., and Griffin, H. G., eds., Humana Press, New Jersey, 1994; Jersey (1994); Sequence Analysis in Molecular Biology, von Heinje, G., Academic Press, 1987; Press (1987); Sequence Analysis Primer, Gribskov, M. and Devereux, J., eds., M. Stockton Press, New York, 1991; York (1991); and Carillo et al., SIAM J. Applied Math., 48:1073 (1988).

The methods, pharmaceutical compositions, and vectors of the present invention can utilize biologically active fragments of nucleic acid sequences encoding the 126-amino acid atrial natriuretic factor (ANF) prohormone, such as nucleic acid sequences encoding $NP_{1-0}$, $NP_{31-67}$, $NP_{79-98}$, $NP_{99-126}$, and $NP_{73-102}$, (SEQ ID NO:1, SEQ ID NO:2, SEQ ID NO:3, SEQ ID NO:4, and SEQ ID NO:5, respectively), SEQ ID NO:6, and including biologically active fragments of the nucleic acid sequences encoding SEQ ID NO:1, SEQ ID NO:2, SEQ ID NO:3, SEQ ID NO:4, SEQ ID NO:5, and SEQ ID NO:6.

Representative fragments of the nucleotide sequences according to the invention will be understood to mean any polynucleotide fragment having at least 8 or 9 consecutive nucleotides, preferably at least 12 consecutive nucleotides, and still more preferably at least 15 or at least 20 consecutive nucleotides of the sequence from which it is derived, with retention of biological activity as described herein. The upper limit for such fragments is one nucleotide less than the total number of nucleotides found in the full-length sequence (or, in certain embodiments, of the full length open reading frame (ORF) identified herein).

In other embodiments, fragments can comprise consecutive nucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and up to one nucleotide less than the full length ANF prohormone. In some embodiments, fragments comprise biologically active fragments of SEQ ID NO:1, SEQ ID NO:2, SEQ ID NO:3, SEQ ID NO:4, SEQ ID NO:5, or SEQ ID NO:6.

It is also well known in the art that restriction enzymes can be used to obtain biologically active fragments of the nucleic acid sequences, such as those encoding SEQ ID NO:1, SEQ ID NO:2, SEQ ID NO:3, SEQ ID NO:4, SEQ ID NO:5, and SEQ ID NO:6. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual,* Cold Spring Harbor Laboratory, New York; Wei et al., *J. Biol. Chem.,* 1983, 258:13006-13512.

The methods and pharmaceutical compositions of the present invention can utilize amino acid sequences that are biologically active fragments of the 126-amino acid atrial natriuretic factor (ANF) prohormone, such as $NP_{1-30}$, $NP_{31-67}$, $NP_{79-98}$, $NP_{99-126}$, and $NP_{73-102}$ (SEQ ID NO:1, SEQ ID NO:2, SEQ ID NO:3, SEQ ID NO:4, and SEQ ID NO:5, respectively), SEQ ID NO:6, and including biologically active fragments of SEQ ID NO:1. SEQ ID NO:2, SEQ ID NO:3, SEQ ID NO:4, SEQ ID NO:5, and SEQ ID NO:6.

Representative fragments of the polypeptides according to the invention will be understood to mean any polypeptide fragment having at least 8 or 9 consecutive amino acids, preferably at least 12 amino acids, and still more preferably at least 15 or at least 20 consecutive amino acids of the polypeptide sequence from which it is derived, with retention of biological activity as described herein. The upper limit for such fragments is one amino acid less than the total number of amino acids found in the full-length sequence.

In other embodiments, fragments of the polypeptides can comprise consecutive amino acids of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, and up to one amino acid less than the full-length ANF prohormone. Fragments of polypeptides can be any portion of the full-length ANF prohormone amino acid sequence (including human or non-human mammalian homologs of the ANF prohormone) that exhibit biological activity as described herein, e.g., a C-terminally or N-terminally truncated version of the ANF prohormone, or an intervening portion of the ANF prohormone. In some embodiments, fragments comprise biologically active fragments of SEQ ID NO:1, SEQ ID NO:2, SEQ ID NO:3, SEQ ID NO:4, SEQ ID NO:5, and SEQ ID NO:6.

The present invention can be practiced using other biologically equivalent forms of ANF fragments or homologs thereof as can be appreciated by the sequence comparison below. Sequence similarities between mouse and human forms of ANP are shown where areas of conservation are clearly seen. NCBI BLAST Comparison of mouse (Query) to human (Sbjct) ANP a.a. sequences.

in vivo directly (i.e., as a polypeptide), or the fusion polypeptide may be administered as a polynucleotide encoding the fusion polypeptide with an operably linked promoter sequence. See, for example, Wang W. et al., "Albubnp, a Recombinant B-type Natriuretic Peptide and Human Serum Albumin Fusion Hormone, as a Long-Term Therapy of Congestive Heart Failure", Pharmaceutical Research, Springer Science and Business Media B. V., Formerly Kluwer Academic Publishers B. V., ISSN:0724-8741, volume 21, Number 11, November, 2004, pages 2105-2111.

The NP includes all hydrates and salts of natriuretic peptides that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of NP may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The NP of the invention can be prepared by well-known synthetic procedures. For example, the polypeptides can be

```
Query:    1 MGSFSIT-LGFFLVLAFWLPGHIGANPVYSAVSNTDLMDFKNLLDHLEEKMPVEDEVMPP
            M SFS T + F L+LAF L G ANP+Y+AVSN DLMDFKNLLDHLEEKMP+EDEV+PP
Sbjct:    1 MSSFSTTTVSFLLLLAFQLLGQTRANPMYNAVSNADLMDFKNLLDHLEEKMPLEDEVVPP Query:   60 QALSEQTEEAGAALSSLPEVPPWTGEVNPPLRDGSALGRSPWDPSDXXXXXXXXXXXXXX
            Q LSE EEAGAALS LPEVPPWTGEV+P RDG ALGR PWD SD
Sbjct:   61 QVLSEPNEEAGAALSPLPEVPPWTGEVSPAQRDGGALGRGPWDSSDRSALLKSKLRALLT Query:  120 GPRSLRRSSCFGGRIDRIGAQSGLGCNSFRY        150
            PRSLRRSSCFGGR+DRIGAQSGLGCNSFRY
Sbjct:  121 APRSLRRSSCFGGRMDRIGAQSGLGCNSFRY        151
```

The NP utilized in the subject invention can be peptide derivatives, such as those disclosed in U.S. Patent Publication No. 2004/0266673 (Bakis et al.), which is incorporated herein by reference in its entirety. These NP derivates include an NP and a reactive entity coupled to the NP peptide. The reactive entity is able to covalently bond with a functionality on a blood component. Such NP derivatives are reported to have an extended half-life in vivo. The NP utilized in the subject invention can be a modified NP, such as those described in U.S. Patent Publication No. 2004/0002458 (Seilhamer et al.) and U.S. Patent Publication No. 2003/0204063 (Gravel et al.), which are incorporated herein by reference in their entirety.

The NP utilized may be a fusion polypeptide comprising an NP, or Fragment or homolog thereof, and one or more additional polypeptides, such as another NP or a carrier protein, including those described in U.S. Patent Publication No. 2004/0138134 (Golembo et al.), which is incorporated herein by reference in its entirety. The NP utilized may be a chimeric polypeptide, such as those described in U.S. Patent Publication No. 2003/0069186 (Burnett et al.), which is incorporated herein by reference in its entirety. The fusion polypeptide or chimeric polypeptide may be administered to cells in vitro or prepared by the well-known Merrifield solid support method. See Merrifield, *J. Amer. Chem. Soc.*, 1963, 85:2149-2154 and Merrifield (1965) *Science* 150:178-185. This procedure, using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

Alternatively, these peptides can be prepared by use of well-known molecular biology procedures. Polynucleotides, such as DNA sequences, encoding the NP of the invention can be readily synthesized. Such polynucleotides are a further aspect of the present invention. These polynucleotides can be used to genetically engineer eukaryotic or prokaryotic cells, for example, bacteria cells, insect cells, algae cells, plant cells, mammalian cells., yeast cells or fungi cells for synthesis of the peptides of the invention.

For purposes of the present invention, the biological activity attributable to the homologs and fragments of NP and NP-encoding nucleic acid sequences means the capability to prevent or alleviate symptoms associated with inflammatory and/or cell proliferation disorders such as cancer. This biological activity can be mediated by one or more of the following mechanisms: increased production of intracellular Calf concentration (e.g., in epithelial cells), increased production of nitric oxide (O), and decreased activation of transcription factors such as NFκB, ERK1,2 and/or AP1.

The methods of the subject invention also contemplate the administration of cells that have been genetically modified to produce NP, or biologically active fragments, variants, or homologs thereof. Such genetically modified cells can be administered alone or in combinations with different types of cells. Thus, genetically modified cells of the invention can be co-administered with other cells, which can include genetically modified cells or non-genetically modified cells. Genetically modified cells may serve to support the survival and function of the co-administered cells, for example.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides in addition to those encoding NP. A translation initiation codon can be inserted as necessary, making methionine the first amino acid in the sequence. The term "genetic modification" is not intended to include naturally occurring alterations such as that which occurs through natural viral activity, natural genetic recombination, or the like. The genetic modification may confer the ability to produce NP, wherein the cell did not previously have the capability, or the modification may increase the amount of NP endogenously produced by the cell, e.g., through increased expression.

Exogenous nucleic acids and/or vectors encoding NP can be introduced into a cell by viral vectors (retrovirus, modified herpes virus, herpes virus, adenovirus, adeno-associated virus, lentivirus, and the like) or direct DNA transfection (lipofection, chitosan-nanoparticle mediated transfection, calcium phosphate transfection, DEAE-dextran, electroporation, and the like), microinjection, cationic lipid-mediated transfection, transduction, scrape loading, ballistic introduction and infection (see, for example, Sambrook et al. [1989] *Molecular Cloning: A Laboratory Manual*, 2$^{nd}$ Ed., Cold Spring Harbor Laboratory Press, Cold Spring Harbor, N.Y.).

Preferably, the exogenous polynucleotide encoding the NP is operably linked to a promoter sequence that permits expression of the polynucleotide in a desired tissue within the patient. The promoters can be inducible, tissue-specific, or event-specific, as necessary.

The genetically modified cell may be chosen from eukaryotic or prokaryotic systems, for example, bacterial cells (Gram negative or Gram positive), yeast cells, animal cells, plant cells, and/or insect cells using baculovirus vectors, for example. In some embodiments, the genetically modified cell for expression of the nucleic acid sequences encoding NP, are human or non-human mammal cells.

According to the methods of the present invention, NP or polynucleotides encoding NP can be administered to a patient in order to alleviate (e.g., reduce or eliminate) a variety of symptoms associated with cancers, in various stages of pathological development. Treatment with NP or nucleic acid sequences encoding NP is intended to include prophylactic intervention to prevent or reduce cancer cell growth (e.g., tumor growth) and onset of the symptoms associated with cancer cell growth (e.g. tumor growth), such as pain. The nucleic acid sequences and pharmaceutical compositions of the invention can be co-administered (concurrently or consecutively) to a patient with other therapeutic agents useful for treating cancers of the lung, ovarian, breast, as well as melanomas.

Suitable expression vectors for NP include any that are known in the art or yet to be identified that will cause expression of NP-encoding nucleic acid sequences in mammalian cells. Suitable promoters and other regulatory sequences can be selected as is desirable for a particular application. The promoters can be inducible, tissue-specific, or event-specific, as necessary. For example, the cytomegalovirus (CMV) promoter (Boshart et al., *Cell*, 1985, 41:521-530) and SV40 promoter (Subramani et al., *Mol. Cell. Biol.*, 1981, 1:854-864) have been found to be suitable, but others can be used as well. Optionally, the NP-encoding nucleic acid sequences used in the subject invention include a sequence encoding a signal peptide upstream of the NP-encoding sequence, thereby permitting secretion of the NP from a host cell. Also, various promoters may be used to limit the expression of the peptide in specific cells or tissues, such as lung cells.

A tissue-specific and/or event-specific promoter or transcription element that responds to the target microenvironment and physiology can also be utilized for increased transgene expression at the desired site. There has been an immense amount of research activity directed at strategies for enhancing the transcriptional activity of weak tissue-specific promoters or otherwise increasing transgene expression with viral vectors. It is possible for such strategies to provide enhancement of gene expression equal to one or two orders of magnitude, for example (see Nettelbeck et al., Gene Ther., 1998, 5(12):1656-1664 and Qin et al., *Hum. Gene Ther.*, 1997, 8(17):2019-2019, the abstracts of which are submitted herewith for the Examiner's convenience). Examples of cardiac-specific promoters are the ventricular form of MLC-2v promoter (see, Zhu et al., *Mol. Cell Biol.*, 1993, 13:4432-4444, Navankasattusas et al., *Mol. Cell. Biol.*, 1992, 12:1469-1479, 1992) and myosin light chain-2 promoter (Franz et al., *Circ. Res.*, 1993, 73:629-638). The E-cadherin promoter directs expression specific to epithelial cells (Behrens et al., PNAS, 1991, 88:11495-11499), while the estrogen receptor (ER) 3 gene promoter directs expression specifically to the breast epithelium (Hopp et al., *J. Mammary Gland Biol.* Neoplasia, 1998, 3:73-83). The human C-reactive protein (CRP) gene promoter (Ruther et al., Oncogene 8:87-93, 1993) is a liver-specific promoter. An example of a muscle-specific gene promoter is human enolase (ENO3) (Peshavaria et al., *Biochem. J.* 1993, 292(Pt 3):701-704). A number of brain-specific promoters are available such as the thy-1 antigen and gamma-enolase promoters (Vibert et al., *Eur. J. Biochem.* 181:33-39, 1989). The prostate-specific antigen promoter provides prostate tissue specificity (Pang et al., *Gene Ther.*, 1995, 6(11):1417-1426; Lee et al., *Anticancer Res.*, 1996, 16(4A):1805-1811). The surfactant protein B promoter provides lung specificity (Strayer et al., *Am. J. Respir. Cell Mol. Biol.*, 1998, 18(1):1-11). Any of the aforementioned promoters may be selected for targeted or regulated expression of the NP-encoding polynucleotide.

Various viral or non-viral vectors may be used to deliver polynucleotides encoding NP to cells in vitro or in vivo, resulting in expression and production of NP. Tissue-specific promoters or event-specific promoters may be utilized with polynucleotides encoding NP to further optimize and localize expression at target sites, such as within diseased tissues (e.g., cancer cells or tissues containing cancer cells). Robson et al. review various methodologies and vectors available for delivering and expressing a polynucleotide in vivo for the purpose of treating cancer (Robson, T. Hirst, D. G., *J. Biomed. and Biotechnol.*, 2003, 2003(2):110-137). Among the various targeting techniques available, transcriptional targeting using tissue-specific and event-specific transcriptional control elements is discussed. For example, Table 1 at page 112 of the Robson et al. publication lists several tissue-specific promoters useful in cancer therapy. Tables 2-4 of the Robson et al. publication list tumor-specific promoters, tumor environment-specific promoters, and exogenously controlled inducible promoters, many of which were available at the time the patent application was filed. The successful delivery and expression of the p53 tumor suppressor gene in vivo has been documented (Horowitz, *J. Curr. Opin. Mol. Ther.*, 1999, 1(4): 500-509; Von Gruenigen, V. F. et al. *Int. J. Gynecol. Cancer*, 1999, 9(5):365-372; Fujiwara, T. et al., *Mol. Urol*, 2000, 4(2):51-54, respectively).

Many techniques for delivery of drugs and proteins are available in the art to reduce the effects of enzymatic degradation, to facilitate cell uptake, and to reduce any potential toxicity to normal (undiseased) cells, etc. Such methods and reagents can be utilized for administration of NP to cells in vitro or in vivo. For example, peptides known as "cell penetrating peptides" (CPP) or "protein transduction domains" (PTD) have an ability to cross the cell membrane and enter the cell. PTDs can be linked to a cargo moiety such as a drug, peptide, or full-length protein, and can transport the moiety across the cell membrane. One well characterized PTD is the human immunodeficient virus (HIV)-1 Tat peptide (see, for example, Frankel et al., U.S. Pat. Nos. 5,804,604; 5,747,641; 6,674,980; 5,670,617; and 5,652,122; Fawell, S. et al., *Proc. Natl. Acad. Sci. U.S.A.*, 1994, 91:664-668). Peptides such as the homeodomain of *Drosophila antennapedia* (ANTp) and arginine-rich peptides display similar properties (Derossi, D. et al., *J. Biol. Chem.*, 1994, 269:10444-10450; Derossi, D. et al., *Trends Cell Biol.*, 1998, 8:84-87; Rojas, M. et al., *Nat. Biotechnol.*, 1998, 16:370-375; Futaki, S. et al., *J. Biol. Chem.*, 2001, 276:5836-5840). VP22, a tegument protein from Herpes simplex virus type 1 (HISV-1), also has the ability to transport proteins across a cell membrane (Elliot et al., *Cell*, 1997, 88:223-233; Schwarze S. R. et al., *Trends Pharmacol. Sci.*, 2000, 21:45-48). A common feature of these carriers is that they are highly basic and hydrophilic (Schwarze S. R. et al., *Trends Cell Biol.*, 2000, 10:290-295). Coupling of these carriers to marker proteins such as beta-galactosidase has been shown to confer efficient internalization of the marker protein into cells. More recently, chimeric, in-frame fusion proteins containing these carriers have been used to deliver proteins to a wide spectrum of cell types both in vitro and in vivo. For example, VP22-p53 chimeric protein retained its ability to spread between cells and its pro-apoptotic activity, and had a widespread cytotoxic effect in p53 negative human osteosarcoma cells in vitro (Phelan, A. et al., *Nature Biotechnol.*, 1998, 16:440-443). Intraperitoneal injection of the beta-galactosidase protein fused to the HIV-1 Tat peptide resulted in delivery of the biologically active fusion protein to all tissues in mice, including the brain (Schwarze S. R. et al., *Science*, 1999, 285:1569-1572).

Liposomes of various compositions can also be used for site-specific delivery of proteins and drugs (Witschi, C. et al., *Pharm. Res.*, 1999, 16:382-390; Yell, M. K. et al., *Pharm. Res.*, 1996, 1693-1698). The interaction between the liposomes and the protein cargo usually relies on hydrophobic interactions or charge attractions, particularly in the case of caLionic lipid delivery systems (Zelphati, O. et al., *J. Biol. Chem.*, 2001, 276:35103-35110). Tat peptide-bearing liposomes have also been constructed and used to deliver cargo directly into the cytoplasm, bypassing the endocytotic pathway (Torchilin V. P. et al., *Biochim. Biophys. Acta-Biomembranes*, 2001, 1511:397-411; Torchilin V. P. et al., *Proc. Natl. Acad. Sci. USA*, 2001, 98:8786-8791). When encapsulated in sugar-grafted liposomes, pentamidine isethionate and a derivative have been found to be more potent in comparison to normal liposome-encapsulated drug or to the free drug (Banerjee, G. et al., *J. Antimicrob. Chemother.*, 1996, 38(1):145-150). A thermo-sensitive liposomal taxol formulation (heat-mediated targeted drug delivery) has been administered in vivo to tumor-bearing mice in combination with local hyperthermia, and a significant reduction in tumor volume and an increase in survival time was observed compared to the equivalent dose of free taxol with or without hyperthermia (Sharma, D. et al., *Melanoma Res.*, 1998, 8(3):240-244). Topical application of liposome preparations for delivery of insulin, IFN-alpha, IFN-gamma, and prostaglandin E1 have met with some success (Cevc G. et al., *Biochim. Biophys, Acta*, 1998, 1368:201-215; Foldvari M. et al., *J. Liposome Res.*, 1997, 7:115-126; Short S. M. et al., *Pharm. Res.*, 1996, 13:1020-1027; Foldvari M. et al., *Urology*, 1998, 52(5):838-843; U.S. Pat. No. 5,853,755).

Antibodies represent another targeting device that may make liposome uptake tissue-specific or cell-specific (Mastrobattista, E. et al., *Biochim. Biophys. Acta*, 1999, 1419(2): 353-363; Mastrobattista, E. et al., *Adv. Drug Deliv. Rev.*, 1999, 40(1-2):103-127). The liposome approach offers several advantages, including the ability to slowly release encapsulated drugs and proteins, the capability of evading the immune system and proteolytic enzymes, and the ability to target tumors and cause preferentially accumulation in tumor tissues and their metastases by extravasation through their leaky neovasculature. Other carriers have also been used to deliver anti-cancer drugs to neoplastic cells, such as polyvinylpyrrolidone nanoparticles and maleylated bovine serum albumin (Sharma, D. et al., *Oncol. Res.*, 1996, 8(7-8):281-286; Mukhopadhyay, A. et al., *FEBS Lett.*, 1995, 376(1-2): 95-98). Thus, using targeting and encapsulation technologies, which are very versatile and amenable to rational design and modification, delivery of NP to desired cells can be facilitated. Furthermore, because many liposome compositions are also viable delivery vehicles for genetic material, many of the advantages of liposomes are equally applicable to polynucleotides encoding NP.

As indicated above, the pharmaceutical composition of the present invention can include a liposome component. According to the present invention, a liposome comprises a lipid composition that is capable of fusing with the plasma membrane of a cell, thereby allowing the liposome to deliver a nucleic acid molecule and/or a protein composition into a cell. Some preferred liposomes include those liposomes commonly used in gene delivery methods known to those of skill in the art. Some preferred liposome delivery vehicles comprise multilamellar vesicle (MLV) lipids and extruded lipids, although the invention is not limited to such liposomes. Methods for preparation of MLVs are well known in the art. "Extruded lipids" are also contemplated. Extruded lipids are lipids that are prepared similarly to MLV lipids, but which are subsequently extruded through filters of decreasing size, as described in Templeton et al., *Nature Biotech.*, 1997, 15:647-652, which is incorporated herein by reference in its entirety. Small unilamellar vesicle (SUV) lipids can also be used in the compositions and methods of the present invention. Other preferred liposome delivery vehicles comprise liposomes having a polycationic lipid composition (i.e. cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes utilized in the present invention can be any size, including from about 10 to 1000 nanometers (nm), or any size in between.

A liposome delivery vehicle can be modified to target a particular site in a mammal, thereby targeting and making use of an NP-encoding nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry*, 1986, 25: 5500-6; Ho et al., *J Biol Chem*, 1987a, 262: 13979-84; Ho et al., *J Biol Chem*, 1987b, 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., *FEBS Lett*, 1987, 223: 42-6) or polyethylene glycol (PEG)-derived lipids (Klibanov et al., *FEBS Lett*, 1990, 268: 235-7), can be incorporated into the bilayer of a conventional liposome to form the so-called sterically-stabilized or "stealth" liposomes (Woodle et al., *Biochim Biophys Acta*, 1992, 1113: 171-99). Variations of such liposomes are described, for example, in U.S. Pat. No. 5,705, 187 to Unger et al, U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

The NP-encoding nucleic acid sequences of the present invention can be conjugated with chitosan. For example, DNA chitosan nanospheres can be generated, as described by Roy, K. et al. (1999, *Nat Wed* 5:387). Chitosan allows increased bioavailability of the NP-encoding nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue.

Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used interchangeably herein are intended to include such human and non-human mammalian species. According to the method of the present invention, human or non-human mammalian NP (or nucleic acid sequences encoding human or non-human mammalian NP) can be administered to the patient. The NP may be naturally occurring within the patient's species or a different mammalian species. The expression vectors used in the subject invention can comprise nucleic acid sequences encoding any human or non-human mammalian NP. In instances where genetically modified cells are administered to a patient, the cells may be autogenic, allogeneic, or xenogeneic, for example.

In another aspect, the present invention concerns pharmaceutical compositions containing a therapeutically effective amount of agent that reduces NPR-A activity, such as an NP, or polynucieotides encoding NP, and a pnarmaceutically acceptable carrier. Preferably, if the agent is a polynucleotide, such as an NP-encoding nucleic acid sequence, the polynucleotide is contained within an expression vector, such as plasmid DNA or a virus. Pharmaceutical compositions including a therapeutically effective amount of an agent that reduces NPR-A activity such as NP, or nucleic acid sequences encoding NP, and a pharmaceutically acceptable carrier, can be administered to a patient by any effective route, including local or systemic delivery. Administration can be continuous or at distinct intervals as can be determined by a person skilled in the art.

The agent that reduces NPR-A activity, such as NP or polynucleotides encoding NP (and pharmaceutical compositions containing them), can be administered to a patient by any route that results in prevention (or reduction of onset) or alleviation of symptoms associated with cancer, such as pain. For example, the agent (e.g., NP or NP-encoding nucleic acid molecule) can be administered parenterally, intravenously (I.V.), intramuscularly (I.M.), subcutaneously (S.C.), intradermally (I.D.), topically, transdermally, orally, intranasally, etc.

If desired, the pharmaceutical composition can be adapted for administration to the airways of the patient, e.g., nose, sinus, throat and lung, for example, as nose drops, as nasal drops, by nebulization as an inhalant, vaporization, or other methods known in the art. Examples of intranasal administration can be by means of a spray, drops, powder or gel and also described in U.S. Pat. No. 6,489,306, which is incorporated herein by reference in its entirety. One embodiment of the present invention is the administration of the invention as a nasal spray. Alternate embodiments include administration through any oral or mucosal routes, sublingual administration and even eye drops. However, other means of drug administrations are well within the scope of the present invention.

The pharmaceutical compositions of the subject invention can be formulated according to known methods for preparing pharmaceutically useful compositions. Furthermore, as used herein, the phrase "pharmaceutically acceptable carrier" includes any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, *Remington's Pharmaceutical Sciences* (Martin E. W., 1995, Easton Pa., Mack Publishing Company, 19$^{th}$ ed.), which is incorporated herein by reference in its entirety, describes formulations that can be used in connection with the subject invention.

Pharmaceutical compositions of the present invention useful for parenteral injection can include pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene, lycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Formulations suitable for parenteral administration include, for example, aqueous injectable solutions that may contain antioxidants, buffers, and solutes which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that, in addition to the ingredients particularly mentioned above, the formulations of the subject invention can include other agents conventional in the art having regard to the type of formulation in question.

The pharmaceutical compositions used in the methods of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption, such as aluminum monostearate and gelatin.

In some cases, in order to prolong the effect of the active agent (e.g., NP), it is desirable to slow the absorption from subcutaneous or intramuscular injection. This may be accomplished by the use of a liquid suspension of crystalline or amorphous material with poor water solubility. The rate of absorption of the NP or NP-encoding polynucleotide then depends upon its rate of dissolution which, in turn, may depend upon crystal size and crystalline form. Alternatively, delayed absorption of a parenterally administered NP or NP-encoding polynucleotide is accomplished by dissolving or suspending the NP in an oil vehicle.

Injestable depot forms are made by forming microencapsule matrices of the agent (e.g. NP or NP-encoding polynucleotide) in biodegradable polymers such as polylactide-polyglycolide. Depending upon the ratio of active agent (e.g., NP or NP-encoding polynucleotide) to polymer and the nature of the particular polymer employed, the rate of release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active agents (NP or NP-encoding polynucleotide) are mixed with it least one pharmaceutically acceptable excipient or carrier such as sodium nitrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. Optionally, the solid dosage forms contain opacifying agents, and can be of a composition that releases the NP or NP-encoding polynucleotide only, or preferentially, in a certain part of the intestinal tract, optionally, in a delayed manner. Examples of embedding compositions that can be used include polymeric substances and waxes.

The active agents (NP or NP-encoding polynucleotide) can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the NP or NP-encoding polynucleotide, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder, which may be pressurized or non-pressurized. In nonpressurized powder compositions, the active ingredients in finely divided form may be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

Alternatively, the pharmaceutical composition may be pressurized and contain a compressed gas, such as nitrogen or a liquefied gas propellant. The liquefied propellant medium or the entire composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

The compositions and methods of the invention can further incorporate permeation enhancers, such as those described in U.S. Patent Publication No. 2003/0147943 (Luo et al.), penetrating peptides capable of facilitating penetration of an NP, or an NP-encoding polynucleotide, across a biological barrier, such as those described in U.S. Patent Publication No. 2004/0146549 (Ben-Sasson et al.), enhancer compounds that enhance the absorption of a polypeptide in the respiratory tract, such as those described in U.S. Patent Publication No. 2004/0171550 (Backstrom et al.), and suspension vehicles, such as those described in U.S. Patent Publication No. 2004/0224903 (Berry et al.), each of which are incorporated herein by reference in their entirety.

The agent that reduces NPR-A activity (such as NP or NP-encoding polynucleotide) is administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art. For example, an effective amount of NP-encoding polynucleotide is that amount necessary to provide an effective amount of NP, when expressed in vivo or in vitro. The amount of the agent (e.g., NP or NP-encoding nucleic acid molecule) must be effective to achieve some improvement including, but not limited to, improved survival rate, more rapid recovery, total prevention of symptoms associated with an inflammatory or cell proliferation disorder, such as cancer, or improvement or elimination of symptoms associated with an inflammatory or cell proliferation disorder, such as cancer, and other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for local or systemic administration based on the size of a mammal and the route of administration.

In accordance with the invention, a mammal (such as a human) that is predisposed to or suffering from a physical disorder may be treated by administering to the mammal an effective amount of an agent that reduces NPR-A activity (such as NP or NP-encoding polynucleotide), in combination with a pharmaceutically acceptable carrier or excipient therefore (as described below). Physical disorders treatable with the compositions and methods of the present invention include any physical disorder that may be delayed, prevented cured or otherwise treated by administration of an agent that reduces NPR-A activity (such as NP or NP-encoding polynucleotide) in a mammal suffering from or predisposed to the physical disorder. Such physical disorders include, but are not limited to, a variety of carcinomas and other cancers, such as skin cancers (including melanomas and Kaposi's Sarcoma), oral cavity cancers, lung cancers, breast cancers, prostatic cancers, bladder cancers, liver cancers, pancreatic cancers, cervical cancers, ovarian cancers, head and neck cancers, colon cancers, germ cell cancers (including teratocarcinomas) and leukemias. Other physical disorders treatable by the methods of the present invention include inflammatory disorders such as rheumatoid arthritis, multiple sclerosis, systemic lupus erythematosis, pelvic inflammatory disease, and Crohn's disease. The methods of the invention may also be used to treat a mammal suffering from or predisposed to a fibrotic disorder, including pulmonary fibrosis, cystic fibrosis, endomyocardial fibrosis, hepatic fibrosis (particularly hepatic cirrhosis), myelofibrosis, scleroderma, and systemic sclerosis. Other physical disorders treatable by the methods of the invention include osteoporosis, atherosclerosis, and ocular disorders such as corneal ulceration and diabetic retinopathy. The methods of the present invention may also be used in the prevention of disease progression, such as in chemoprevention of the progression of a premalignant lesion to a malignant lesion, and to treat a mammal suffering from, or predisposed to, other physical disorders that respond to treatment with compositions that differentially modulate gene expression.

Cell proliferation disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Cancers of any organ can be treated, including cancers of, but are not limited to, e.g., colon, pancreas, breast, prostate, bone, liver, kidney, lung, testes, skin, pancreas, stomach, colorectal cancer, renal cell carcinoma, hepatocellular carcinoma, melanoma, etc.

Examples of breast cancer include, but are not limited to, invasive ductal carcinoma, invasive lobular carcinoma, ductal carcinoma in situ, and lobular carcinoma in situ. Examples of cancers of the respiratory tract include, but are not limited to, small-cell and non-small-cell lung carcinoma, as well as bronchial adenoma and pleuropulmonary blastoma. Examples of brain cancers include, but are not limited to, brain stem and hypothalamic glioma, cerebellar and cerebral astrocytoma, medulloblastoma, ependymoma, as well as neuroectodermal and pineal tumor. Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers. Tumors of the urinary tract include, but are not limited to, bladder, penile, kidney, renal pelvis, ureter, and urethral cancers. Eye cancers include, but are not limited to, intraocular melanoma and retinoblastoma. Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to, squamous cell carcinoma, Kaposi's sarcoma, malignant melanoma, Merkel cell skin cancer, and non-melanoma skin cancer. Head-and-neck cancers include, but are not limited to, laryngeal, hypopharyngeal, nasopharyngeal, and/or oropharyngeal cancers, and lip and oral cavity cancer. Lymphomas include, but are not limited to, AIDS-related lymphoma, non-Hodgkin's lymphoma, cutaneous T-cell lymphoma, Hodgkin's disease, and lymphoma of the central nervous system. Sarcomas include, but are not limited to, sarcoma of the soft tissue, osteosarcoma, malignant fibrous histiocytoma, lymphosarcoma, and rhabdomvosarcoma. Leukemias include, but are not limited to, acute myeloid leukemia, acute lymphoblastic leukemia, chronic lymphocytic leukemia, chronic myelogenous leukemia, and hairy cell leukemia. In addition to reducing the proliferation of tumor cells, agents that reduce NPR-A activity can also cause tumor regression, e.g., a decrease in the size of a tumor, or in the extent of cancer in the body.

In addition to chemotherapeutic agents, the methods and compositions of the subject invention can incorporate treatments and agents utilizing, for example, angiogenesis inhibitors (Thalidomide, Bevacizumab), Bcl-2 antisense oligonucleotides (G3139), a PSA based vaccine, a PDGF receptor inhibitor (Gleevec), microtubule stabilizers (Epothilones), and a pro-apoptotic agent (Perifosine). Thus, an NP or NP-encoding polynucleotide can be administered to a patient in combination (simultaneously or consecutively) with other agents for useful for treating inflammatory disorders and/or cell proliferation disorders. Likewise, the pharmaceutical compositions of the subject invention can include such agents.

The term "gene therapy", as used herein, refers to the transfer of genetic material (a polynucleotide, e.g., DNA or RNA) of interest into a host to treat or prevent a genetic or acquired disease or condition phenotype. The genetic material of interest encodes a product (e.g., a protein, polypeptide, peptide, or functional RNA) whose production in vivo is desired, such as NP. In addition to one or more NP, the genetic material of interest can encode a hormone, receptor, enzyme, polypeptide or peptide of therapeutic and/or diagnostic value. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy, cells are removed from a patient and, while being cultured, are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to produce the transfected gene product in situ.

In in vivo gene therapy, target cells are not removed from the subject, rather the gene to be transferred is introduced into the cells of the recipient organism in situ, that is within the recipient. Alternatively, if the host gene is defective, the gene is repaired in situ. Thus, these genetically altered cells produce the transfected gene product (e.g. NP) in situ.

The gene expression vector is capable of delivery/transfer of heterologous nucleic acid sequences (e.g. NP-encoding nucleic acid sequences) into a host cell. The expression vector may include elements to control targeting, expression and transcription of the nucleic acid sequence in a cell selective manner as is known in the art. It should be noted that often the 5'UTR and/or 3'UTR of the gene may be replaced by the 5'UTR and/or 3'UTR of the expression vehicle.

The expression vector can include a promoter for controlling transcription of the heterologous material and can be either a constitutive or inducible promoter to allow selective transcription. The expression vector can also include a selection gene.

Vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and include, for example, stable or transient transfection, lipofection, electroporation, and infection with recombinant viral vectors.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of a DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

In another aspect, the present invention concerns an isolated peptide comprising the amino acid sequence $NP_{73-102}$ (SEQ ID NO:5), or a biologically active fragment or homolog thereof. $NP_{73-102}$ is amino acids 73-102 of the 151-amino acid long human atrial natriuretic factor (ANF). In another aspect, the present invention concerns an isolated peptide comprising the amino acid sequence of SEQ ID NO:6, or a biologically active fragment or homolog thereof. SEQ ID NO:6 is a biologically active fragment of the human ANF. In another aspect, the present invention concerns an isolated nucleic acid molecule encoding the amino acid sequence of $NP_{73-102}$ (SEQ ID NO:5), or a biologically active fragment or homolog thereof. In another aspect, the present invention concerns an isolated nucleic acid molecule (SEQ ID NO:13) encoding the amino acid sequence of SEQ ID NO:6, or a biologically active fragment or homolog thereof.

As used herein, the terms "peptide", "polypeptide", and "protein" refer to amino acid sequences of any length unless otherwise specified.

Assays for Identifying Agents that Reduce Natriuretic Peptide Receptor-A Activity The present invention also includes methods for identifying agents that reduce the activity of natriuretic peptide receptor-A (also known in the art as NPRA, NPR-A, and guanylate cyclase A) in vitro or in vivo (also referred to herein as the diagnostic method or screening assay of the invention). Such agents are potentially useful for treating inflammatory or cell proliferation disorders in a patient. In the therapeutic methods and assays of the invention, agents that reduce NPR-A activity include those that, for example, reduce ANP-NPR-A induced c-GMP production, reduce expression of NPR-A, reduce cellular internalization of NPR-A, reduce recycling of NPR-A to the cell membrane, or otherwise interfere with the activity of the receptor.

Production of ANP-NPR-A induced cGMP production can be assayed and used as a high-throughput method for screening agents for anti-proliferative (e.g., anti-cancer) and anti-inflammatory activity. This assay can be carried out using a cell line that transiently or stably expresses the receptor for ANP, NPR-A (Pandey et al., *J Biol. Chem.* 2002, 277:4618-4627) and libraries of agents, such as peptide and compound libraries, which can be novel or obtained commercially. An assay for cGMP can be performed to select agents that are inhibitors of cGMP. Alternatively, ANP peptide can be linked with a moiety that can antagonize cGMP following internalization, which can be checked using a transiently or stably transfected cell line expressing NPR-A.

In the context of the screening assay of the invention, the terms "recombinant host cells", "host cells", "genetically modified host cells" "cells", "cell lines", "cell cultures", and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell that has been transfected. Cells in primary culture can also be used as recipients. Host cells can range in plasticity and proliferation potential. Host cells can be differentiated cells, progenitor cells, or stem cells, for example.

Host cells can be genetically modified with vectors to express (e.g., overexpress) the NPR-A receptor, or a mutant, isoform, or other variant thereof, which may be a cloning vector or an expression vector, for example. The vector may be in the form of a plasmid, a virus, (e.g. a retrovirus or other virus), a viral particle, a phage, etc. The genetically modified host cells can be cultured in conventional nutrient media modified as appropriate for activating promoters, selecting transformants/transfectants or amplifying the receptor-encoding polynucleotide.

In one embodiment, the host cell is a human cell. In another embodiment, the host cell is a non-human mammalian cell. Both prokaryotic and eukaryotic host cells may be used for expression of desired coding sequences when appropriate control sequences (e.g., promoter sequences) that are compatible with the designated host are used. For example, among prokaryotic hosts, *Escherichia coli* may be used. Also, for example, expression control sequences for prokaryotes include but are not limited to promoters, optionally containing operator portions, and ribosome binding sites. Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast compatible vectors may employ the 2-p origin of replication (Broach et al. *Meth. Enzymol.* 101:307, 1983), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. (See, for example, Hess et al. *J. Adv. Enzyme Reg.* 7:149, 1968; Holland et al. *Biochemistry* 17:4900, 1978; and Hitzeman *J. Biol. Chem.* 255:2073, 1980). For example, some useful control systems are those that comprise the glyceraldehyde-3-phosphate dehydrogenase (GAPDH) promoter or alcohol dehydrogenase (ADH) regulatable promoter, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Host cells useful for expression of polynucleotides encoding the NPR-A receptor may be primary cells or cells of cell lines. The host cells may be tumor cells (transformed cells) or non-tumor cells. Mammalian cell lines available as hosts for expression are known in the art and are available from depositories such as the American Type Culture Collection. These include but are not limited to Hela cells, human embryonic kidney (HEK) cells, Chinese hamster ovary (CHO) cells, baby hamster kidney (BHK) cells, and others.

The number of host cells used in a particular assay will vary with the objectives of the assay, the solid support used to support or contain the cell(s), if one is utilized etc. Thus, in some protocols, the host cell may be a single cell. In other protocols, a plurality of host cells will be used.

In accordance with the screening assay of the invention, the polynucleotide encoding the NPR-A is operably linked to a promoter sequence. Suitable promoters sequences for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences including the NPR-A receptor into the host genome. An example of such a mammalian expression system is described in Gopalakrishnan et al. *Eur. J. Pharmacol.-Mol. Pharmacol.* 290: 237-246, 1995).

Candidate agents (and treatments) that may be tested by the screening assays of the present invention include polypeptides, non-peptide small molecules, biological agents, and any other source of candidate agents potentially having the ability to modulate (e.g., reduce) NPR-A activity. Candidate agents and treatments may be useful for the treatment of inflammatory and/or cell proliferation disorders, such as cancer. Candidate agents can be virtually any substance and can encompass numerous chemical classes, including organic compounds or inorganic compounds. A candidate agent may be a substance such as genetic material, protein, lipid, carbohydrate, small molecules, a combination of any of two or more of foregoing, or other compositions. Candidate agents may be naturally occurring or synthetic, and may be a single substance or a mixture. Candidate agents can be obtained from a wide variety of sources including libraries of compounds. A candidate agent can be or include, for example, a polypeptide, peptidomimetic, amino acid(s), amino acid analog(s), polynucleotide(s), polynucleotide analog(s), nucleotide(s), nucleotide analog(s), or other small molecule(s). A polynucleotide may encode a polypeptide that potentially reduces NPR-A activity within the cell, or the polynucleotide may be a short interfering RNA (siRNA), a hairpin RNA (shRNA), antisense oligonucleotide, ribozyme, or other polynucleotide that targets an endogenous or exogenous gene for silencing of gene expression and potentially NPR-A activity within the cell. Candidate treatments may include exposure of the host cells to any conditions that potentially reduce NPR-A activity within the host cells. The treatment may involve exposing the cells to an energy source, for example.

According to the screening assay of the invention, the method for identifying agents (which is intended to be inclusive of treatments) that reduce NPR-A activity is used to identify an agent that is therapeutic for treating an inflammation disorder and/or cell proliferation disorder, such as cancer. In aspect, the screening assay comprising contacting a host cell with a candidate agent, wherein the host cell expresses NPR-A, or an active fragment or variant thereof, and determining whether activity of the receptor is reduced, wherein a decrease in receptor activity is indicative of a potentially therapeutic agent. The method can optionally include an additional step of comparing NPR-A activity in the presence of the candidate agent, with NPR-A activity in the absence of the candidate agent (e.g., or other positive or negative control). The determination of NPR-A activity may be quantitative, semi-quantitative, or qualitative.

Known methods for overexpressing NPR-A in host cells and determining intracellular cGMP may be utilized to determine whether NPR-A activity is reduced (Kumar et al., Hypertension, 1997, 29(part 2):414-421; Khurana M. L. and Pandey K. N., *Endocrinology*, 1993, 133:2141-2149; Delport C. et al., *Eur. J. Pharmacol.*, 1992, 224(2-3):183-188; Ohyama Y. et al., *Biochem. Biophys. Res. Commun.*, 1992, 189(1):336-342; Sharma G. D. et al., Expression of Atrial Natriuretic Peptide Receptor-A Antagonizes the Mitogen-Activated Protein Kinases (erk2 and P38$^{MAPK}$) in cultured human vascular Smooth Muscle Cells", in Molecular and Cellular Biochemistry, Springer Science+Business Media B. V., ISSN:0300-8177, Vol. 233, Number. 1-2, April 2002, pages 165-173; Pandey K. N. et al., *Biochem. Biophys. Res. Commun.*, 2000, 271(2):374-379; Fujiseki Y. et al., *Jpn. J. Pharmacol.*, 1999, 79(3):359-368; Pandey K. N., *Can. J. Physiol. Pharmacol.*, 2001, 79(8):631-639; Pandey K. N., *Mol. Cell. Biochem.*, 2002, 230(1-2):61-72; Sekiguchi T. et al., *Gene*, 2001, 273:251-257; Chen S. et al., *J. Am. Soc. Nephrol.*, 2005, 16:329-339; Pandey K. N. et al., *J. Biol. Chem.*, 2002, 277(7):4618-4627; Pandey K. N. et al., *Biochem. J*, 2004, Dec. 1, Epub ahead of print; Roueau N. et al., Poster #P10144, "Development of a Non-radioactive Homogenous HTS Platform to Measure the Activity of Guanylate Cyclase", Presented at 10$^{th}$ Annual SBS Conference and Exhibition, Orlando, Fla., Sep. 11-15, 1004, PERKINELMER BIOSIGNAL Inc., Canada) each of which is incorporated herein by reference in its entirety). Functional truncations of NPR-A may also be used in the method of the invention (Pandey K. N. et al., *Molecular Pharmacology*, 2000, 57:259-267, which is incorporated herein by reference in its entirety). For example, using the AlphaScreen, a very sensitive assay platform capable of detecting fmol levels of non-acetylated cGMP has been developed (Rouleau et al., 2004). A biotinylated derivative of cGMP can be used as a tracer in a competitive immunoassay format involving rabbit anti cGMP antibodies. The AlphaScreen signal is generated when streptavidin coated Donor beads and protein A coated Acceptor beads are brought into proximity by the formation of the biotin-cGMP/anti-cGMP IgG complex. Production of cGMP by either particulate or soluble forms of guanylate cyclase leads to a decrease of the AlphaScreen signal by inhibiting the formation of the biotin-cGMP/anti-cGMP IgG complex. Using this assay, the activity of the atrial natriuretic peptide receptor (NPR-A, particulate guanylate cyclase) overexpressed in CHO cells has been characterized as well as that of soluble guanylate cyclase. Pharmacological parameters and Z' values obtained indicate that the assay platform is amenable to HTS.

In addition to determining whether an agent reduces NPR-A activity in vitro (e.g., in a cellular or acellular assay) and/or in vivo (in a human or non-human patient, or an animal model), the method may further comprise determining whether the agent reduces the physiological effects or symptoms associated with an inflammatory disorder and/or cell proliferation disorder, such as cancer, in vitro and/or in vivo (e.g., in an animal model). For example, the method may further comprise determining whether the agent has an apoptotic effect on cancer cells in vitro. These steps may be carried out before, during, or after NPR-A activity is assayed.

Contacting steps in the assays (methods) of the invention can involve combining or mixing the candidate agent and the cell in a suitable receptacle, such as a reaction vessel, microvessel, tube, microtube, well, or other solid support. Host cells and/or candidate agents may be arrayed on a solid support, such as a multi-well plate. "Arraying" refers to the act of organizing or arranging members of a library, or other collection, into a logical or physical array. Thus, an "array" refers to a physical or logical arrangement of, e.g., library members (candidate agent libraries). A physical array can be any "spatial format" or physically gridded format" in which physical manifestations of corresponding library members are arranged in an ordered manner, lending itself to combinatorial screening. For example, samples corresponding to individual or pooled members of a candidate agent library can be arranged in a series of numbered rows and columns, e.g., on a multiwell plate. Similarly, host cells can be plated or otherwise deposited in microtitered, e.g., 96-well, 384-well, or -1536 well, plates (or trays). Optionally, host cells may be immobilized on the solid support.

A "solid support" (also referred to herein as a "solid substrate") has a fixed organizational support matrix that preferably functions as an organization matrix, such as a microtiter tray. Solid support materials include, but are not limited to, glass, polacryloylmorpholide, silica, controlled pore glass (CPG), polystyrene, polystyrene/latex, polyethylene, polyamide, carboxyl modified teflon, nylon and nitrocellulose and metals and alloys such as gold, platinum and palladium. The solid support can be biological, non-biological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art. The surface of the solid substrate may contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface can be composed of any of a wide variety of materials, for example, polymers, plastics, resins, polysaccharides-silica or silica-based materials, carbon, metals, inorganic glasses, membranes, or any of the above-listed substrate materials.

Measurement of NPR-A gene expression can be carried out using RT-PCR, for example. Screening of candidate agents or treatments (e.g., determination of NPR-A receptor activity) can be performed in a high-throughput format using combinatorial libraries, expression libraries, and the like. Other assays can be carried out on the host cells before, during, and/or after detection of NPR-A activity, and any or all assays may be carried out in an automated fashion, in a high-throughput format.

Alternatively, the aforementioned methods can be modified through the use of a cell-free assay. For example, instead of determining whether NPR-A activity in host cells is reduced by a candidate agent, extracts from host cells may be utilized and a fluorochrome or other detectable moiety can be associated with a nanoparticle or bead.

Once an agent has been determined to be one which reduces NPR-A activity, the agent can be combined with a pharmaceutically acceptable carrier. The method may further include a step of manufacturing the agent. The method may further include the step of packaging the agent.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined before, during, or after contacting an NPR-A receptor with a candidate agent, as described herein. For example, a transcription rate, mRNA level, translation rate, protein level, biological activity, cellular characteristic or property, genotype, phenotype, etc. can be determined prior to introducing a a candidate into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Measuring expression includes determining or detecting the amount of the polypeptide present in a cell or shed by it, as well as measuring the underlying mRNA, where the quantity of mRNA present is considered to reflect the quantity of polypeptide manufactured by the cell. Furthermore, the gene for the NPR-A can be analyzed to determine whether there is a gene defect responsible for aberrant expression or polypeptide activity.

Polypeptide detection can be carried out by any available method, e.g., by Western blots, ELISA, dot blot, immunoprecipitation, RIA, immunohistochemistry, etc. For instance, a tissue section can be prepared and labeled with a specific antibody (indirect or direct and visualized with a microscope. Amount of a polypeptide can be quantitated without visualization, e.g., by preparing a lysate of a sample of interest, and then determining by ELISA or Western the amount of polypeptide per quantity of tissue. Antibodies and other specific binding agents can be used. There is no limitation on how detection of NPR-A activity is performed.

Assays can be utilized which permit quantification and/or presence/absence detection of a target nucleic acid (e.g., NPR-A) in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g. Saiki et al., *Science* 1988, 241, 53; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99-115, 1997), ligase chain reaction ("LCR") (EP 320 308), one-sided PCR (Ohara et al., *Proc. Natl. Acad. Sci.* 1989, 86, 5673-5677), indexing methods (e.g., U.S. Pat. No. 5,508, 169), in situ hybridization, differential display (e.g., Liang et al., *Nucl. Acid. Res.* 1993, 21, 3269 3275; U.S. Pat. Nos. 5,262,311, 5,599,672 and 5,965,409; WO97/18454; Prashar and Weissman, *Proc. Natl. Acad. Sci.,* 93:659-663, and U.S. Pat. Nos. 6,010,850 and 5,712,126; Welsh et al., *Nucleic Acid Res.,* 20:4965-4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/0880), Strand Displacement Amplification ("SDA"), Repair Chain Reaction ("RCR"), nuclease protection assays, subtraction-based methods, Rapid-Scan, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., *Proc. Natl. Acad, Sci.* 1991, 88, 7276-7280; U.S. Pat. Nos. 5,210,015 and 5,994,063), real-time fluorescence-based monitoring (e.g., U.S. Pat. No. 5,928, 907), molecular energy transfer labels (e.g., U.S. Pat. Nos. 5,348,853, 5,532,129, 5,565,322, 6,030,787, and 6,177,635; Tyagi and Kramer, Nature Biotech., 14:303-309, 1996). Any method suitable for single cell analysis of gene or protein expression can be used., including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 1990, 2, 17-25; Eberwine et al., *Proc. Natl. Acad. Sci.* 1992, 89, 3010-3014; U.S. Pat. No. 5,723,290). These and other methods can be carried out conventionally, e.g. as described in the mentioned publications.

The terms "transfection", "transformation", and "introduction", and grammatical variations thereof, are used interchangeably herein to refer to the insertion of an exogenous polynucleotide (e.g., a nucleic acid sequence encoding an NP, or fragment, homolog, or variant thereof, or a nucleic acid sequence encoding an NPR-A, or fragment, homolog, or variant thereof, into a host cell, irrespective of the method used for the insertion, the molecular form of the polynucleotide that is inserted, or the nature of the cell (e.g., prokaryotic or eukaryotic). The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome. Thus, host cells of the invention include those that have been transfected with polyniucleotides encoding an NP, or fragment, variant, or homolog thereof, and those that have been transfected with polynucleotides encoding an NPR-A, or fragment, variant, or homolog thereof.

The phrases "isolated" or "biologically pure" refer to material that is substantially or essentially free from components which normally accompany the material as it is found in its native state.

An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

The terms "cell" and "cells" are used interchangeably herein to refer to a single cell or plurality of cells (i.e., at least one cell). Typically, host cells used in the methods of the invention are isolated. However, tissues, and genetically modified or transgenic animals may also be utilized.

The terms "comprising", "consisting of" and "consisting essentially of" are defined according to their standard meaning. The terms may be substituted for one another throughout the instant application in order to attach the specific meaning associated with each term.

As used in this specification, the singular forms "a", "an", and "the" include plural reference unless the context clearly dictates otherwise. Thus, for example, a reference to "a cell" includes more than one such cell. Reference to "a receptor" includes more than one such receptor. Reference to "a polynucleotide" includes more than one such polynucletodie. Reference to "a polypeptide" or "agent" includes more than one such polypeptide or agent, and the like.

The practice of the present invention can employ, unless otherwise indicated, conventional techniques of molecular biology, microbiology, recombinant DNA technology, electrophysiology, and pharmacology, that are within the skill of the art. Such techniques are explained fully in the literature (see, e.g. Sambrook. Fritsch & Maniatis. Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. eds. (1991) IRL Press)).

Example 1 pNP 73-102 Inhibits NPRA Expression

The structures of ANP and ANP like molecules with their ring-structure and receptors associated with it are well characterized. However, the N-terminal peptides do not have this structure. Neither KP nor NP73-102 was shown to bind ANP receptor NPRA (Mohapatra et al., *J Allergy Clin Immunol*, 2004, 114:520-526). The receptors for NP-73-102 are not known.

The highest expression of the ANP and ANP receptors is found in neonatal thymus. To test whether the peptide NP73-102 inhibits in vivo the ANP cascade, pregnant (12 days) mice were injected i.p. with pVAX (vector), or pNP73-102. After 1 day, mice were sacrificed and thymi removed from embryo, were homogenized. Cells were centrifuged and erythrocytes lysed by treating the suspension with ACK buffer. Cells were incubated with anti-NPRA or anti-NPRC antibodies for 1 hour, washed and incubated with PE-conjugated 2o Ab. Levels of NPR's were determined by flow cytometry. The results are shown in FIG. 1. The results demonstrate that pNP73-102 inhibited expression of NPRA in thymocytes. Although the mechanism is not clear, this may be due to feedback inhibition at the level intracellular signaling occurring via NPRA.

Example 2

NPRA Deficiency Decreases Pulmonary Inflammation

Development and chronicity of cancers has been attributed to the chronic inflammation in the affected organs. ANP was reported to have anti-inflammatory activity, although signaling through NPRA is known to cause a number of different biological activity including cell proliferation, immune activation, inflammation and apoptosis. To determine the role of NPRA signaling in the lung inflammation, groups (n=3) of wild type DBA/2 (wt) and NPR-C (ko) deficient mice and wild type C57/BL6 (wt) and NPR-A (ko) were sensitized with ovalbumin (20 mg/mouse) and after 2 weeks challenged i.n. with ovalbumin (20 mg/mouse). One day later, mice were sacrificed and lung sections were stained with H & E to examine inflammation. As shown in FIGS. 2A-2D, there was no significant difference in pulmonary inflammation between the wild-type and NPRC deficient mice. In sharp contrast, a comparison between wild-type C57BL6 and NPRA deficient mice showed that NPRA deficient mice had substantially reduced inflammation compared to wild type. These results indicate that ANP-NPRA signaling is involved in increasing inflammation in the lung.

Example 3

Figure 3A:
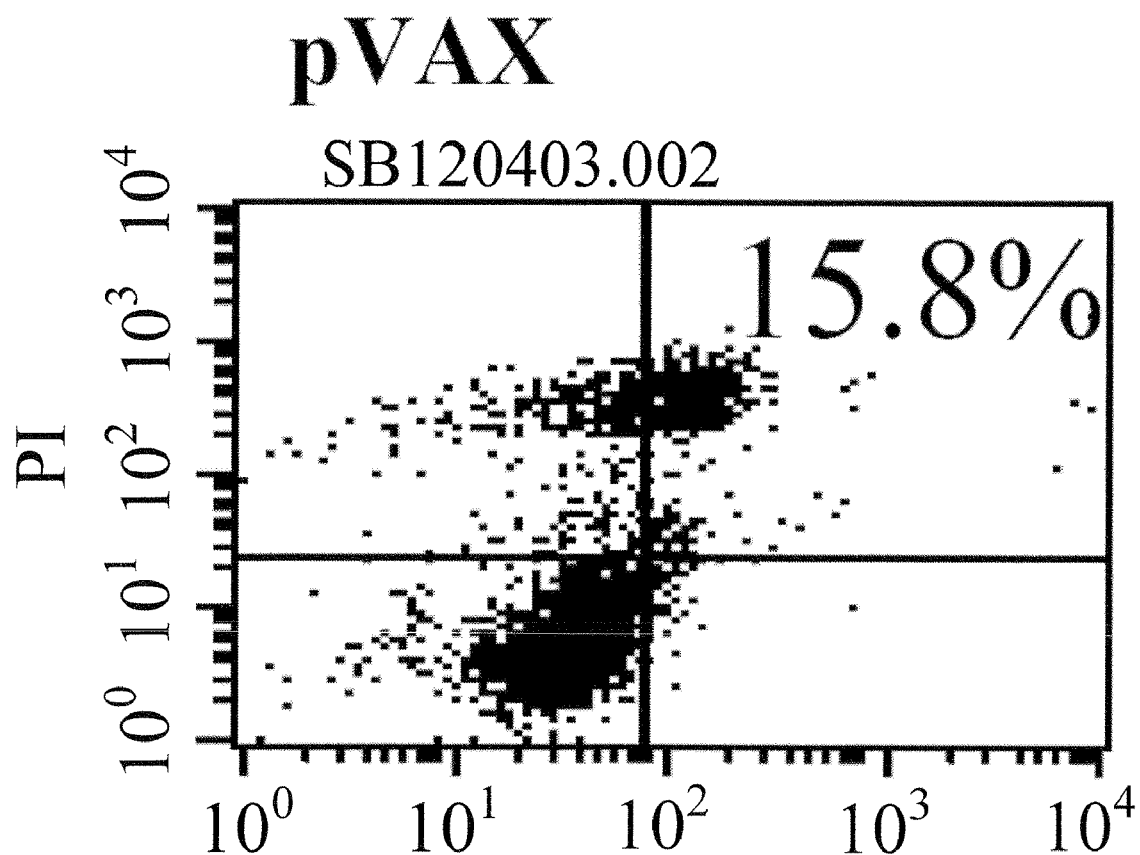
FIGS. 3A-3D demonstrate that A549 cells transfected with $pNP_{73-102}$ show a significantly higher level of apoptosis compared to control and pANP or pVAX (FIGS. 3A-3C). Cells were transfected with pNP73-102, pANP and pVAX (as control) and cells were stained with PI and annexin and quantified by flow cytometry (FIG. 3D). The proteins were isolated and an equal amount of the cell lysates were western-blotted using an antibody to poly-ADP ribose polymerase (PARP). The results demonstrate that pNP73-102 shows a higher accumulation of apoptotic cells compared to cells transfected with pANP and pVAX controls.
Figure 3B:
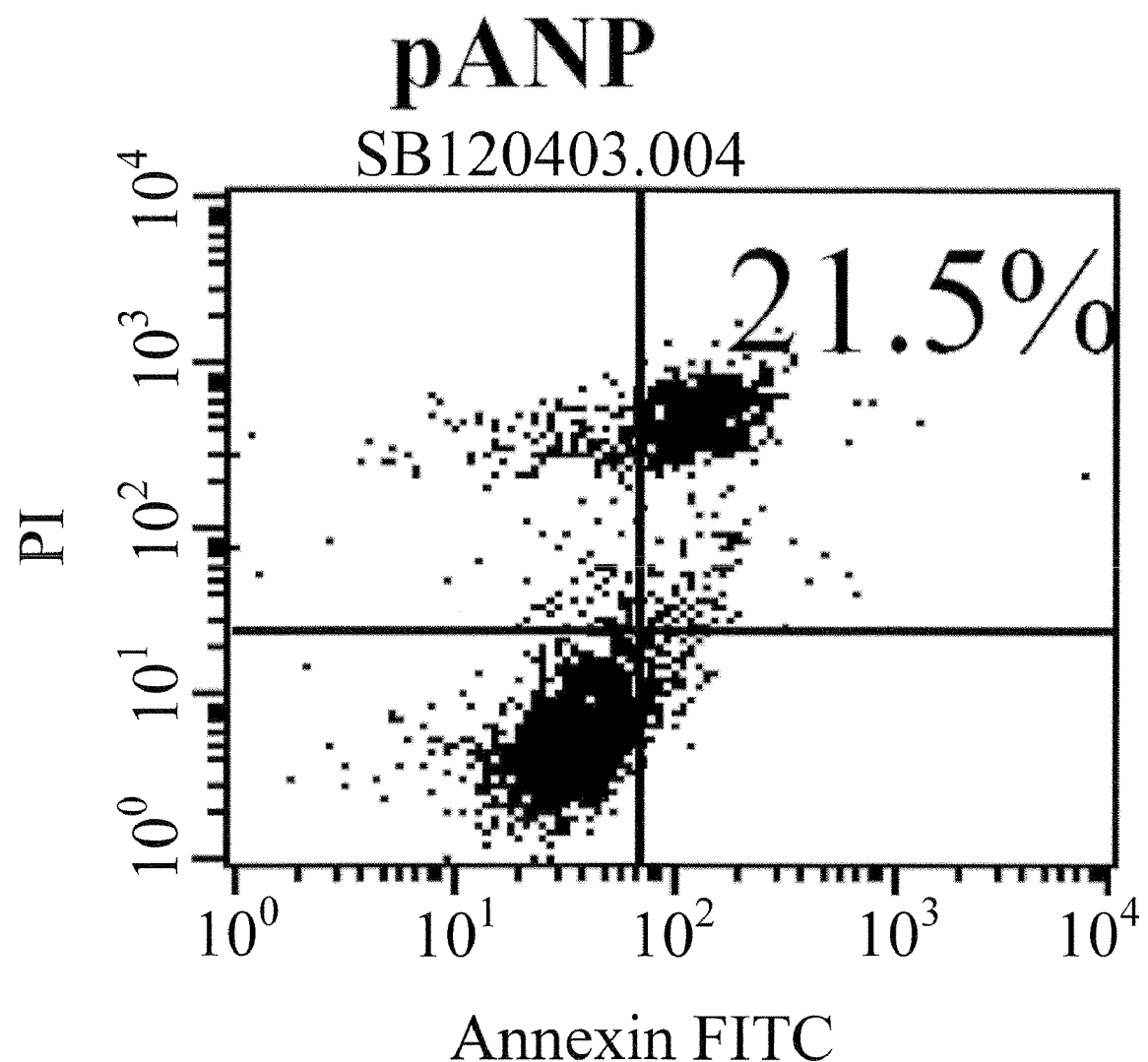
Figure 3C:
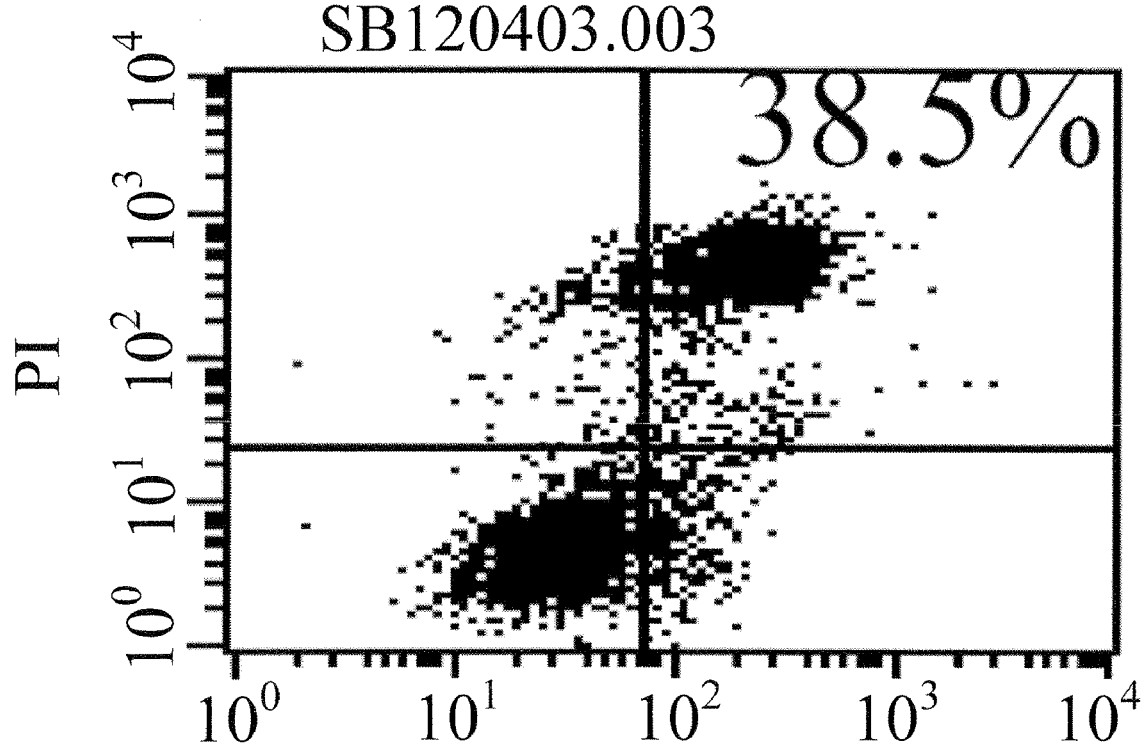
Figure 3D:
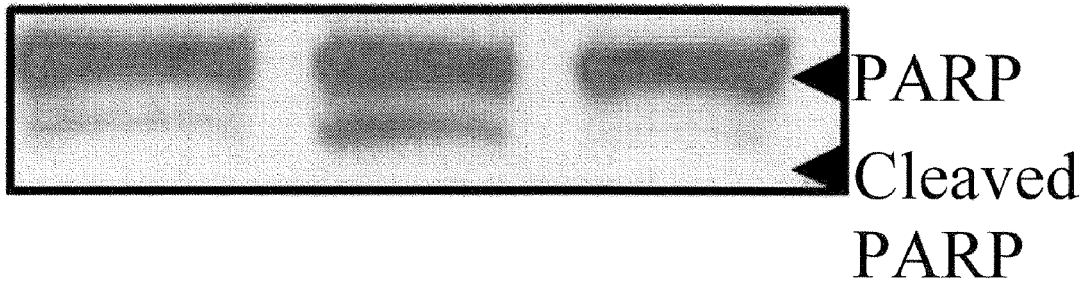
Figure 4:
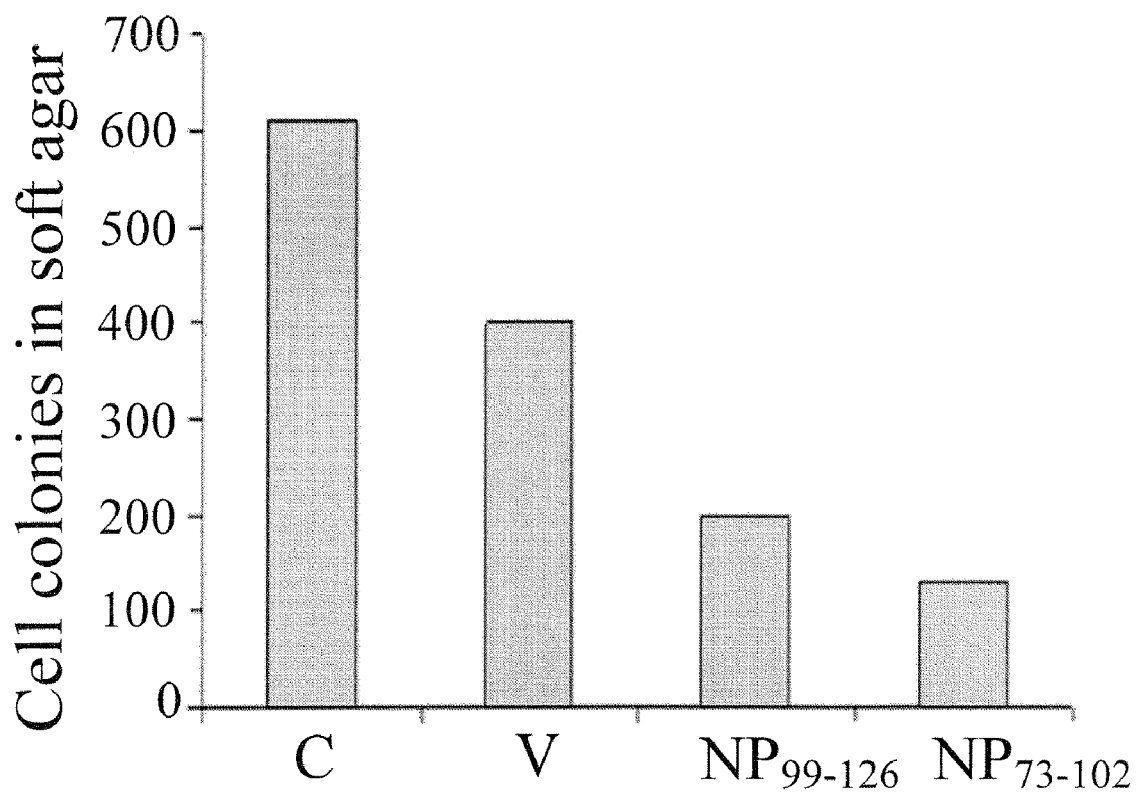
FIG. 4 shows that pNP73-102 decreases tumorigenesis in a colony formation assay by A549. Six centimeter tissue culture plates were covered with 4 ml of 0.5% soft agar. A549 cells were transfected with pANP, pNP73-102 and pVAX plasmid DNA (V) or nothing (C). After 40 h of transfection, cells were suspended in 2 ml of 0.3% soft agar and added to each plate. Cells were plated in duplicate at a density of $2 \times 10^4$ cells/dish and incubated for two weeks. Plates were photographed under a microscope. Cell colonies were counted and plotted. The results of one representative experiment of two is shown.
Figure 5A:
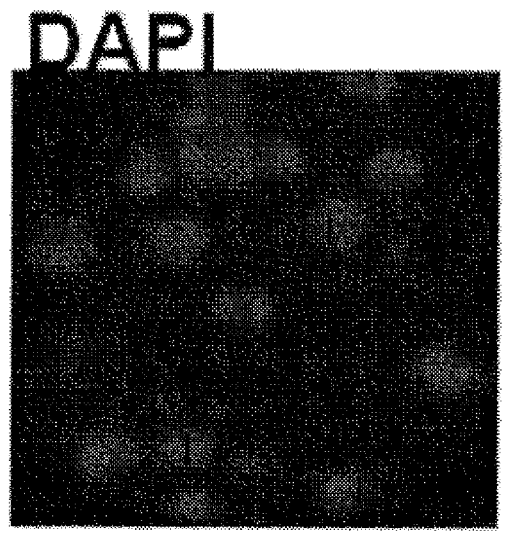
FIGS. 5A-5E show expression of $NP_{73-102}$-FLAG in the BAL cells after i.n. administration of chitosan encapsulated plasmid $pNP_{73-102}$-FLAG construct. BAL was performed in mice (n=3) after 24 hours and BAL cells were stained with either the second antibody control or anti-FLAG antibody (SIGMA) and then with DAPI. A representative staining is shown (FIGS. 5A-5C).
Figure 5B:
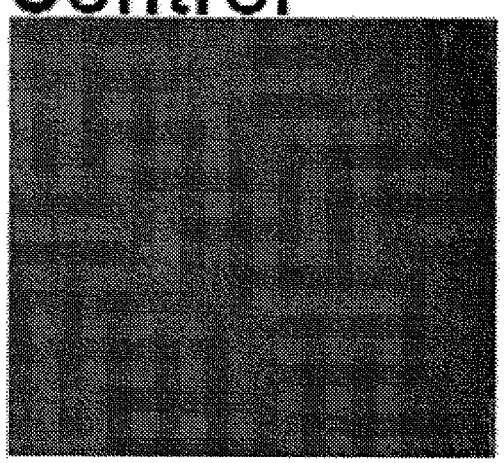
Figure 5C:
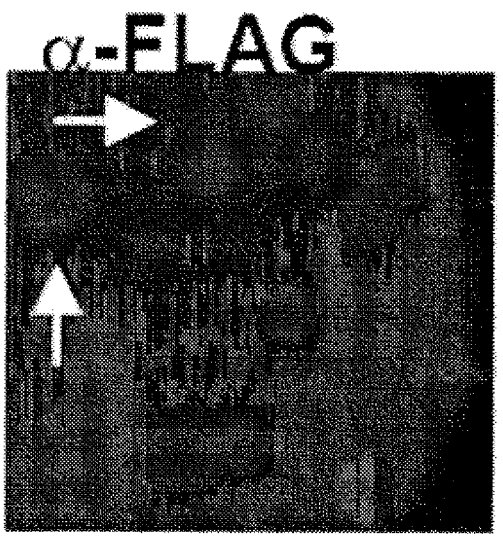
Figure 5D:
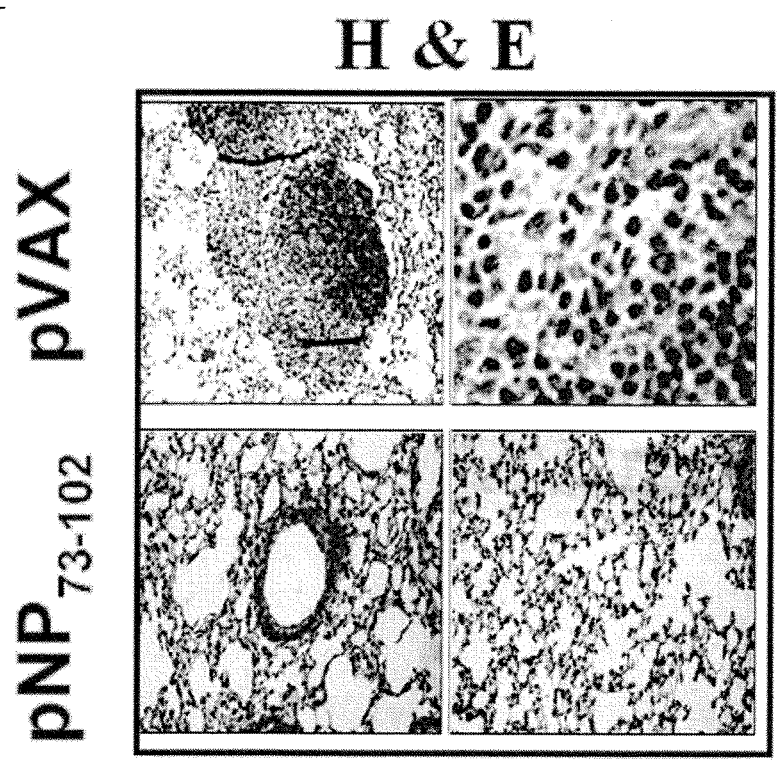
Figure 5E:
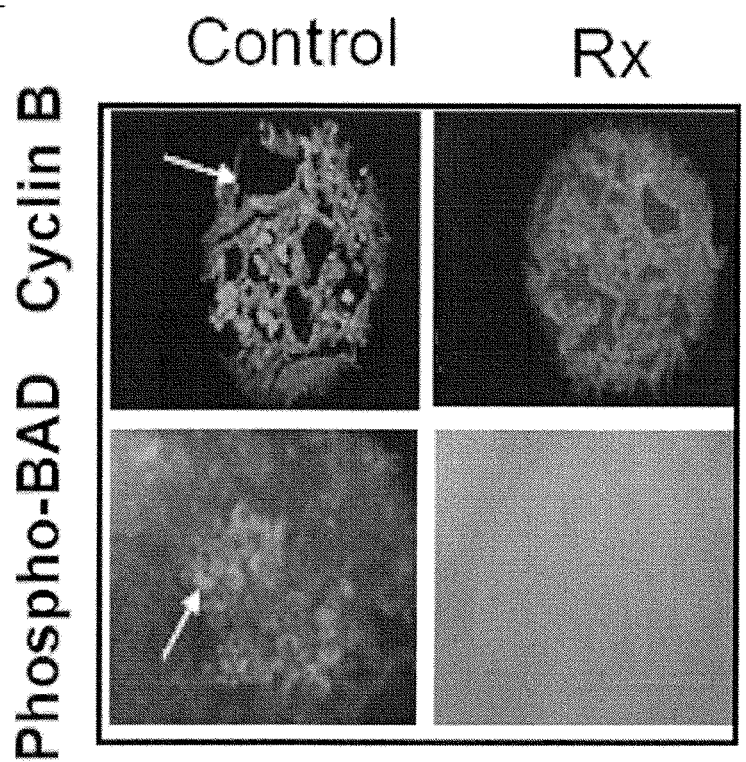

A549 Cells Transfected with $pNP_{73\text{-}102}$ Show a Significantly Higher Level of Apoptosis Compared Control and pANP or pVAX To determine the effect of overexpression of NP73-102 on proliferation of A549 lung epithelial cells, cells were transfected with either pNP73-102 or vector, pVAX. Cell cycle analysis was performed using propidium iodide (PI) staining and flow cytometry 48 h after transfection. No significant difference was observed between control and pNP73-102-transfected cells in S1, Go-G1 and G2-M stages of cell cycle (data not shown). However, an analysis of apoptosis using flow-cytometry with PI and annexin V, showed that cells transfected with pNP73-102 exhibited significantly higher apoptosis compared to cells transfected with either the control plasmid or a plasmid encoding ANP (FIGS. 3A-3C). This result was confirmed by (i) staining by TUNEL of A549 cells cultured in 8-chamber slide following a 48-hour transfection with either pANP or pNP73-102 (not shown), (ii) by analysis of PARP cleavage in these cells 48 hours after transfection, which was significantly more prominent in pNP73-102 transfected cells (FIG. 3D). The results show that pNP73-102 shows a higher accumulation of apoptotic cells compared to cells transfected with pANP and pVAX controls. Thus, pNP73-102 induces apoptosis of lung adenocarcinoma cells.

In an effort to identify and characterize molecules participating in early signaling pathways, differential gene expression was analyzed using a microarray (AFFYMETRIX). Altered expression of a large number of genes was found, including genes related to cell growth, cell cycle, and apoptosis. These genes included, among others more than, 6- to 8-fold up-regulation of genes such as Caspase (Casp)-8 and FADD like apoptosis regulator, cyclin E binding protein, CDK inhibitor 1A, CDK7, casp4, casp-10, casp-1, apoptosis facilitator BCL2-like 13 and annexin 43 (data not shown). Together, these studies indicate that pNP73-102 is an inducer of apoptosis in A549 lung adenocarcinoma cells.

Example 4 pNP73-102 Decreases Tumorigenesis in a Colony Formation Assay by A549

To test the anti-cancer activity of the pNP73-102 construct, a colony forming assay was undertaken. Thus, six cm tissue culture plates were covered with 4 ml of 0.5% soft agar. A549 cells were transfected with pANP, $pNP_{73-102}$ and pVAX plasmid DNA. After 40 hours of transfection, equal number of cells were suspended in 2 ml of 0.3% soft agar and added to each plate. Cells were plated in duplicate at a density of $2 \times 10^4$ cells/dish and incubated for two weeks. Plates were observed and photographed under a microscope. Cell colonies were counted and plotted. The results of one representative experiment of two experiments performed is shown in FIGS. 5A-5D. The results show that plasmid vector alone caused some reduction in colony formation compared to untransfected control. However, both ANP and $pNP_{73-102}$ showed substantial reductions in the number of colonies produced compared to vehicle control.

Example 5

Chitosan Nanoparticle Containing $pNP_{73-102}$ Substantially Decrease Tumor Development in the Lung To test the effect of de novo expression of $pNP_{73-102}$, the plasmid was coacervated with chitosan nanoparticles, referred to as CPNP73-102. To examine expression of NP73-102 from CPNP73-102, a construct was developed that carried a C-terminal fusion of marker peptide of FLAG. BALB/c mice were given intranasally the NP73-102-FLAG and the expression of NP73-102-FLAG in the BAL cells after i.n. administration of CPNP73-102-FLAG peptide. A bronchial lavage was performed after 24 hours and lavage cells were stained with either the second antibody control or anti-FLAG antibody (Sigma) and then with DAPI. The results show that intranasal administration induces significant expression of the peptide in the lung cells.

To test whether CPNP73-102 is capable of decreasing tumor formation in the lung, BALB/c nude mice were injected i.v. with $5 \times 10^6$ A549 cells, then treated one day afterwards and at weekly intervals with CPNP73-102 or control plasmid. After 4 weeks, mice were examined for lung histology. The control animals showed tumors, whereas no tumors were observed in the CpNP73-102-treated group. Sections were also stained with antibodies to cyclinB and to phospho-Bad. The results show that mice treated with CPNP73-102 had no tumors in the lung and did not show any staining for pro-mitotic Cyclin-B and anti-apoptotic marker phospho-Bad. These results indicate that CPNP73-102 has the potential to decrease tumor formation in the lung.

Example 6

Treatment with CPNP73-102 Decreases the Tumor Burden in a Spontaneous Tumorigenesis Model of Immunocompetent BALB/c Mice The nude mouse model is deemed to be of less predictive value in terms of translating to human cancer, as mice used are immunodeficient. Therefore, to confirm the results obtained on the potential role of pNP73-102, a syngeneic immunocompetent mouse model of human lung carcinoma was used. For this purpose, Line-1 cell line derived from a bronchio-alveeolar cell carcinoma (a subtype of lung adenocarcinoma that spontaneously arose in BALB/C mouse (Yuhas et al., *Cancer Research*, 1975, 35:242-244). The cell line forms subcutaneous tumors within 2 to 3 weeks of injection and spontaneously metastasizes to the lung.

Figure 6A:
FIGS. 6A-6D demonstrate that treatment with chitosan nanoparticles carrying $pNP_{73-102}$ (CPNP73-102) decreases the tumor burden in a spontaneous tumorigenesis model of immunocompetent BALB/c mice. Two groups of mice (n=4) were administered with the Line-1 tumor cells (100,000 cells/mouse) at the flanks. One group was administered with CPNP73-102 the same day, whereas another group was administered with vehicle alone (nanoparticle carrying a plasmid without NP73-102) and the third group was given the saline. Treatment was continued with CPNP73-102 or control at weekly intervals for 5 weeks. The tumors were dissected out from the mice of each group (FIGS. 6A-6C) and the tumor burden was calculated by weighing them on a balance and expressed as tumor mass per g lung weight. Results are shown in FIG. 6D.
Figure 6B:
Figure 6C:
Figure 6D:
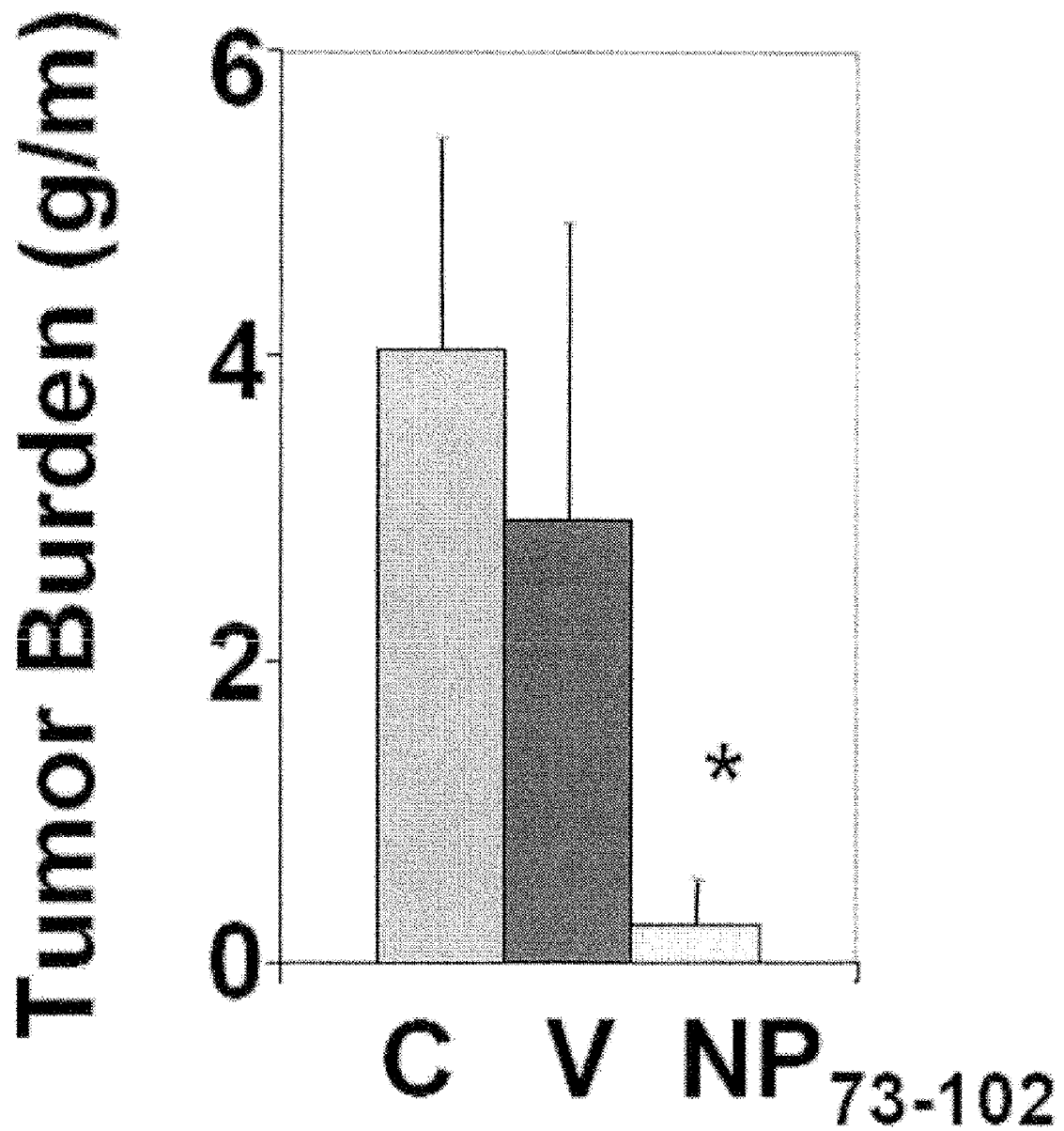

To examine whether de novo synthesis of NP73-102 affects tumor development, two groups of BALB/c mice (n=4) were administered with the Line-1 tumor cells (100,000 cells/mouse) at the flanks. One group was administered intranasally with CPNP73-102 the same day, whereas another group was administered with vehicle alone (nanoparticle carrying a plasmid without NP73-102), and the third group was given the saline. Treatment was continued with NP73-102 or controls at weekly intervals for 5 weeks. The tumors were dissected out from each group of mice and photographed (FIGS. 6A-6C) and the tumor burden was calculated by weighing them on a balance (FIG. 6D). The results show that mice administered with CPNP73-102 had significantly decreased tumor burden ($P<0.05$).

Example 7 pPNP73-102 Induces Apoptosis in Chemoresistant Ovarian Cancer Cells

Figure 7:
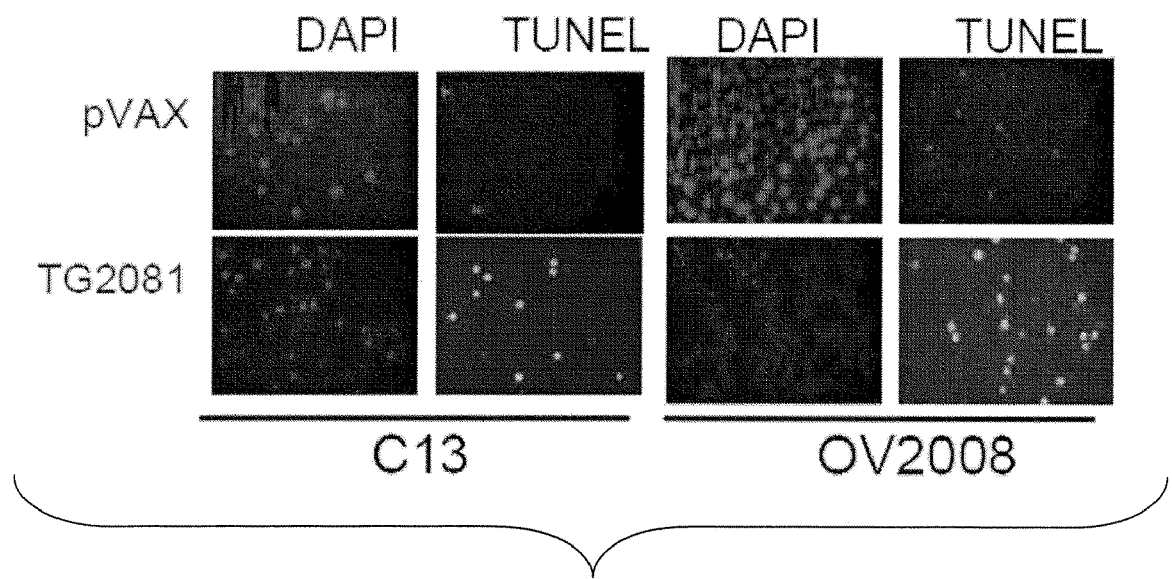
FIG. 7 shows that CPNP73-102 induces apoptosis in chemoresistant ovarian cancer cells. C-13 and OV2008 ovarian cancer cells were transfected with pNP73-102. Forty-eight hours later, cells were processed for TUNEL assay to examine apoptosis. The results of one of two representative experiments are shown.

The adenocarcinomas of various tissues such as lung, ovary., and breasts have many characteristics that are similar. Chemoresistance is a major therapeutic problem in many of the cancers and the current knowledge on cellular mechanisms involved is incomplete. Since A549 cells showed differential sensitivity to apoptosis with pVAX and $pNP_{73-102}$ the effects of pnP73-102 was tested using chemosensitive (OV2008) and chemoresistant (C13) ovarian cancer cells. C-13 and OV2008 ovarian cancer cells were transfected with pNP73-102 or with pVAX as control. Forty-eight hours later, cells were processed to examine apoptosis by TUNEL assay (FIG. 7). The results showed that either of the cells when transfected with pVAX did not exhibit any apoptosis. In contrast, both cell lines exhibited apoptosis as evident from TUNEL positive cells. These results indicate that pNP73-102 may induce apoptosis of epithelial adenocarcinomas irrespective of their degree of chemo-sensitivity.

Example 8

MCF-7 Breast Cancer Cells are Also Affected by NP73-102

Figure 8:
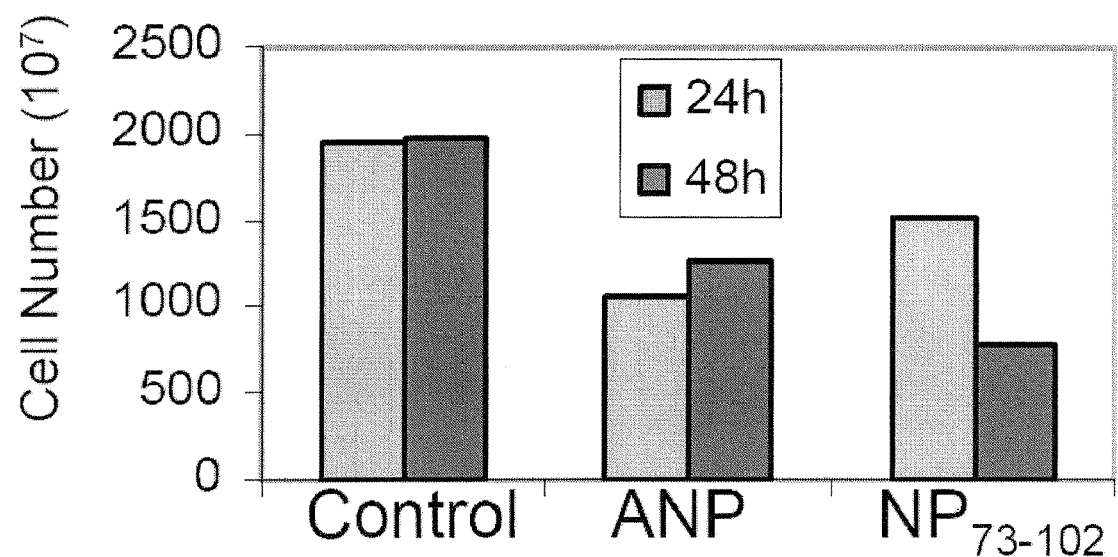
FIG. 8 shows breast cancer MCF-7 cell counts. The cells were transfected with pVAX, pANP, and $pANP_{73-102}$ and counted at 24 and 48 hours after transfection. 30 ml of Trypan Blue was mixed with 30 ml for measuring the cell viability. The results of one of two representative experiments are shown.

The effects of de novo synthesis of $NP_{73-102}$ was examined on the proliferation of the MCF-7 breast cancer cells. Cells were transfected with pVAX, pANP, or $pANP_{73-102}$. The cells were counted 24 and 48 hours after transfection and their viability was examined by trypan blue staining. The results shown in FIG. 8 indicate that there was a substantial reduction of viable cell numbers in cells transfected with $pNP_{73-102}$ compared to cells transfected with pANP or control empty vector. To further verify whether this is due to a defect in cell cycle or induction of apoptosis, a cell cycle analysis was undertaken. MCF-7 cells were transfected with pVAX or $pANP_{73-102}$ and DNA analysis was undertaken by PI staining 48 hours after transfection. Cells transfected with empty vector plasmid as control showed 37.99% cells in G0-G1, 11.28% in G2-M and 50.73% cells in G2-G1 phase. In contrast, cells transfected with $pANP_{73-102}$ showed 66.01% cells in G0-G1, 7.07% in G2-M, and 26.91% cells in G2-G1 phase. Transfection with pANP showed results similar to the $pNP_{73-102}$. These results indicate that both pANP and $pNP_{73-102}$ expression arrests cells in G0-G1 and blocks progression to S phase, suggesting that treatment with pANP and $pNP_{73-102}$ or the corresponding peptides may be useful in breast cancer patients.

All patents, patent applications, provisional applications, and publications referred to or cited herein are incorporated by reference in their entirety, including all figures, tables, and sequences, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of inhibiting the growth of cancer cells in a patient, comprising administering a polynucleotide encoding a natriuretic hormone peptide (NP) and an operably-linked promoter sequence, to the patient, wherein the cancer cells comprise lung cancer cells, breast cancer cells, ovarian cancer cells, or melanoma cells.

2. The method of claim 1, wherein the NP comprises the amino acid sequence of SEQ ID NO: 5 or a homolog of SEQ ID NO: 5 having at least one conservative amino acid substitution of SEQ ID NO: 5.

3. The method of claim 1, wherein said administering is by a route selected from the group consisting of oral, intramuscular, parenteral, intravenous, and intranasal.

4. The method of claim 1, wherein the polynucleotide is administered with a pharmaceutically acceptable carrier.

5. The method of claim 1, wherein the polynucleotide is contained within an expression vector.

6. The method of claim 5, wherein the expression vector is a DNA plasmid or virus.

7. The method of claim 1, wherein the polynucleotide sequence is administered with chitosan.

8. The method of claim 1, wherein the patient is suffering from one or more tumors, and wherein the NP causes regression of one or more of the tumors in the patient.

9. The method of claim 1, wherein the NP reduces tumor growth and metastasis in the patient.

10. The method of claim 1, wherein the patient is human.

11. The method of claim 1, wherein the cancer cells comprise lung cancer cells, and wherein the polynucleotide is administered to the airways of the patient.

12. The method of claim 2, wherein the cancer cells comprise lung cancer cells, and wherein the polynucleotide is administered to the airways of the patient.

13. The method of claim 12, wherein the patient is suffering from one or more tumors, and wherein the NP causes regression of one or more of the tumors in the patient.

14. The method of claim 1, wherein the NP comprises the amino acid sequence of SEQ ID NO: 5.

15. The method of claim 1, wherein the cancer cells comprise breast cancer cells.

16. The method of claim 2, wherein the cancer cells comprise breast cancer cells.

17. The method of claim 1, wherein the cancer cells comprise ovarian cancer cells.

18. The method of claim 2, wherein the cancer cells comprise ovarian cancer cells.

19. The method of claim 1, wherein the cancer cells comprise melanoma cells.

20. The method of claim 2, wherein the cancer cells comprise melanoma cells.

* * * * *

UNITED STATES PATENT AND TRADEMARK OFFICE
CERTIFICATE OF CORRECTION

PATENT NO. : 8,148,114 B2
APPLICATION NO. : 12/259110
DATED : April 3, 2012
INVENTOR(S) : Shyam S. Mohapatra It is certified that error appears in the above-identified patent and that said Letters Patent is hereby corrected as shown below:

Column 2,
Line 56, "such as pNP73-1102" should read --such as pNP73-102--.

Column 8,
Line 42, "natritiretic factor" should read --natriuretic factor--.

Column 22,
Line 14, "encoding $NP_{1-0}$" should read --encoding $NP_{1-30}$--.

Column 25,
Line 5, "Calf concentration" should read --$Ca^{++}$ concentration--.
Line 6, "nitric oxide (O)" should read --nitric oxide (NO)--.

Column 27,
Line 41, "Herpes simplex virus type 1 (HISV-1)" should read --Herpes simplex virus type 1 (HSV-1)--.
Line 67, "caLionic lipid delivery" should read --cationic lipid delivery--.

Column 30,
Line 25, "polynucieotides" should read --polynucleotides--.

Column 35,
Lines 22-23, "rhabdomvosarcoma" should read --rhabdomyosarcoma--.

Column 38,
Line 30, "the 2-p origin" should read --the 2-µ origin--.
Line 55, "Hela cells" should read --HeLa cells--.

Signed and Sealed this
Seventeenth Day of July, 2012

David J. Kappos
*Director of the United States Patent and Trademark Office*

Column 43,
Line 25, "polyniucleotides" should read --polynucleotides--.

SEQUENCE LISTING

```
<160> NUMBER OF SEQ ID NOS: 22

<210> SEQ ID NO 1
<211> LENGTH: 30
<212> TYPE: PRT
<213> ORGANISM: Homo sapiens

<400> SEQUENCE: 1

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp
            20                  25                  30

<210> SEQ ID NO 2
<211> LENGTH: 37
<212> TYPE: PRT
<213> ORGANISM: Homo sapiens

<400> SEQUENCE: 2

Glu Val Val Pro Pro Gln Val Leu Ser Glu Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 3
<211> LENGTH: 20
<212> TYPE: PRT
<213> ORGANISM: Homo sapiens

<400> SEQUENCE: 3

Ser Ser Asp Arg Ser Ala Leu Leu Lys Ser Lys Leu Arg Ala Leu Leu
1               5                   10                  15

Thr Ala Pro Arg
        20
```

```
<210> SEQ ID NO 4
<211> LENGTH: 28
<212> TYPE: PRT
<213> ORGANISM: Homo sapiens

<400> SEQUENCE: 4

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 5
<211> LENGTH: 30
<212> TYPE: PRT
<213> ORGANISM: Mus musculus

<400> SEQUENCE: 5

Gly Ser Pro Trp Asp Pro Ser Asp Arg Ser Ala Leu Leu Lys Ser Lys
1               5                   10                  15

Leu Arg Ala Leu Leu Ala Gly Pro Arg Ser Leu Arg Arg Ser
            20                  25                  30

<210> SEQ ID NO 6
<211> LENGTH: 37
<212> TYPE: PRT
<213> ORGANISM: Mus musculus

<400> SEQUENCE: 6

Val Ser Asn Thr Asp Leu Met Asp Phe Lys Asn Leu Leu Asp His Leu
1               5                   10                  15

Glu Glu Lys Met Pro Val Glu Asp Glu Val Met Pro Pro Gln Ala Leu
            20                  25                  30

Ser Glu Gln Thr Glu
        35

<210> SEQ ID NO 7
<211> LENGTH: 151
<212> TYPE: PRT
<213> ORGANISM: Homo sapiens

<400> SEQUENCE: 7

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125
```

Ser Cys Phe Gly Gly Arg Met Asp Arg Ile Gly Ala Gln Ser Gly Leu
130                 135                 140

Gly Cys Asn Ser Phe Arg Tyr
145                 150

<210> SEQ ID NO 8
<211> LENGTH: 35
<212> TYPE: DNA
<213> ORGANISM: Mus musculus

<400> SEQUENCE: 8
gacggcaagc ttactatggg cagcccctgg gaccc                          35

<210> SEQ ID NO 9
<211> LENGTH: 33
<212> TYPE: DNA
<213> ORGANISM: Mus musculus

<400> SEQUENCE: 9 accccctcg agttattatc ttcgtaggct ccg                             33

<210> SEQ ID NO 10
<211> LENGTH: 33
<212> TYPE: DNA
<213> ORGANISM: Mus musculus

<400> SEQUENCE: 10
aatcctaagc ttagtatggt gtccaacaca gat                            33

<210> SEQ ID NO 11
<211> LENGTH: 41
<212> TYPE: DNA
<213> ORGANISM: Mus musculus

<400> SEQUENCE: 11
tgcgaactcg agttactcag tctgctcact cagggcctgc g                   41

<210> SEQ ID NO 12
<211> LENGTH: 90
<212> TYPE: DNA
<213> ORGANISM: Mus musculus

<400> SEQUENCE: 12
ggcagcccct gggacccctc cgatagatct gccctcttga aaagcaaact gagggctctg    60
ctcgctggcc ctcggagcct acgaagatcc                                    90

<210> SEQ ID NO 13
<211> LENGTH: 117
<212> TYPE: DNA
<213> ORGANISM: Mus musculus

<400> SEQUENCE: 13
atggtgtcca acacagatct gatggatttc aagaacctgc tagaccacct ggaggagaag    60
atgccggtag aagatgaggt catgcccccg caggccctga gtgagcagac tgagtaa       117

<210> SEQ ID NO 14
<211> LENGTH: 845
<212> TYPE: DNA
<213> ORGANISM: Homo sapiens -continued

```
<400> SEQUENCE: 14
tggcgaggga cagacgtagg ccaagagagg ggaaccagag aggaaccaga ggggagagac     60
agagcagcaa gcagtggatt gctccttgac gacgccagca tgagctcctt ctccaccacc    120
accgtgagct tcctccttttt actggcattc cagctcctag gtcagaccag agctaatccc    180
atgtacaatg ccgtgtccaa cgcagacctg atggatttca agaatttgct ggaccatttg    240
gaagaaaaga tgccttttaga agatgaggtc gtgccccac aagtgctcag tgagccgaat     300
gaagaagcgg gggctgctct cagccccctc cctgaggtgc ctccctggac cggggaagtc    360
agcccagccc agagagatgg aggtgccctc ggcgggggcc cctgggactc ctctgatcga    420
tctgccctcc taaaaagcaa gctgagggcg ctgctcactg cccctcggag cctgcggaga    480
tccagctgct cgggggcag gatggacagg attggagccc agagcggact gggctgtaac     540
agcttccggt actgaagata acagccaggg aggacaagca gggctgggcc tagggacaga    600
ctgcaagagg ctcctgtccc ctggggtctc tgctgcattt tgtgtcatct tgttgccatgg   660 agttgtgatc atcccatcta agctgcagct tcctgtcaac acttctcaca tcttatgcta    720
actgtagata aagtggtttg atggtgactt cctcgcctct cccaccccat gcattaaatt    780
ttaaggtaga acctcacctg ttactgaaag tggtttgaaa gtgaataaac ttcagcacca    840
tggac                                                                845

<210> SEQ ID NO 15
<211> LENGTH: 2583
<212> TYPE: DNA
<213> ORGANISM: Homo sapiens

<400> SEQUENCE: 15
ggatccattt gtctcgggct gctggctgcc tgccatttcc tcctctccac ccttatttgg     60
aggccctgac agctgagcca caaacaaacc aggggagctg gcaccagca agcgtcaccc    120 tctgtttccc cgcacggtac cagcgtcgag gagaaagaat cctgaggcac ggcggtgaga    180
taaccaagga ctcttttta ctcttctcac acctttgaag tgggagcctc ttgagtcaaa    240
tcagtaagaa tgcggctctt gcagctgagg gtctgggggg ctgttggggc tgcccaaggc    300
agagaggggc tgtgacaagc cctgcggatg ataactttaa aagggcatct cctgctggct   360
tctcacttgg cagctttatc actgcaagtg acagaatggg gagggttctg tctctcctgc    420
gtgcttggag agctgggggg ctataaaaag aggcggcact gggcagctgg gagacaggga    480
cagacgtagg ccaagagagg ggaaccagag aggaaccaga ggggagagac agagcagcaa    540
gcagtggatt gctccttgac gacgccagca tgagctcctt ctccaccacc accgtgagct    600
tcctcctttt actggcattc cagctcctag gtcagaccag agctaatccc atgtacaatg    660
ccgtgtccaa cgcagacctg atggatttca aggtagggcc aggaaagcgg gtgcagtctg    720
gggccagggg gctttctgat gctgtgctca ctcctcttga tttcctccaa gtcagtgagg    780 tttatcccctt tccctgtatt ttccttttct aaagaatttg ctggaccatt tggaagaaaa    840
gatgccttta gaagatgagg tcgtgccccc acaagtgctc agtgagccga atgaagaagc    900
gggggctgct ctcagccccc tccctgaggt gcctccctgg accggggaag tcagcccagc    960
ccagagagat ggaggtgccc tcgggcgggg cccctgggac tcctctgatc gatctgccct   1020
cctaaaaagc aagctgaggg cgctgctcac tgcccctcgg agcctgcgga gatccagctg   1080 cttcggggggc aggatggaca ggattggagc ccagagcgga ctgggctgta acagcttccg   1140
ggtaagagga actggggatg gaaatgggat gggatggaca ctactgggag acaccttcag   1200
```

```
caggaaaggg accaatgcag aagctcattc cctctcaagt ttctgcccca acacccagag    1260
tgccccatgg gtgtcaggac atgccatcta ttgtccttag ctagtctgct gagaaaatgc    1320
ttaaaaaaaa aagggggggg gctgggcacg gtcgtcacgc ctgtaatccc agcactttgg    1380
gaggccaggc agcggatcat gaggtcaaga gatcaagact atcctggcca acatggtgaa    1440
accccagctc tactaaaaat acaaaaatta gctgggtgtg tggcgggcac ctgtactctc    1500
agctacttgg gaggctgagg caggagaatc acttgaaccc aggaggcaga ggttgcagtg    1560
agcagagatc acgccactgc agtccagcct aggtgataga gcgagactgt ctcaaaaaaa    1620
aaaaaaaaag gccaggcgcg gtggctcacg cctgtaatcc cagcgctttg ggaggccaag    1680
gcgggtggat cacgaggtca ggagatggag accatcctgg ctaacacggt gaaacccccgt   1740 ctctactaaa aatacaaaaa attagccagg cgtggtggca ggcgcctgta agtcctagct    1800
actccggagg ctgaggcagg agaatggcgt gaacccggga ggcggagctt gcagtgagca    1860
gagatggcac cactgcactc cagcctgggc gacagagcaa gactccgtct caaaaaaaaa    1920 aaaaaaaaa gcaactgcca ctagcactgg gaaattaaaa tattcataga gccaagttat     1980
ctttgcatgg ctgattagca gttcatattc ctccccagaa ttgcaagatc ctgaagggct    2040
taagtgaaat ttactctgat gagtaacttg cttatcaatt catgaagctc agagggtcat    2100
caggctgggg tgggggccgg tgggaagcag gtggtcagta atcaagttca gaggatgggc    2160
acactcatac atgaagctga cttttccagg acagccaggt caccaagcca gatatgtctg    2220
tgttctcttt gcagtactga agataacagc caggggaggac aagcagggct gggcctaggg    2280
acagactgca agaggctcct gtcccctggg gtctctgctg catttgtgtc atcttgttgc    2340
catggagttg tgatcatccc atctaagctg cagcttcctg tcaacacttc tcacatctta    2400
tgctaactgt agataaagtg gtttgatggt gacttcctcg cctctcccac cccatgcatt    2460 aaatttttaag gtagaacctc acctgttact gaaagtggtt tgaaagtgaa taaacttcag    2520
caccatggac agaagacaaa tgcctgcgtt ggtgtgctttt ctttcttctt gggaagagaa    2580
ttc                                                                  2583
```

<210> SEQ ID NO 16
<211> LENGTH: 152
<212> TYPE: PRT
<213> ORGANISM: Mus musculus

<400> SEQUENCE: 16

Met Gly Ser Phe Ser Ile Thr Leu Gly Phe Phe Leu Val Leu Ala Phe
1               5                   10                  15

Trp Leu Pro Gly His Ile Gly Ala Asn Pro Val Tyr Ser Ala Val Ser
            20                  25                  30

Asn Thr Asp Leu Met Asp Phe Lys Asn Leu Leu Asp His Leu Glu Glu
        35                  40                  45

Lys Met Pro Val Glu Asp Glu Val Met Pro Gln Ala Leu Ser Glu
    50                  55                  60

Gln Thr Glu Glu Ala Gly Ala Ala Leu Ser Ser Leu Pro Glu Val Pro
65                  70                  75                  80

Pro Trp Thr Gly Glu Val Asn Pro Pro Leu Arg Asp Gly Ser Ala Leu
                85                  90                  95

Gly Arg Ser Pro Trp Asp Pro Ser Asp Arg Ser Ala Leu Leu Lys Ser
            100                 105                 110

Lys Leu Arg Ala Leu Leu Ala Gly Pro Arg Ser Leu Arg Arg Ser Ser
        115                 120                 125

```
Cys Phe Gly Gly Arg Ile Asp Arg Ile Gly Ala Gln Ser Gly Leu Gly
            130                 135                 140

Cys Asn Ser Phe Arg Tyr Arg Arg
145                 150
```

<210> SEQ ID NO 17
<211> LENGTH: 878
<212> TYPE: DNA
<213> ORGANISM: Mus musculus
<220> FEATURE:
<221> NAME/KEY: misc_feature
<222> LOCATION: (81)..(539)
<223> OTHER INFORMATION: coding sequence for preproANP

<400> SEQUENCE: 17

```
caaaagctga gagagagaga gaaagaaacc agagtgggca gagacagcaa acatcagatc      60
gtgccccgac ccacgccagc atgggctcct tctccatcac cctgggcttc ttcctcgtct     120
tggccttttg gcttccaggc catattggag caaatcctgt gtacagtgcg gtgtccaaca     180
cagatctgat ggatttcaag aacctgctag accacctgga ggagaagatg ccggtagaag     240
atgaggtcat gccccgcag gccctgagtg agcagactga ggaagcaggg gccgcactta      300
gctccctccc cgaggtgcct ccctggactg gggaggtcaa cccacctctg agagacggca     360
gtgctctagg gcgcagcccc tgggacccct ccgatagatc tgccctcttg aaaagcaaac     420
tgagggctct gctcgctggc cctcggagcc tacgaagatc cagctgcttc ggggtagga     480
ttgacaggat tggagcccag agtggactag gctgcaacag cttccggtac cgaagataac     540
agccaaggag gaaaaggcag tcgattctgc ttgagcagat cgcaaaagat cctaagccct     600
tgtggtgtgt cacgcagctt ggtcacattg ccactgtggc gtggtgaaca ccctcctgga     660
gctgcggctt cctgccttca tctatcacga tcgatgttaa atgtagatga gtggtctagt     720
ggggtcttgc ctctcccact ctgcatatta aggtagatcc tcacccttt cagaaagcag      780
ttggaaaaaa aaaaaagaa taaacttcag caccaaggac agacgccgag gccctgatgt      840
gcttctttgg cttctgccct cagttctttg ctctccccc                             878
```

<210> SEQ ID NO 18
<211> LENGTH: 1061
<212> TYPE: PRT
<213> ORGANISM: Homo sapiens

<400> SEQUENCE: 18

```
Met Pro Gly Pro Arg Arg Pro Ala Gly Ser Arg Leu Arg Leu Leu
1               5                   10                  15

Leu Leu Leu Leu Pro Pro Leu Leu Leu Leu Leu Arg Gly Ser His Ala
                20                  25                  30

Gly Asn Leu Thr Val Ala Val Val Leu Pro Leu Ala Asn Thr Ser Tyr
            35                  40                  45

Pro Trp Ser Trp Ala Arg Val Gly Pro Ala Val Glu Leu Ala Leu Ala
        50                  55                  60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Ala Pro Val Gly Arg Phe
        115                 120                 125
```

-continued

```
Thr Ala His Trp Arg Val Pro Leu Leu Thr Ala Gly Ala Pro Ala Leu
        130                 135                 140
Gly Phe Gly Val Lys Asp Glu Tyr Ala Leu Thr Thr Arg Ala Gly Pro
145                 150                 155                 160
Ser Tyr Ala Lys Leu Gly Asp Phe Val Ala Leu His Arg Arg Leu
                165                 170                 175
Gly Trp Glu Arg Gln Ala Leu Met Leu Tyr Ala Tyr Arg Pro Gly Asp
                180                 185                 190
Glu Glu His Cys Phe Phe Leu Val Glu Gly Leu Phe Met Arg Val Arg
            195                 200                 205
Asp Arg Leu Asn Ile Thr Val Asp His Leu Glu Phe Ala Glu Asp Asp
        210                 215                 220
Leu Ser His Tyr Thr Arg Leu Leu Arg Thr Met Pro Arg Lys Gly Arg
225                 230                 235                 240
Val Ile Tyr Ile Cys Ser Ser Pro Asp Ala Phe Arg Thr Leu Met Leu
                245                 250                 255
Leu Ala Leu Glu Ala Gly Leu Cys Gly Glu Asp Tyr Val Phe Phe His
                260                 265                 270
Leu Asp Ile Phe Gly Gln Ser Leu Gln Gly Gly Gln Gly Pro Ala Pro
                275                 280                 285
Arg Arg Pro Trp Glu Arg Gly Asp Gly Gln Asp Val Ser Ala Arg Gln
        290                 295                 300
Ala Phe Gln Ala Ala Lys Ile Ile Thr Tyr Lys Asp Pro Asp Asn Pro
305                 310                 315                 320
Glu Tyr Leu Glu Phe Leu Lys Gln Leu Lys His Leu Ala Tyr Glu Gln
                325                 330                 335
Phe Asn Phe Thr Met Glu Asp Val Leu Val Asn Thr Ile Pro Ala Ser
                340                 345                 350
Phe His Asp Gly Leu Leu Leu Tyr Ile Gln Ala Val Thr Glu Thr Leu
            355                 360                 365
Ala His Gly Gly Thr Val Thr Asp Gly Glu Asn Ile Thr Gln Arg Met
        370                 375                 380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
Asn Gly Ala Phe Arg Val Val Leu Asn Tyr Asn Gly Thr Ser Gln Glu
                420                 425                 430
Leu Val Ala Val Ser Gly Arg Lys Leu Asn Trp Pro Leu Gly Tyr Pro
            435                 440                 445
Pro Pro Asp Ile Pro Lys Cys Gly Phe Asp Asn Glu Asp Pro Ala Cys
        450                 455                 460
Asn Gln Asp His Leu Ser Thr Leu Glu Val Leu Ala Leu Val Gly Ser
465                 470                 475                 480
Leu Ser Leu Leu Gly Ile Leu Ile Val Ser Phe Ile Tyr Arg Lys
                485                 490                 495
Met Gln Leu Glu Lys Glu Leu Ala Ser Glu Leu Trp Arg Val Arg Trp
            500                 505                 510
Glu Asp Val Glu Pro Ser Ser Leu Glu Arg His Leu Arg Ser Ala Gly
            515                 520                 525
Ser Arg Leu Thr Leu Ser Gly Arg Gly Ser Asn Tyr Gly Ser Leu Leu
        530                 535                 540
Thr Thr Glu Gly Gln Phe Gln Val Phe Ala Lys Thr Ala Tyr Tyr Lys
545                 550                 555                 560
```

```
Gly Asn Leu Val Ala Val Lys Arg Val Asn Arg Lys Arg Ile Glu Leu
            565                 570                 575
Thr Arg Lys Val Leu Phe Glu Leu Lys His Met Arg Asp Val Gln Asn
            580                 585                 590
Glu His Leu Thr Arg Phe Val Gly Ala Cys Thr Asp Pro Pro Asn Ile
            595                 600                 605
Cys Ile Leu Thr Glu Tyr Cys Pro Arg Gly Ser Leu Gln Asp Ile Leu
            610                 615                 620
Glu Asn Glu Ser Ile Thr Leu Asp Trp Met Phe Arg Tyr Ser Leu Thr
625                 630                 635                 640
Asn Asp Ile Val Lys Gly Met Leu Phe Leu His Asn Gly Ala Ile Cys
            645                 650                 655
Ser His Gly Asn Leu Lys Ser Ser Asn Cys Val Val Asp Gly Arg Phe
            660                 665                 670
Val Leu Lys Ile Thr Asp Tyr Gly Leu Glu Ser Phe Arg Asp Leu Asp
            675                 680                 685
Pro Glu Gln Gly His Thr Val Tyr Ala Lys Lys Leu Trp Thr Ala Pro
            690                 695                 700
Glu Leu Leu Arg Met Ala Ser Pro Pro Val Arg Gly Ser Gln Ala Gly
705                 710                 715                 720
Asp Val Tyr Ser Phe Gly Ile Ile Leu Gln Glu Ile Ala Leu Arg Ser
            725                 730                 735
Gly Val Phe His Val Glu Gly Leu Asp Leu Ser Pro Lys Glu Ile Ile
            740                 745                 750
Glu Arg Val Thr Arg Gly Glu Gln Pro Pro Phe Arg Pro Ser Leu Ala
            755                 760                 765
Leu Gln Ser His Leu Glu Glu Leu Gly Leu Leu Met Gln Arg Cys Trp
            770                 775                 780
Ala Glu Asp Pro Gln Glu Arg Pro Pro Phe Gln Gln Ile Arg Leu Thr
785                 790                 795                 800
Leu Arg Lys Phe Asn Arg Glu Asn Ser Ser Asn Ile Leu Asp Asn Leu
            805                 810                 815
Leu Ser Arg Met Glu Gln Tyr Ala Asn Asn Leu Glu Glu Leu Val Glu
            820                 825                 830
Glu Arg Thr Gln Ala Tyr Leu Glu Glu Lys Arg Lys Ala Glu Ala Leu
            835                 840                 845
Leu Tyr Gln Ile Leu Pro His Ser Val Ala Glu Gln Leu Lys Arg Gly
            850                 855                 860
Glu Thr Val Gln Ala Glu Ala Phe Asp Ser Val Thr Ile Tyr Phe Ser
865                 870                 875                 880
Asp Ile Val Gly Phe Thr Ala Leu Ser Ala Glu Ser Thr Pro Met Gln
            885                 890                 895
Val Val Thr Leu Leu Asn Asp Leu Tyr Thr Cys Phe Asp Ala Val Ile
            900                 905                 910
Asp Asn Phe Asp Val Tyr Lys Val Glu Thr Ile Gly Asp Ala Tyr Met
            915                 920                 925
Val Val Ser Gly Leu Pro Val Arg Asn Gly Arg Leu His Ala Cys Glu
            930                 935                 940
Val Ala Arg Met Ala Leu Ala Leu Leu Asp Ala Val Arg Ser Phe Arg
945                 950                 955                 960
Ile Arg His Arg Pro Gln Glu Gln Leu Arg Leu Arg Ile Gly Ile His
            965                 970                 975
Thr Gly Pro Val Cys Ala Gly Val Val Gly Leu Lys Met Pro Arg Tyr
            980                 985                 990
```

```
Cys Leu Phe Gly Asp Thr Val Asn Thr Ala Ser Arg Met Glu Ser Asn
        995                 1000                1005

Gly Glu  Ala Leu Lys Ile His  Leu Ser Ser Glu Thr  Lys Ala Val
    1010             1015                 1020

Leu Glu Glu Phe Gly Gly Phe  Glu Leu Glu Leu Arg  Gly Asp Val
    1025            1030                 1035

Glu Met Lys Gly Lys Gly Lys  Val Arg Thr Tyr Trp  Leu Leu Gly
    1040            1045                 1050

Glu Arg Gly Ser Ser Thr Arg  Gly
    1055            1060

<210> SEQ ID NO 19
<211> LENGTH: 4246
<212> TYPE: DNA
<213> ORGANISM: Homo sapiens

<400> SEQUENCE: 19
```

| | | | | | |
|---|---|---|---|---|---|
| ggttccctcc | ggatagccgg | agacttgggc | cggccggacg | ccccttctgg | cacactccct     60 |
| ggggcaggcg | ctcacgcacg | ctacaaacac | acactcctct | ttcctccctc | gcgcgccctc    120 |
| tctcatcctt | cttcacgaag | cgctcactcg | cacccttct | ctctctctct | ctctctctaa    180 |
| cacgcacgca | cactcccagt | tgttcacact | cgggtcctct | ccagcccgac | gttctcctgg    240 |
| cacccacctg | ctccgcggcg | ccctgcgcgc | ccccctcggt | cgcgccctt | gcgctctcgg    300 |
| cccagaccgt | cgcagctaca | gggggcctcg | agcccgggg | tgagcgtccc | cgtcccgctc    360 |
| ctgctccttc | ccatagggac | gcgcctgatg | cctgggaccg | gccgctgagc | ccaaggggac    420 |
| cgaggaggcc | atggtaggag | cgctcgcctg | ctgcggtgcc | cgctgaggcc | atgccggggc    480 |
| cccggcgccc | cgctggctcc | cgcctgcgcc | tgctcctgct | cctgctgctg | ccgccgctgc    540 |
| tgctgctgct | ccggggcagc | cacgcgggca | acctgacggt | agccgtggta | ctgccgctgg    600 |
| ccaatacctc | gtaccctgg | tcgtgggcgc | gcgtgggacc | cgccgtggag | ctggccctgg    660 |
| cccaggtgaa | ggcgcgcccc | gacttgctgc | cgggctggac | ggtccgcacg | gtgctgggca    720 |
| gcagcgaaaa | cgcgctgggc | gtctgctccg | acaccgcagc | gccccggcc | gcggtggacc    780 |
| tcaagtggga | gcacaacccc | gctgtgttcc | tgggccccgg | ctgcgtgtac | gccgccgccc    840 |
| cagtggggcg | cttcaccgcg | cactggcggg | tcccgctgct | gaccgccggc | gccccggcgc    900 |
| tgggcttcgg | tgtcaaggac | gagtatgcgc | tgaccacccg | cgcggggccc | agctacgcca    960 |
| agctggggga | cttcgtggcg | cgctgcacc | gacggctggg | ctgggagcgc | caagcgctca   1020 |
| tgctctacgc | ctaccggccg | ggtgacgaag | agcactgctt | cttcctcgtg | gagggctgt   1080 |
| tcatgcgggt | ccgcgaccgc | ctcaatatta | cggtggacca | cctggagttc | gccgaggacg   1140 |
| acctcagcca | ctacaccagg | ctgctgcgga | ccatgccgcg | caaaggccga | gttatctaca   1200 |
| tctgcagctc | ccctgatgcc | ttcagaaccc | tcatgctcct | ggccctggaa | gctggcttgt   1260 |
| gtggggagga | ctacgttttc | ttccacctgg | atatctttgg | gcaaagcctg | caaggtggac   1320 |
| agggccctgc | tccccgcagg | ccctgggaga | gagggatgg | gcaggatgtc | agtgcccgcc   1380 |
| aggcctttca | ggctgccaaa | atcattacat | ataaagaccc | agataatccc | gagtacttgg   1440 |
| aattcctgaa | gcagttaaaa | cacctggcct | atgagcagtt | caacttcacc | atggaggatg   1500 |
| tcctggtgaa | caccatccca | gcatccttcc | acgacgggc | cctgctctat | atccaggcag   1560 |
| tgacggagac | tctggcacat | ggggaactg | ttactgatgg | ggagaacatc | actcagcgga   1620 |
| tgtggaaccg | aagctttcaa | ggtgtgacag | gatacctgaa | aattgatagc | agtggcgatc   1680 |
| gggaaacaga | cttctccctc | tgggatatgg | atcccgagaa | tggtgccttc | agggttgtac   1740 |

-continued

| | |
|---|---|
| tgaactacaa tgggacttcc caagagctgg tggctgtgtc ggggcgcaaa ctgaactggc | 1800 |
| ccctggggta ccctcctcct gacatcccca aatgtggctt tgacaacgaa gacccagcat | 1860 |
| gcaaccaaga tcacctttcc accctggagg tgctggcttt ggtgggcagc ctctccttgc | 1920 |
| tcggcattct gattgtctcc ttcttcatat acaggaagat gcagctggag aaggaactgg | 1980 |
| cctcggagct gtggcgggtg cgctgggagg acgttgagcc cagtagcctt gagaggcacc | 2040 |
| tgcggagtgc aggcagccgg ctgaccctga gcgggagagg ctccaattac ggctccctgc | 2100 |
| taaccacaga gggccagttc caagtctttg ccaagacagc atattataag ggcaacctcg | 2160 |
| tggctgtgaa acgtgtgaac cgtaaacgca ttgagctgac acgaaaagtc ctgtttgaac | 2220 |
| tgaagcatat gcgggatgtg cagaatgaac acctgaccag gtttgtggga gcctgcaccg | 2280 |
| accccccccaa tatctgcatc ctcacagagt actgtccccg tgggagcctg caggacattc | 2340 |
| tggagaatga gagcatcacc ctggactgga tgttccggta ctcactcacc aatgacatcg | 2400 |
| tcaagggcat gctgtttcta cacaatgggg ctatctgttc ccatgggaac ctcaagtcat | 2460 |
| ccaactgcgt ggtagatggg cgctttgtgc tcaagatcac cgactatggg ctggagagct | 2520 |
| tcagggacct ggacccagag caaggacaca ccgtttatgc caaaaagctg tggacggccc | 2580 |
| ctgagctcct gcgaatggct tcaccccctg tgcggggctc ccaggctggt gacgtataca | 2640 |
| gctttgggat catccttcag gagattgccc tgaggagtgg ggtcttccac gtggaaggtt | 2700 |
| tggacctgag ccccaaagag atcatcgagc gggtgactcg gggtgagcag cccccctccc | 2760 |
| ggccctccct ggccctgcag agtcacctgg aggagttggg gctgctcatg cagcggtgct | 2820 |
| gggctgagga cccacaggag aggccaccat tccagcagat ccgcctgacg ttgcgcaaat | 2880 |
| ttaacaggga gaacagcagc aacatcctgg acaacctgct gtcccgcatg gagcagtacg | 2940 |
| cgaacaatct ggaggaactg gtggaggagc ggacccaggc atacctggag gagaagcgca | 3000 |
| aggctgaggc cctgctctac cagatcctgc ctcactcagt ggctgagcag ctgaagcgtg | 3060 |
| gggagacggt gcaggccgaa gccttttgaca gtgttaccat ctacttcagt gacattgtgg | 3120 |
| gtttcacagc gctgtcggcg gagagcacgc ccatgcaggt ggtgaccctg ctcaatgacc | 3180 |
| tgtacacttg ctttgatgct gtcatagaca actttgatgt gtacaaggtg gagacaattg | 3240 |
| gcgatgccta catggtggtg tcagggctcc ctgtgcggaa cgggcggcta cacgcctgcg | 3300 |
| aggtagcccg catggccctg gcactgctgg atgctgtgcg ctccttccga atccgccacc | 3360 |
| ggccccagga gcagctgcgc ttgcgcattg gcatccacac aggacctgtg tgtgctggag | 3420 |
| tggtgggact gaagatgccc cgttactgtc tctttgggga tacagtcaac acagcctcaa | 3480 |
| gaatggagtc taatggggaa gccctgaaga tccacttgtc ttctgagacc aaggctgtcc | 3540 |
| tggaggagtt tggtggtttc gagctggagc ttcgagggga tgtagaaatg aagggcaaag | 3600 |
| gcaaggttcg gacctactgg ctccttgggg agaggggggag tagcacccga ggctgacctg | 3660 |
| cctcctctcc tatccctcca cacctcccct accctgtgcc agaagcaaca gaggtgccag | 3720 |
| gcctcagcct cacccacagc agcccatcg ccaaaggatg gaagtaattt gaatagctca | 3780 |
| ggtgtgctta ccccagtgaa gacaccagat aggacctctg agaggggact ggcatggggg | 3840 |
| gatctcagag cttacaggct gagccaagcc cacggccatg cacagggaca ctcacacagg | 3900 |
| cacacgcacc tgctctccac ctggactcag gccgggctgg gctgtggatt cctgatcccc | 3960 |
| tcccctcccc atgctctcct ccctcagcct tgctaccctg tgacttactg ggaggagaaa | 4020 |
| gagtcacctg aaggggaaca tgaaaagaga ctaggtgaag agagggcagg ggagcccaca | 4080 |
| tctggggctg gcccacaata cctgctcccc cgaccccctc cacccagcag tagacacagt | 4140 |

```
gcacagggga gaagaggggt ggcgcagaag ggttgggggc ctgtatgcct tgcttctacc    4200
atgagcagag acaattaaaa tctttattcc aaaaaaaaaa aaaaaa                  4246
```

<210> SEQ ID NO 20
<211> LENGTH: 541
<212> TYPE: PRT
<213> ORGANISM: Homo sapiens

<400> SEQUENCE: 20

```
Met Pro Ser Leu Leu Val Leu Thr Phe Ser Pro Cys Val Leu Leu Gly
1               5                   10                  15

Trp Ala Leu Leu Ala Gly Gly Thr Gly Gly Gly Val Gly Gly Gly
            20                  25                  30

Gly Gly Gly Ala Gly Ile Gly Gly Arg Gln Glu Arg Glu Ala Leu
        35                  40                  45

Pro Pro Gln Lys Ile Glu Val Leu Val Leu Pro Gln Asp Asp Ser
    50                  55                  60

Tyr Leu Phe Ser Leu Thr Arg Val Arg Pro Ala Ile Glu Tyr Ala Leu
65                  70                  75                  80

Arg Ser Val Glu Gly Asn Gly Thr Gly Arg Arg Leu Leu Pro Pro Gly
                85                  90                  95

Thr Arg Phe Gln Val Ala Tyr Glu Asp Ser Asp Cys Gly Asn Arg Ala
            100                 105                 110

Leu Phe Ser Leu Val Asp Arg Val Ala Ala Arg Gly Ala Lys Pro
        115                 120                 125

Asp Leu Ile Leu Gly Pro Val Cys Glu Tyr Ala Ala Ala Pro Val Ala
    130                 135                 140

Arg Leu Ala Ser His Trp Asp Leu Pro Met Leu Ser Ala Gly Ala Leu
145                 150                 155                 160

Ala Ala Gly Phe Gln His Lys Asp Ser Glu Tyr Ser His Leu Thr Arg
                165                 170                 175

Val Ala Pro Ala Tyr Ala Lys Met Gly Glu Met Met Leu Ala Leu Phe
            180                 185                 190

Arg His His His Trp Ser Arg Ala Ala Leu Val Tyr Ser Asp Asp Lys
        195                 200                 205

Leu Glu Arg Asn Cys Tyr Phe Thr Leu Glu Gly Val His Glu Val Phe
    210                 215                 220

Gln Glu Glu Gly Leu His Thr Ser Ile Tyr Ser Phe Asp Glu Thr Lys
225                 230                 235                 240

Asp Leu Asp Leu Glu Asp Ile Val Arg Asn Ile Gln Ala Ser Glu Arg
                245                 250                 255

Val Val Ile Met Cys Ala Ser Ser Asp Thr Ile Arg Ser Ile Met Leu
            260                 265                 270

Val Ala His Arg His Gly Met Thr Ser Gly Asp Tyr Ala Phe Phe Asn
        275                 280                 285

Ile Glu Leu Phe Asn Ser Ser Ser Tyr Gly Asp Gly Ser Trp Lys Arg
    290                 295                 300

Gly Asp Lys His Asp Phe Glu Ala Lys Gln Ala Tyr Ser Ser Leu Gln
305                 310                 315                 320

Thr Val Thr Leu Leu Arg Thr Val Lys Pro Glu Phe Glu Lys Phe Ser
                325                 330                 335

Met Glu Val Lys Ser Ser Val Glu Lys Gln Gly Leu Asn Met Glu Asp
            340                 345                 350

Tyr Val Asn Met Phe Val Glu Gly Phe His Asp Ala Ile Leu Leu Tyr
        355                 360                 365
```

| | | | | | | | | | | | |
|---|---|---|---|---|---|---|---|---|---|---|---|
| Val | Leu | Ala | Leu | His | Glu | Val | Leu | Arg | Ala | Gly | Tyr | Ser | Lys | Lys | Asp |
| | 370 | | | | 375 | | | | 380 | | |
| Gly | Gly | Lys | Ile | Ile | Gln | Gln | Thr | Trp | Asn | Arg | Thr | Phe | Glu | Gly | Ile |
| 385 | | | | | 390 | | | | | 395 | | | | | 400 |
| Ala | Gly | Gln | Val | Ser | Ile | Asp | Ala | Asn | Gly | Arg | Tyr | Gly | Asp | Phe |
| | | | | 405 | | | | | 410 | | | | | 415 |
| Ser | Val | Ile | Ala | Met | Thr | Asp | Val | Glu | Ala | Gly | Thr | Gln | Glu | Val | Ile |
| | | | | 420 | | | | | 425 | | | | | 430 |
| Gly | Asp | Tyr | Phe | Gly | Lys | Glu | Gly | Arg | Phe | Glu | Met | Arg | Pro | Asn | Val |
| | | 435 | | | | | 440 | | | | | 445 |
| Lys | Tyr | Pro | Trp | Gly | Pro | Leu | Lys | Leu | Arg | Ile | Asp | Glu | Asn | Arg | Ile |
| | 450 | | | | | 455 | | | | | 460 |
| Val | Glu | His | Thr | Asn | Ser | Ser | Pro | Cys | Lys | Ser | Ser | Gly | Gly | Leu | Glu |
| 465 | | | | | 470 | | | | | 475 | | | | | 480 |
| Glu | Ser | Ala | Val | Thr | Gly | Ile | Val | Val | Gly | Ala | Leu | Leu | Gly | Ala | Gly |
| | | | | 485 | | | | | 490 | | | | | 495 |
| Leu | Leu | Met | Ala | Phe | Tyr | Phe | Phe | Arg | Lys | Lys | Tyr | Arg | Ile | Thr | Ile |
| | | | 500 | | | | | 505 | | | | | 510 |
| Glu | Arg | Arg | Thr | Gln | Gln | Glu | Glu | Ser | Asn | Leu | Gly | Lys | His | Arg | Glu |
| | | 515 | | | | | 520 | | | | | 525 |
| Leu | Arg | Glu | Asp | Ser | Ile | Arg | Ser | His | Phe | Ser | Val | Ala |
| | 530 | | | | | 535 | | | | | 540 |

<210> SEQ ID NO 21
<211> LENGTH: 53
<212> TYPE: DNA
<213> ORGANISM: Artificial Sequence
<220> FEATURE:
<223> OTHER INFORMATION: siRNA specific for NPR-A

<400> SEQUENCE: 21
tattacggtg gaccacctgt tcaagagaca ggtggtccac cgtaatattt ttt          53

<210> SEQ ID NO 22
<211> LENGTH: 53
<212> TYPE: DNA
<213> ORGANISM: Artificial Sequence
<220> FEATURE:
<223> OTHER INFORMATION: siRNA specific for NPR-A

<400> SEQUENCE: 22
agaattccag aaacgcagct tcaagagagc tgcgtttctg gaattctttt ttt          53